United States Patent [19]

Ladner et al.

[11] Patent Number: 5,260,203
[45] Date of Patent: Nov. 9, 1993

[54] SINGLE POLYPEPTIDE CHAIN BINDING MOLECULES

[75] Inventors: Robert C. Ladner, Ijamsville; Robert E. Bird, Rockville; Karl Hardman, Chevy Chase, all of Md.

[73] Assignee: Enzon, Inc., South Plainfield, N.J.

[21] Appl. No.: 512,910

[22] Filed: Apr. 25, 1990

Related U.S. Application Data

[60] Division of Ser. No. 299,617, Jan. 19, 1989, Pat. No. 4,946,778, which is a continuation-in-part of Ser. No. 92,110, Sep. 21, 1987, abandoned, which is a continuation-in-part of Ser. No. 902,971, Sep. 2, 1986, abandoned.

[51] Int. Cl.⁵ ............... C12P 21/08; C07K 15/28; C12N 5/20; C12N 5/24
[52] U.S. Cl. ............... 435/172.3; 530/387.3; 530/388.1; 530/391.1; 530/391.3; 530/391.7; 424/85.8; 424/85.91; 435/69.6; 435/69.7; 435/240.27; 536/23.4; 536/23.53
[58] Field of Search ............... 530/387, 388, 389, 390, 530/391, 392, 393, 387.1, 387.3, 388.1, 389.1, 391.1, 391.3, 391.7, 413; 435/69.7, 70.21, 172.2, 172.3, 240.27, 240.2, 69.6, 252.3, 252.33, 320.1; 424/85.8, 85.91; 536/21, 23.4, 23.53

[56] References Cited

U.S. PATENT DOCUMENTS

| 4,507,234 | 3/1985 | Kato et al. | 530/388 |
| 4,638,049 | 1/1987 | Masuho et al. | 530/388 |
| 4,946,778 | 8/1990 | Ladner et al. | 435/69.7 |

OTHER PUBLICATIONS

Wood et al., *Nature*, 314:446 (1985).
Davies et al., *Ann. Rev. Immunol.*, 1:87 (1983).
Morrison, *Science*, 229:1202 (1985).
Neuberger et al., *Nature*, 312:604 (1984).
Goldenberg et al., Cancer Diagnosis and Therapy with Radiolabeled Antibodies, *Immunoconjugates, Antibody Conjugates in Radioimaging and Therapy of Cancer*, 259–280 (1987).
Vitetta et al., *Science*, 219:644 (1983).
Pastan et al., *Cell*, 47:641 (1986).

*Primary Examiner*—David L. Lacey
*Assistant Examiner*—Robert D. Budens
*Attorney, Agent, or Firm*—Jorge A. Goldstein

[57] ABSTRACT

The invention pertains to a single polypeptide chain binding molecule which has binding specificity and affinity substantially similar to the binding specificity and affinity of the light and heavy chain aggregate variable region of an antibody, to genetic sequences coding therefor, and to recombinant DNA methods of producing such molecule and uses for such molecule.

20 Claims, 55 Drawing Sheets

FIG. 21

```
Glu Val Gln Leu Val Glu Ser Gly Gly Asp Leu Val Lys Pro Gly Ser Leu Lys Leu
GAG GTG CAG CTG GTG GAG TCT GGG GGA GAC TTA GTG AAG CCT GGA TCC CTG AAA CTC
                    5                   10                  15                  20

Ser Cys Ala Ala Ser Gly Phe Thr Phe Ser Ile Tyr Gly Met Ser Trp Val Arg Gln Thr
TCC TGT GCA GCC TCT GGA TTC ACT TTC AGC TAT GGC ATG TCT TGG GTT CGC CAG ACT
                    25                  30                  35                  40

Pro Asp Lys Arg Leu Glu Leu Val Ala Thr Ile Ser Ser Gly Gly Thr Tyr Thr Tyr Tyr
CCA GAC AAG AGG CTG GAG CTG GTC GCA ACC ATT AGT AGT GGT GGT ACT TAC ACC TAT TAT
                    45                  50                  55                  60

Pro Asp Ser Val Lys Gly Arg Phe Thr Ile Ser Arg Asp Asn Ala Lys Asn Thr Leu Tyr
CCA GAT AGT GTG AAG GGG CGA TTC ACC ATC TCC AGA GAC AAT GCC AAG AAC ACC CTG TAC
                    65                  70                  75                  80

Leu Gln Met Ser Gly Leu Lys Ser Glu Asp Thr Ala Met Tyr Tyr Cys Ala Arg Arg Ile
CTG CAA ATG AGC AGT CTG AAG TCT GAG GAC ACA GCC ATG TAT TAC TGT GCA AGA CGG ATT
                    85                  90                  95                  100

Thr Thr Val Val Leu Thr Asp Tyr Tyr Ala Met Asp Tyr Trp Gly Gln Gly Thr Ser Val
ACG GTA GTA CTT ACG GAT TAC TAT GCT ATG GAC TAC TGG GGT CAA GGA ACC TCA GTC
                    105                 110                 115                 120

Thr Val Ser Ser Ala Lys Thr Thr Pro Pro Ser Val Tyr Pro Leu Ala Pro Gly Ser Ala
ACC GTC TCC TCA GCC AAA ACG ACA CCC CCA TCT GTC TAT CCA CTG GCC CCT GGA TCT GCT
                    125                 130                 135                 140

Ala Gln Thr Asn Ser Met Val Thr Leu Gly Cys Leu Val Lys Gly Tyr Phe Pro Glu Pro
GCC CAA ACT AAC TCC ATG GTG ACC CTG GGA TGC CTG GTC AAG GGC TAT TTC CCT GAG CCA
                    145                 150                 155                 160

Val Thr Val Thr Trp Asn Ser Gly Ser Leu Ser Ser Gly Val His Thr Phe Pro Ala Val
GTG ACA GTG ACC TGG AAC TCT GGA TCC CTG TCC AGC GGT GTG CAC ACC TTC CCA GCT GTC
                    165                 170                 175                 180

Leu Gln Ser Asp Leu Tyr Thr Leu Ser Ser Val Thr Val Pro Ser Ser Thr Trp Pro
CTG CAG TCT GAC CTC TAC ACT CTG AGC AGC TCA GTG ACT GTC CCC TCC AGC ACC TGG CCC
                    185                 190                 195                 200

Ser Glu Thr Val Thr Cys Asn Val Ala His Pro Ala Ser Ser Thr Lys Val Asp Lys Lys
AGC GAG ACC GTC ACC TGC AAC GTT GCC CAC CCG GCC AGC AGC ACC AAG GTG GAC AAG AAA
                    205                 210                 215                 220

Ile Val Pro Arg Asp Cys Gly Cys Lys Pro Cys Ile Cys Thr Val Pro Glu Val Ser Ser
ATT GTG CCC AGG GAT TGT GGT TGT AAG CCT TGC ATA TGT ACA GTC CCA GAA GTA TCA TCT
                    225                 230                 235                 240
```

| | | | | 245 Pro CCA | Pro Lys CCC AAG | 250 Asp GAT | Val Leu Thr CTC ACC | Ile ATT | 255 Thr ACT | Leu Pro Lys CTG CCT AAG | 260 Val GTC |
|---|---|---|---|---|---|---|---|---|---|---|---|

Val Phe Ile Phe
GTC TTC ATC TTC
245 Pro Pro Lys Asp Val Leu Thr Ile 255 Thr Leu Pro Lys 260 Val
CCC CCA AAG GAT GTG CTC ACC ATT ACT CTG CCT AAG GTC
265 270 280
Thr Cys Val Val Asp Ile Ser Lys Asp Glu Val Gln Phe Ser Trp Phe Val
ACG TGT GTT GTG GAC ATC AGC AAG GAT GAG GTC CAG TTC AGC TGG TTT GTA
285 290 295 300
Asp Asp Val Glu Val His Thr Ala Gln Thr Gln Pro Arg Glu Gln Phe Asn Ser Thr
GAT GTG GAG CTG CAC ACA GCT CAG ACG CAG CCC CGG GAG GAG CAG TTC AAC AGC ACT
305 310 315 320
Ser Arg Ser Val Ser Glu Leu Pro Ile Met His Gln Asp Trp Leu Asn Gly Lys Glu Phe
TCC TCA GTC AGT GAA CTT CCC ATC ATG CAC CAG GAC TGG CTC AAT GGC AAG GAG TTC
325 330 335 340
Lys Cys Arg Val Asn Ser Ala Ala Phe Pro Ala Pro Ile Glu Lys Thr Ile Ser Lys Thr
AAA TGC AGG GTC AAC AGT GCA GCT TTC CCT GCC CCC ATC GAG AAA ACC ATC TCC AAA ACC
345 350 355 360
Lys Gly Arg Pro Lys Ala Pro Gln Val Tyr Thr Ile Pro Pro Pro Lys Glu Gln Met Ala
AAA GGC AGA CCG AAG GCT CCA CAG GTG TAC ACC ATT CCA CCT CCC AAG GAG CAG ATG GCC
365 370 375 380
Lys Asp Lys Val Ser Leu Thr Cys Met Ile Thr Asp Phe Phe Pro Glu Asp Ile Thr Val
AAG GAT AAA GTC AGT CTG ACC TGC ATG ATA ACA GAC TTC TTC CCT GAA GAC ATT ACT GTG
385 390 395 400
Glu Trp Gln Trp Asn Gly Gln Pro Ala Glu Asn Tyr Lys Asn Thr Gln Pro Ile Met Asn
GAG TGG CAG TGG AAT GGG CAG CCA GCG GAG AAC TAC AAG AAC ACT CAG CCC ATC ATG AAC
405 410 415 420
Thr Asn Gly Ser Tyr Phe Val Tyr Ser Lys Leu Asn Val Gln Lys Ser Asn Trp Glu Ala
ACG AAT GGC TCT TAC TTC GTC TAC AGC AAG CTC AAT GTG CAG AAG AGC AAC TGG GAG GCA
425 430 435 440
Gly Asn Thr Phe Thr Cys Ser Val Leu His Glu Gly Leu His Asn His His Thr Glu Lys
GGA AAT ACT TTC ACC TGC TCT GTG TTA CAT GAG GGC CTG CAC AAC CAC CAT ACT GAG AAG
445
Ser Leu Ser His Ser Pro Gly Lys ***
AGC CTC TCC CAC TCT CCT GGT AAA TGA

FIG. 21 (cont.)

| | | | | | 5 | | | | | 10 | | | | | 15 | | | | | 20 |
|---|---|---|---|---|---|---|---|---|---|---|---|---|---|---|---|---|---|---|---|---|
| Glu | Asn | Val | Thr | Leu | Thr | Gln | Ser | Pro | Ala | Ile | Met | Ser | Ala | Ser | Pro | Gly | Glu | Lys | VAL | Thr |
| GAA | AAT | GTG | ACC | CTC | ACC | CAG | TCT | CCA | GCA | ATC | ATG | TCT | GCA | TCT | CCA | GGG | GAA | AAG | GTC | ACC |
| | | | | 25 | | | | | 30 | | | | | 35 | | | | | 40 | |
| Met | Thr | Cys | Arg | Ala | Ser | Ser | Ser | Val | Ser | Tyr | Leu | His | Trp | Phe | Gln | Gln | Lys | | | |
| ATG | ACC | TGC | AGG | GCC | AGC | TCA | AGT | GTA | AGT | TAC | TTG | CAC | TGG | TTC | CAG | CAG | AAG | | | |
| | | | | 45 | | | | | 50 | | | | | 55 | | | | | 60 | |
| Ser | Gly | Ala | Ser | Pro | Lys | Leu | Trp | Ile | Tyr | Ser | Thr | Ser | Asn | Leu | Ala | Ser | Gly | Val | Pro | |
| TCA | GGT | GCC | TCC | CCC | AAA | CTC | TGG | ATT | TAT | AGC | ACA | TCC | AAC | TTG | GCT | TCT | GGA | GTC | CCT | |
| | | | | 65 | | | | | 70 | | | | | 75 | | | | | 80 | |
| Ala | Arg | Phe | Ser | Gly | Ser | Gly | Ser | Gly | Thr | Ser | Tyr | Ser | Leu | Thr | Ile | Ser | Ser | Val | Glu | |
| GCT | CGC | TTC | AGT | GGC | AGT | GGG | TCT | GGG | ACC | TCT | TAC | TCT | CTC | ACA | ATC | AGC | AGT | GTG | GAG | |
| | | | | 85 | | | | | 90 | | | | | 95 | | | | | 100 | |
| Ala | Glu | Asp | Ala | Ala | Thr | Tyr | Tyr | Cys | Gln | Gln | Tyr | Ser | Gly | Tyr | Pro | Leu | Thr | Phe | Gly | |
| GCT | GAA | GAT | GCT | GCC | ACT | TAT | TAC | TGC | CAG | CAG | TAC | AGT | GGT | TAC | CCA | CTC | ACG | TTC | GGT | |
| | | | | 105 | | | | | 110 | | | | | 115 | | | | | 120 | |
| Ala | Gly | Thr | Lys | Leu | Glu | Leu | Lys | Arg | Ala | Asp | Ala | Ala | Pro | Thr | Val | Ser | Ile | Phe | Pro | |
| GCT | GGG | ACC | AAG | CTG | GAG | CTG | AAA | CGG | GCT | GAT | GCT | GCA | CCA | ACT | GTA | TCC | ATC | TTC | CCA | |
| | | | | 125 | | | | | 130 | | | | | 135 | | | | | 140 | |
| Pro | Ser | Ser | Glu | Gln | Leu | Thr | Ser | Gly | Gly | Ala | Ser | Val | Val | Cys | Phe | Leu | Asn | Asn | Phe | |
| CCA | TCC | AGT | GAG | CAG | TTA | ACA | TCT | GGA | GGT | GCC | TCA | GTC | GTG | TGC | TTC | TTG | AAC | AAC | TTC | |
| | | | | 145 | | | | | 150 | | | | | 155 | | | | | 160 | |
| Tyr | Pro | Lys | Asp | Ile | Asn | Val | Lys | Trp | Lys | Ile | Asp | Gly | Ser | Glu | Arg | Gln | Asn | Gly | Val | |
| TAC | CCC | AAA | GAC | ATC | AAT | GTC | AAG | TGG | AAG | ATT | GAT | GGC | AGT | GAA | CGA | CAA | AAT | GGC | GTC | |
| | | | | 165 | | | | | 170 | | | | | 175 | | | | | 180 | |
| Leu | Asn | Ser | Trp | Thr | Asp | Gln | Asp | Ser | Lys | Asp | Ser | Thr | Tyr | Ser | Met | Ser | Ser | Thr | Leu | |
| CTG | AAC | AGT | TGG | ACT | GAT | CAG | GAC | AGC | AAA | GAC | AGC | ACC | TAC | AGC | ATG | AGC | AGC | ACC | CTC | |
| | | | | 185 | | | | | 190 | | | | | 195 | | | | | 200 | |
| Thr | Leu | Thr | Lys | Asp | Glu | Tyr | Glu | Arg | His | Asn | Ser | Tyr | Thr | Cys | Glu | Ala | Thr | His | Lys | |
| ATG | TTG | ACC | AAG | GAC | GAG | TAT | GAA | CGA | CAT | AAC | AGC | TAT | ACC | TGT | GAG | GCC | ACT | CAC | AAG | |
| | | | | 205 | | | | | 210 | | | | | 215 | | | | | | |
| Thr | Ser | Thr | Ser | Pro | Ile | Val | Lys | Ser | Phe | Asn | Arg | Asn | Glu | Cys | *** | | | | | |
| ACA | TCA | ACT | TCA | CCC | ATT | GTC | AAG | AGC | TTC | AAC | AGG | AAT | GAG | TGT | TAG | | | | | |

FIG. 22

| | | | | | 5 | | | | | 10 | | | | | 15 | | | | | 20 |
|---|---|---|---|---|---|---|---|---|---|---|---|---|---|---|---|---|---|---|---|---|
| Met | Glu | Asn | Val | Leu | Thr | Gln | Ser | Pro | Ala | Ile | Met | Ser | Ala | Ser | Pro | Gly | Glu | Lys | Val |
| ATG | GAA | AAT | GTG | CTC | ACC | CAG | TCT | CCA | GCA | ATC | ATG | TCT | GCA | TCT | CCA | GGG | GAA | AAG | GTC |
| | | | | 25 | | | | | 30 | | | | | 35 | | | | | 40 | |
| Thr | Met | Thr | Cys | Arg | Ala | Ser | Ser | Val | Ser | Ser | Tyr | Leu | His | Trp | Phe | Gln | Gln |
| ACC | ATG | ACC | TGC | AGG | GCC | AGC | TCA | AGT | GTA | AGT | TAC | TTG | CAC | TGG | TTC | CAG | CAG |
| | | | | 45 | | | | | 50 | | | | | 55 | | | | | 60 |
| Lys | Ser | Ile | Ala | Phe | Ala | Ser | Asn | Gly | Asp | Leu | Val | Lys | Pro | Gly | Ser | Leu |
| AAG | TCA | ATC | GCG | TTC | GCG | AGC | AAC | GGG | GAC | TTA | GTG | AAG | CCT | GGA | TCC | CTG |
| | | | | 65 | | | | | 70 | | | | | 75 | | | | | 80 |
| Lys | Leu | Ser | Cys | Ala | Ala | Ser | Gly | Phe | Thr | Phe | Ile | Ser | Tyr | Gly | Met | Ser | Trp | Val | Arg |
| AAA | CTC | TCC | TGT | GCA | GCC | TCT | GGA | TTC | ACT | TTC | ATT | AGC | TAT | GGC | ATG | TCT | TGG | GTT | CGC |
| | | | | 85 | | | | | 90 | | | | | 95 | | | | | 100 |
| Gln | Thr | Pro | Asp | Lys | Arg | Leu | Glu | Trp | Val | Ala | Thr | Ile | Ser | Ser | Gly | Ser | Thr | Tyr | Thr |
| CAG | ACT | CCA | GAC | AAG | AGG | CTG | GAG | TGG | GTC | GCA | ACC | ATT | AGT | AGT | GGT | AGT | ACT | TAC | ACC |
| | | | | 105 | | | | | 110 | | | | | 115 | | | | | 120 |
| Tyr | Tyr | Pro | Asp | Ser | Val | Lys | Gly | Arg | Phe | Thr | Ile | Ser | Arg | Asp | Asn | Ala | Lys | Asn | Thr |
| TAC | TAT | CCA | GAC | AGT | GTG | AAG | GGG | CGA | TTC | ACC | ATC | TCC | AGA | GAC | AAT | GCC | AAG | AAC | ACC |
| | | | | 125 | | | | | 130 | | | | | 135 | | | | | 140 |
| Leu | Tyr | Leu | Gln | Met | Ser | Gly | Leu | Thr | Ser | Glu | Asp | Thr | Ala | Met | Tyr | Tyr | Cys | Ala | Arg |
| CTG | TAC | CTG | CAA | ATG | AGC | GGT | CTG | ACG | TCT | GAG | GAC | ACA | GCC | ATG | TAT | TAC | TGT | GCA | AGA |
| | | | | 145 | | | | | 150 | | | | | 155 | | | | | 160 |
| Arg | Ile | Thr | Thr | Val | Leu | Val | Thr | Leu | Thr | Ser | Tyr | Ala | Met | Asp | Tyr | Trp | Gly | Gln | Ser |
| CGG | ATT | ACT | ACG | GTA | CTT | GTA | ACG | CTT | ACG | TCT | TAT | GCT | ATG | GAC | TAC | TGG | GGT | CAA | TCT |
| | | | | 165 | | | | | 170 | | | | | 175 | | | | | 180 |
| Pro | Lys | Leu | Trp | Ile | Tyr | Ser | Thr | Ser | Asn | Leu | Ala | Ser | Gly | Val | Pro | Ala | Arg | Phe | Ser |
| CCC | AAA | CTC | TGG | ATT | TAT | AGC | ACA | TCC | AAC | TTG | GCT | TCT | GGA | GTC | CCT | GCT | CGC | TTC | AGT |
| | | | | 185 | | | | | 190 | | | | | 195 | | | | | 200 |
| Gly | Ser | Gly | Ser | Gly | Thr | Ser | Tyr | Ser | Leu | Thr | Ile | Ser | Ser | Val | Glu | Ala | Glu | Asp | Ala |
| GGT | AGT | GGG | TCT | GGG | ACC | TCT | TAC | TCT | CTC | ACA | ATC | AGC | AGT | GTG | GAG | GCT | GAA | GAT | GCT |
| | | | | 205 | | | | | 210 | | | | | 215 | | | | | 220 |
| Ala | Thr | Tyr | Tyr | Cys | Gln | Gln | Tyr | Ser | Gly | Tyr | Pro | Leu | Thr | Phe | Gly | Ala | Gly | Thr | Lys |
| GCC | ACT | TAT | TAC | TGC | CAG | CAG | TAC | AGT | GGT | TAC | CCA | CTC | ACG | TTC | GGT | GCT | GGG | ACC | AAG |
| | | | | 225 | | | | |
| Leu | Glu | Leu | Lys | Arg | *** |
| CTG | GAG | CTG | AAA | CGG | TAA |

FIG. 24

| Pos | AA | Codon | Pos | AA | Codon | Pos | AA | Codon | Pos | AA | Codon |
|---|---|---|---|---|---|---|---|---|---|---|---|
| 1 | Met | ATG | 2 | Glu | GAA | 3 | Asn | AAT | 4 | Val | GTG |
| 5 | Leu | CTC | 6 | Thr | ACC | 7 | Gln | CAG | 8 | Ser | TCT |
| 9 | Pro | CGA | 10 | Ala | GCA | 11 | Ile | ATC | 12 | Met | ATG |
| 13 | Ser | TCT | 14 | Ala | GCA | 15 | Ser | TCT | 16 | Pro | CCA |
| 17 | Gly | GGG | 18 | Glu | GAA | 19 | Lys | AAG | 20 | Val | GTC |
| 21 | Thr | ACC | 22 | Met | ATG | 23 | Cys | TGC | 24 | Arg | AGG |
| 25 | Ser | AGC | 26 | Ala | GCC | 27 | Ser | TCC | 28 | Val | GTA |
| 29 | Ser | AGT | 30 | Ser | TCA | 31 | Tyr | TAC | 32 | Leu | TTG |
| 33 | His | CAC | 34 | Trp | TGG | 35 | Phe | TTC | 36 | Gln | CAG |
| 41 | Lys | AAG | 42 | Ser | TCA | 43 | Gly | GGT | 44 | Ala | GCC |
| 45 | Ser | TCC | 46 | Pro | CCC | 47 | Lys | AAA | 48 | Leu | CTC |
| 49 | Trp | TGG | 50 | Ile | ATT | 51 | Tyr | TAT | 52 | Ser | AGC |
| 53 | Thr | ACA | 54 | Ser | TCC | 55 | Asn | AAC | 56 | Leu | — |
| 57 | Ala | GCT | 58 | Ser | TCT | 59 | Gly | GGA | 60 | Val | GTC |
| 61 | Pro | CCT | 62 | Ala | GCT | 63 | Arg | CGC | 64 | Phe | TTC |
| 65 | Ser | AGT | 66 | Gly | GGC | 67 | Ser | AGT | 68 | Gly | GGG |
| 69 | Tyr | TAT | 70 | Gly | GGG | 71 | Thr | ACC | 72 | Ser | TCT |
| 73 | Tyr | TAT | 74 | Thr | ACA | 75 | Ser | TCT | 76 | Leu | CTC |
| 77 | Thr | ACT | 78 | Ile | ATC | 79 | Ser | AGC | 80 | Val | GTG |
| 81 | Glu | GAG | 82 | Ala | GCT | 83 | Glu | GAA | 84 | Asp | GAT |
| 85 | Ala | GCT | 86 | Ala | GCA | 87 | Thr | ACT | 88 | Tyr | TAC |
| 89 | Tyr | TAT | 90 | Cys | TGC | 91 | Gln | CAG | 92 | Gln | CAG |
| 93 | Tyr | TAT | 94 | Ser | AGT | 95 | Gly | GGT | 96 | Tyr | TAC |
| 97 | Pro | CCA | 98 | Leu | CTC | 99 | Thr | ACG | 100 | Phe | TTC |
| 101 | Gly | GGT | 102 | Ala | GCT | 103 | Gly | GGT | 104 | Thr | ACC |
| 105 | Lys | AAG | 106 | Val | GTT | 107 | Arg | CGT | 108 | Gly | — |
| 109 | Ala | GCA | 110 | Pro | CCG | 111 | Ala | GCA | 112 | Ile | ATC |
| 113 | Asn | AAC | 114 | Val | GTA | 115 | Ala | GCT | 116 | His | CAC |
| 117 | Val | GTA | 118 | Phe | TTC | 119 | Ser | TCT | 120 | Ser | TCT |
| 121 | Gly | GGG | 122 | Gly | GGA | 123 | Asp | GAC | 124 | Leu | TTA |
| 125 | Val | GTG | 126 | Lys | AAG | 127 | Pro | CCT | 128 | Gly | GGA |
| 129 | Ser | TCT | 130 | Ser | TCC | 131 | Leu | CTC | 132 | Lys | AAA |
| 133 | Leu | CTG | 134 | Ser | TCC | 135 | Cys | TGT | 136 | Ala | GCA |
| 137 | Ala | GCA | 138 | Ser | TCT | 139 | Gly | GGA | 140 | Phe | TTC |
| 141 | Thr | ACT | 142 | Phe | TTC | 143 | Ile | ATT | 144 | Ser | AGC |
| 145 | Tyr | TAT | 146 | Gly | GGC | 147 | Met | ATG | 148 | Ser | TCT |
| 149 | Trp | TGG | 150 | Val | GTT | 151 | Arg | CGC | 152 | Gln | CAG |
| 153 | Thr | ACT | 154 | Pro | CCA | 155 | Leu | CTC | 156 | Ser | TCC |
| 157 | Asp | GAC | 158 | Pro | CCA | 159 | Thr | ACT | 160 | Trp | TGG |
| 161 | Val | GTC | 162 | Ala | GCA | 163 | Thr | ACC | 164 | Ile | ATT |
| 165 | Tyr | TAT | 166 | Ser | AGT | 167 | Gly | GGT | 168 | Ser | AGT |
| 169 | Thr | ACT | 170 | Tyr | TAC | 171 | Tyr | TAT | 172 | Pro | CCA |
| 173 | Tyr | TAC | 174 | Asp | GAC | 175 | Tyr | TAT | 176 | Pro | CCA |
| 177 | Asp | GAC | 178 | Tyr | TAC | 179 | Arg | CGA | 180 | Arg | CGA |
| 181 | Phe | TTC | 182 | Thr | ACC | 183 | Ile | ATC | 184 | Ser | TCC |
| 185 | Ser | AGT | 186 | Arg | AGA | 187 | Asp | GAC | 188 | Asn | AAT |
| 189 | Ala | GCC | 190 | Asn | AAC | 191 | Thr | ACC | 192 | Leu | CTG |
| 193 | Tyr | TAC | 194 | Leu | CTG | 195 | Gln | CAA | 196 | Met | ATG |
| 197 | Ser | AGC | 198 | Gly | GGT | 199 | Leu | CTG | 200 | Lys | AAG |
| 201 | Ser | TCT | 202 | Glu | GAG | 203 | Asp | GAC | 204 | Thr | ACA |
| 205 | Ala | GCA | 206 | Met | ATG | 207 | Tyr | TAT | 208 | Tyr | TAC |
| 209 | Cys | TGT | 210 | Ala | GCA | 211 | Arg | AGA | 212 | Ile | ATT |
| 213 | Thr | ACT | 214 | Thr | ACG | 215 | Gln | CAA | 216 | Met | ATG |
| 217 | Ser | AGC | 218 | Gly | GGT | 219 | Leu | CTG | 220 | Lys | AAG |
| 221 | Tyr | TAC | 222 | Tyr | TAT | 223 | Ala | GCT | 224 | Met | ATG |
| 225 | Asp | GAC | 226 | Thr | ACA | 227 | Ala | GCA | 228 | Met | ATG |
| 229 | Tyr | TAC | 230 | Gly | GGA | 231 | Thr | ACC | 232 | Ser | TCA |
| 233 | Val | GTC | 234 | Thr | ACC | 235 | Val | GTA | 236 | Leu | CTT |
| | Thr | ACG | | Asp | GAT | | Ser | TCC | *** | | TAA |

| # | AA | Codon | # | AA | Codon | # | AA | Codon | # | AA | Codon |
|---|----|-------|---|----|-------|---|----|-------|---|----|-------|
| 1 | Met | ATG | 2 | Glu | GAA | 3 | Asn | AAT | 4 | Val | GTG |
| 5 | Leu | CTC | 6 | Thr | ACC | 7 | Gln | CAG | 8 | Ser | TCT |
| 9 | Pro | CGA | 10 | Ala | GCA | 11 | Ile | ATC | 12 | Met | ATG |
| 13 | Ser | TCT | 14 | Ala | GCA | 15 | Ser | TCT | 16 | Pro | CCA |
| 17 | Gly | GGG | 18 | Glu | GAA | 19 | Lys | AAG | 20 | Val | GTC |
| 21 | Thr | ACC | 22 | Met | ATG | 23 | Thr | ACC | 24 | Cys | TGC |
| 25 | Arg | AGG | 26 | Ala | GCC | 27 | Ser | AGC | 28 | Ala | GCC |
| 29 | Ser | TCA | 30 | Ser | AGT | 31 | Ser | TCC | 32 | Val | GTA |
| 33 | Ser | AGT | 34 | Tyr | TAC | 35 | Leu | TTG | 36 | His | CAC |
| 37 | Trp | TGG | 38 | Phe | TTC | 39 | Gln | CAG | 40 | Gln | CAG |
| 41 | Lys | AAA | 42 | Pro | CCC | 43 | Ser | TCC | 44 | Gly | GCC |
| 45 | Ala | GCC | 46 | Ser | TCC | 47 | Pro | CCC | 48 | Lys | AAA |
| 49 | Leu | CTC | 50 | Trp | TGG | 51 | Ile | ATT | 52 | Tyr | TAT |
| 53 | Ser | AGT | 54 | Thr | ACA | 55 | Ser | TCC | 56 | Asn | AAC |
| 57 | Leu | TTC | 58 | Ala | GCT | 59 | Ser | TCT | 60 | Gly | GGA |
| 61 | Val | GTC | 62 | Pro | CCT | 63 | Ala | GCT | 64 | Arg | CGC |
| 65 | Phe | TTC | 66 | Ser | AGT | 67 | Gly | GGT | 68 | Ser | TCT |
| 69 | Gly | GGG | 70 | Ser | AGT | 71 | Gly | GGT | 72 | Thr | ACA |
| 73 | Ser | TCT | 74 | Tyr | TAC | 75 | Ser | AGC | 76 | Leu | CTC |
| 77 | Thr | ACG | 78 | Ile | ATC | 79 | Ser | AGT | 80 | Ser | AGT |
| 81 | Val | GTG | 82 | Glu | GAA | 83 | Ala | GCT | 84 | Glu | GAA |
| 85 | Ala | GCT | 86 | Asp | GAT | 87 | Ala | GCT | 88 | Ala | GCT |
| 89 | Thr | ACT | 90 | Tyr | TAC | 91 | Tyr | TAC | 92 | Cys | TGC |
| 93 | Gln | CAG | 94 | Gln | CAG | 95 | Tyr | TAT | 96 | Pro | CCA |
| 97 | Leu | CTC | 98 | Thr | ACG | 99 | Phe | TTT | 100 | Phe | TTC |
| 101 | Gly | GGT | 102 | Ala | GCT | 103 | Gly | GGG | 104 | Thr | ACC |
| 105 | Lys | AAG | 106 | Leu | CTG | 107 | Lys | AAA | 108 | Glu | GAA |
| 109 | Ser | TCT | 110 | Val | GTT | 111 | Ser | TCT | 112 | Gly | GGG |
| 113 | Gln | CAG | 114 | Leu | CTG | 115 | Glu | GAA | 116 | Ala | GCT |
| 117 | Gly | GGG | 118 | Gln | CAG | 119 | Phe | TTT | 120 | Phe | TTT |
| 121 | Val | GTG | 122 | Gln | CAG | 123 | Leu | CTG | 124 | Val | GTG |
| 125 | Val | GTG | 126 | Gln | CAG | 127 | Leu | CTG | 128 | Val | GTG |
| 129 | Ser | TCT | 130 | Gly | GGG | 131 | Gly | GGG | 132 | Asp | GAC |
| 133 | Leu | TTA | 134 | Val | GTG | 135 | Val | GTG | 136 | Lys | AAG |
| 137 | Pro | CCT | 138 | Gly | GGA | 139 | Gly | GGG | 140 | Ser | TCC |
| 141 | Arg | CGT | 142 | Ser | TCT | 143 | Leu | CTG | 144 | Asp | GAT |
| 145 | Ala | GCA | 146 | Ala | GCC | 147 | Ser | TCT | 148 | Gly | GGA |
| 149 | Phe | TTC | 150 | Thr | ACT | 151 | Phe | TTC | 152 | Ile | ATT |
| 153 | Ser | AGC | 154 | Tyr | TAT | 155 | Gly | GGC | 156 | Met | ATG |
| 157 | Ser | TCT | 158 | Trp | TGG | 159 | Val | GTT |  |  |  |

| 160 | Leu | CTG | 161 | Lys | AAA | 162 | Leu | CTC | 163 | Ser | TCC | 164 | Cys | TGT |

| Pos | | | | 165 | | | | 170 | | | | | 175 | | | | 180 |
|---|---|---|---|---|---|---|---|---|---|---|---|---|---|---|---|---|---|
| Arg | Gln | Thr | Pro | Asp | Lys | Arg | Leu | Glu | Val | Ala | Thr | Ile | Ser | Gly | Ser | Thr | Tyr |
| CGC | CGA | ACT | CCA | GAC | AAG | AGG | CTG | GAG | GTC | GCA | ACC | ATT | AGT | GGT | AGT | ACT | TAC |

| | | | | 185 | | | | 190 | | | | | 195 | | | | | 200 | |
|---|---|---|---|---|---|---|---|---|---|---|---|---|---|---|---|---|---|---|---|
| Thr | Tyr | Tyr | Pro | Asp | Ser | Val | Lys | Gly | Arg | Phe | Thr | Ile | Ser | Arg | Asp | Asn | Ala | Lys | Asn |
| ACC | TAT | TAT | CCA | GAC | AGT | GTG | AAG | GGG | CGA | TTC | ACC | ATC | TCC | AGA | GAC | AAT | GCC | AAG | AAC |

| | | | | 205 | | | | 210 | | | | | 215 | | | | | 220 |
|---|---|---|---|---|---|---|---|---|---|---|---|---|---|---|---|---|---|---|
| Thr | Leu | Tyr | Leu | Gln | Met | Ser | Gly | Leu | Lys | Ser | Glu | Asp | Thr | Ala | Met | Tyr | Cys | Ala |
| ACC | CTG | TAC | CTG | CAA | ATG | AGC | GGT | CTG | AAG | TCT | GAG | GAC | ACA | GCC | ATG | TAT | TGT | GCA |

| | | | | 225 | | | | 230 | | | | | 235 | | | | | 240 |
|---|---|---|---|---|---|---|---|---|---|---|---|---|---|---|---|---|---|---|
| Arg | Arg | Ile | Thr | Thr | Val | Val | Leu | Thr | Asp | Tyr | Tyr | Ala | Met | Asp | Tyr | Trp | Gly | Gln |
| AGA | CGG | ATT | ACT | ACG | GTA | CTT | ACG | GAT | TAC | TAT | GCT | ATG | GAC | TAC | TGG | GGT | CAA | GGA |

| | | | | 245 | | | |
|---|---|---|---|---|---|---|---|
| Thr | Ser | Val | Thr | Val | Ser | *** | |
| ACC | TCA | GTC | ACC | GTC | TCC | TAA | |

| # | AA | Codon | # | AA | Codon | # | AA | Codon | # | AA | Codon |
|---|----|----|---|----|----|---|----|----|---|----|----|
| 1 | Met | ATG | 36 | Trp | TGG | 71 | Thr | ACC | 106 | Thr | ACT |
| 2 | Glu | GAA | 37 | Phe | TTC | 72 | Ser | TCT | 107 | Leu | CTG |
| 3 | Asn | AAT | 38 | Gln | CAG | 73 | Leu | CTC | 108 | Ser | TCT |
| 4 | Val | GTG | 39 | Gln | CAG | 74 | Thr | ACA | 109 | Pro | CCA |
| 5 | Leu | CTC | 40 | Lys | AAG | 75 | Ile | ATC | 110 | Gly | GGT |
| 6 | Thr | ACC | 41 | Pro | CCT | 76 | Ser | AGC | 111 | Ala | GCA |
| 7 | Gln | CAG | 42 | Ala | GCT | 77 | Ser | AGT | 112 | Asp | GAT |
| 8 | Ser | TCT | 43 | Arg | CGC | 78 | Val | GTG | 113 | Lys | AAA |
| 9 | Pro | CCA | 44 | Phe | TTC | 79 | Ser | AGT | 114 | Thr | ACT |
| 10 | Ala | GCA | 45 | Ser | TCC | 80 | Val | GTG | 115 | Ala | GCA |
| 11 | Ile | ATC | 46 | Gly | GGT | 81 | Gly | GGT | 116 | Gly | GGT |
| 12 | Met | ATG | 47 | Ser | AGT | 82 | Ser | TCT | 117 | Tyr | TAC |
| 13 | Ser | TCT | 48 | Gly | GGG | 83 | Tyr | TAC | 118 | Pro | CCA |
| 14 | Ala | GCA | 49 | Ser | TCT | 84 | Tyr | TAC | 119 | Leu | CTC |
| 15 | Ser | TCT | 50 | Val | GTA | 85 | Thr | ACT | 120 | Val | GTG |
| 16 | Pro | CCA | 51 | Ser | AGT | 86 | Ala | GCT | 121 | Ala | GCA |
| 17 | Gly | GGG | 52 | Ser | TCA | 87 | Ala | GCT | 122 | Leu | CTG |
| 18 | Glu | GAA | 53 | Ser | TCC | 88 | Leu | CTG | 123 | Ser | TCT |
| 19 | Lys | AAG | 54 | Ala | GCA | 89 | Thr | ACT | 124 | Asn | AAC |
| 20 | Val | GTC | 55 | Asn | AAC | 90 | Cys | TGC | 125 | Val | GTT |
| 21 | Thr | ACC | 56 | Leu | TTG | 91 | Gln | CAG | 126 | Leu | CTG |
| 22 | Met | ATG | 57 | Ala | GCT | 92 | Gln | CAG | 127 | Thr | ACT |
| 23 | Cys | TGC | 58 | Ser | TCT | 93 | Tyr | TAC | 128 | Asp | GAT |
| 24 | Arg | AGG | 59 | Gly | GGA | 94 | Ser | AGT | 129 | Lys | AAA |
| 25 | Ala | GCC | 60 | Val | GTC | 95 | Gly | GGT | 130 | Val | GTT |
| 26 | Ser | AGC | 61 | Pro | CCT | 96 | Tyr | TAC | 131 | Gly | GGC |
| 27 | Ser | TCA | 62 | Ala | GCT | 97 | Pro | CCA | 132 | Gln | CAG |
| 28 | Ser | AGT | 63 | Arg | CGC | 98 | Tyr | TAC | 133 | Leu | CTG |
| 29 | Ser | AGT | 64 | Phe | TTC | 99 | Thr | ACA | 134 | Val | GTG |
| 30 | Val | GTA | 65 | Ser | TCC | 100 | Phe | TTC | 135 | Glu | GAG |
| 31 | Ser | AGT | 66 | Gly | GGT | 101 | Gly | GGG | 136 | Ser | TCT |
| 32 | Ser | TCC | 67 | Ser | AGT | 102 | Ala | GCT | 137 | Gly | GGA |
| 33 | Tyr | TAT | 68 | Gly | GGG | 103 | Gly | GGT | 138 | Asp | GAC |
| 34 | Leu | CTC | 69 | Ser | TCT | 104 | Thr | ACC | 139 | Leu | TTA |
| 35 | His | CAT | 70 | Gly | GGG | 105 | Lys | AAG | 140 | Val | GTG |

FIG. 33 (cont.)

```
            Pro Gly Ser     Leu Lys Ser Cys     Ala Ser Gly Phe     Thr Phe Ile Ser Tyr     Gly
            CCT GGA TCC     CTG AAA TCC TGT     GCA TCT GGA TTC     ACT TTC ATT AGC TAT     GGC
                        145                 150                 155                     160

Met Ser Trp Val     Arg Gln Thr Pro Asp     Lys Arg Leu Glu Trp     Val Ala Thr Ile Ser     Ser
            ATG TCT TGG GTT     CGC CAG ACT CCA GAC     AAG AGG CTG GAG TGG     GTC GCA ACC ATT AGT     AGT
                            165                     170                     175                     180

Gly Ser Thr Tyr     Tyr Tyr Pro Asp     Ser Val Lys Gly     Phe Thr Ile Ser Arg     Asp
            GGT AGT ACT TAC     TAT TAC CCA GAC     AGT GTG AAG GGG     TTC ACC ATC TCC CGA     GAC
                            185                 190                 195                     200

Asn Ala Lys Asn     Arg Ile Thr Leu Gln     Met Ser Gly Leu     Ser Leu Lys Glu Asp Thr     Ala Met
            AAT GCC AAG AAC     CGG ATT ACT CTG CAA     ATG AGC GGT CTG     TCT CTT AAG GAG GAC ACA     GCC ATG
                            205                     210                 215                         220

Tyr Cys Ala Arg     Arg Ile Thr     Leu Gln     Ser Gly     Leu Lys     Thr Asp     Leu Val     Tyr Ala Met Asp     Tyr
            TAT TGT GCA AGA     CGG ATT ACT     CTG CAA     TCT GGT     CTG AAG     ACG GAT     CTT GTA     TAT GCT ATG GAC     TAC
                            225                     230                                                 235                     240

Trp Gly Gln Gly     Thr Ser Val Thr Val     Ser ***
            TGG GGT CAA GGA     ACC TCA GTC ACC GTC     TCC TAA
                            245                         250
```

```
                  5                    10                   15                   20
Met Glu Asn Val Leu Thr Gln Ser Pro Ala Ile Met Ser Ala Ser Pro Gly Glu Lys Val
ATG GAA AAT GTG CTC ACC CAG TCT CCA GCA ATC ATG TCT GCA TCT CCA GGG GAA AAG GTC 25                   30                   35                   40
Thr Met Thr Cys Arg Ala Ser Ser Ser Val Ser Ser Tyr Leu His Trp Tyr Gln Gln
ACC ATG ACC TGC AGG GCC AGC TCA AGT GTA AGT TAC TTG CAC TGG TAC CAG CAG 45                   50                   55                   60
Lys Ser Gly Ala Ser Pro Lys Leu Trp Val Tyr Gly Thr Ser Asn Leu Ala Ser Gly Val
AAG TCA GGT GCC TCC CCC AAA CTC TGG GTT TAT GGC ACA TCC AAC TTG GCT TCT GGA GTC 65                   70                   75                   80
Pro Ala Arg Phe Ser Gly Gly Gly Ser Gly Thr Ser Tyr Ser Leu Thr Ile Ser Ser Val
CCT GCT CGC TTC AGT GGC GGT GGG TCT GGG ACC TCT TAC TCT CTC ACA ATC AGC AGT GTG 85                   90                   95                   100
Glu Ala Glu Asp Ala Ala Thr Tyr Tyr Cys Gln Gln Tyr Ser Gly Tyr Pro Leu Thr Phe
GAG GCT GAA GAT GCT GCC ACT TAT TAC TGC CAG CAG TAC AGT GGT TAC CCA CTC ACG TTC 105                  110                  115                  120
Gly Ala Gly Thr Lys Leu Glu Leu Lys Gly Ser Ser Gly Ser Gly Ser Glu Ser Lys
GGT GCT GGG ACC AAG CTT GAG CTG AAA GGT TCT TCT GGT TCT GGT TCC GAA TCT AAA
```

FIG. 39

```
            125                          130                          135                          140
Ser Thr Gln Leu Lys Glu Ser Gly Pro Val Leu Val Ala Pro Ser Gln Ser Leu Ser Ile
TCT ACT CAG CTG AAG GAG TCA GGA CCT GTC CTG GTG GCG CCC TCA CAG AGC CTG TCC ATC 145                          150                          155                          160
Thr Cys Thr Val Ser Gly Phe Ser Leu Thr Asn Tyr Gly Val His Trp Val Arg Gln Pro
ACT TGC ACT GTC TCT GGG TTT TCA TTA ACC AAC TAT GGT GTA CAC TGG GTT CGC CAG CCT 165                          170                          175                          180
Pro Gly Lys Gly Leu Glu Trp Leu Gly Val Ile Trp Ala Gly Asn Thr Asn Tyr Asn
CCA GGA AAG GGT CTG GAG TGG CTG GGA GTA ATA TGG GCT GGA AAC ACA AAT TAT AAT 185                          190                          195                          200
Ser Ala Leu Met Ser Arg Leu Ser Ile Asp Asp Lys Asp Asn Ser Lys Ser Gln Val Phe Leu
TCA GCT CTC ATG TCC AGA CTG AGC ATC GAT GAC AAA GAC AAT TCC AAG AGC CAA GTT TTA 205                          210                          215                          220
Lys Met Asn Ser Leu Gln Ile Asn Asp Thr Ala Ile Tyr Tyr Cys Ala Lys Arg Leu Gly
AAA ATG AAC AGT CTG CAA ATT AAT GAT ACA GCC ATA TAC TGT GCC AAA CGA CTG GAA 225                          230                          235                          240
Arg Ile Phe Tyr Tyr Ala Met Asp Tyr Trp Gly Gln Gly Thr Ser Val Thr Val Ser ***
CGA ATC TTT TAC TAT GCT ATG GAC TAT TGG GGT CAA GGA ACC TCA GTC ACC GTC TCC TAA
```

FIG. 39 (cont.)

```
Met Glu Asn Val Leu Thr Gln Ser Pro Ala Ile Met Ser Ala Ser Pro Gly Glu Lys Val
ATG GAA AAT GTG CTC ACC CAG TCT CCA GCA ATC ATG TCT GCA TCT CCA GGG GAA AAG GTC
                     5                  10                  15                  20

Thr Met Thr Cys Arg Ala Ser Ser Ser Val Ser Ser Tyr Leu His Trp Tyr Gln Gln
ACC ATG ACC TGC AGG GCC AGC TCA AGT GTA AGT TCC AGT TAC TTG CAC TGG TAC CAG CAG
                     25                 30                  35                  40

Lys Ser Gly Ala Ser Pro Lys Leu Trp Val Tyr Gly Thr Ser Asn Leu Ala Ser Gly Val
AAG TCA GGT GCC TCC CCC AAA CTC TGG GTT TAT GGC ACA TCC AAC TTG GCT TCT GGA GTC
                     45                 50                  55                  60

Pro Ala Arg Phe Ser Gly Ser Gly Ser Gly Thr Ser Tyr Ser Leu Thr Ile Ser Ser Val
CCT GCT CGC TTC AGT GGC AGT GGG TCT GGG ACC TCT TAC TCT CTC ACA ATC AGC AGT GTG
                     65                 70                  75                  80

Glu Ala Glu Asp Ala Ala Thr Tyr Tyr Cys Gln Gln Tyr Ser Gly Tyr Pro Leu Thr Phe
GAG GCT GAA GAT GCT GCC ACT TAT TAC TGC CAG CAG TAC AGT GGT TAC CCA CTC ACG TTC
                     85                 90                  95                  100

Gly Ala Gly Thr Lys Leu Lys Glu Ser Gly Ser Val Ser Ser Glu Gln Leu Ala Gln Phe
GGT GCT GGG ACC AAG CTT AAA GAA TCT GGT TCT TCT GTT TCT GAA CAG CTG GCT CAG TTT
                     105                110                 115                 120
```

FIG. 40

```
            125                 130                 135                 140
Arg Ser Leu Asp Val Gln Leu Lys Glu Gly Pro Val Leu Val Ala Pro Ser Gln Ser
CGT TCT CTG GAT GTG CAG CTG AAG GAG GGA CCT GTC CTG GTG GCG CCC TCA CAG AGC 145                 150                 155                 160
Leu Ser Ile Thr Cys Thr Val Ser Gly Phe Ser Leu Thr Asn Tyr Gly Val His Trp Val
CTG TCC ATC ACT TGC ACT GTC TCT GGG TTT TCA TTA ACC AAC TAT GGT GTA CAC TGG GTT 165                 170                 175                 180
Arg Gln Pro Pro Gly Lys Gly Leu Glu Trp Leu Gly Val Ile Trp Ala Gly Gly Asn Thr
CGC CAG CCT CCA GGA AAG GGT CTG GAG TGG CTG GGA GTA ATA TGG GCT GGT GGA AAC ACA 185                 190                 195                 200
Asn Tyr Asn Ser Ala Leu Met Ser Arg Leu Ser Ile Ser Lys Asp Asn Ser Lys Ser Gln
AAT TAT AAT TCA GCT CTC ATG TCC AGA CTG AGC ATC AGC AAA GAC AAT TCC AAG AGC CAA 205                 210                 215                 220
Val Phe Leu Lys Met Asn Ser Leu Gln Ile Asp Asp Thr Ala Ile Tyr Tyr Cys Ala Lys
GTT TTC TTA AAA ATG AAC AGT CTG CAA ATT GAT GAC ACA GCC ATA TAC TAC TGT GCC AAA 225                 230                 235                 240
Arg Leu Glu Arg Ile Phe Tyr Tyr Ala Met Asp Tyr Trp Gly Gln Gly Thr Ser Val Thr
CGA CTG GAA CGA ATC TTT TAC TAT GCT ATG GAC TAT TGG GGT CAA GGA ACC TCA GTC ACC

Val Ser ***
GTC TCC TAA
```

FIG. 40 (cont.)

```
                    5                  10                 15                 20
Met Asp Val Val Met Thr Gln Thr Pro Leu Ser Leu Pro Val Ser Leu Gly Asp Gln Ala
ATG GAT GTC GTG ATG ACC CAA ACT CCA CTC TCC CTG CCT GTC AGT CTT GGA GAT CAA GCC 25                 30                 35                 40
Ser Ile Ser Cys Arg Ser Ser Gln Ser Leu Val His Ser Asn Gly Asn Thr Tyr Leu Arg
TCC ATC TCT TGC AGA TCT AGT CAG AGC CTT GTA CAC AGT AAT GGA AAC ACC TAT TTA CGT 45                 50                 55                 60
Trp Tyr Leu Gln Lys Pro Gly Gln Ser Pro Lys Val Leu Ile Tyr Lys Val Ser Asn Arg
TGG TAC CTG CAG AAG CCA GGC CAG TCT CCA AAG GTC CTG ATC TAC AAA GTT TCC AAC CGA 65                 70                 75                 80
Phe Ser Gly Val Pro Asp Arg Phe Ser Gly Ser Gly Ser Gly Thr Asp Phe Thr Leu Lys
TTT TCT GGG GTC CCA GAC AGG TTC AGT GGC AGT GGA TCA GGG ACA GAT TTC ACA CTC AAG 85                 90                 95                 100
Ile Ser Arg Val Glu Ala Glu Asp Leu Gly Val Tyr Phe Cys Ser Gln Ser Thr His Val
ATC AGC AGA GTG GAG GCT GAG GAT CTG GGA GTT TAT TTC TGC TCT CAA AGT ACA CAT GTT 105                110                115                120
Pro Trp Thr Phe Gly Gly Gly Thr Lys Leu Glu Leu Lys Lys Ser Ser Gly Ser Gly Ser
CCG TGG ACG TTC GGT GGA GGC ACC AAG CTG GAA CTG AAA TCT TCT GGT TCT GGT TCT GGT 125                130                135                140
Ser Glu Ser Lys Ser Thr Gln Lys Leu Asp Glu Thr Gly Gly Leu Val Gln Pro Gly Gly
TCC GAA TCT AAA TCT ACT CAG AAA CTG GAT GAG ACT GGA GGC TTG GTG CAA CCT GGG
```

FIG. 41

```
                                145                 150                 155                 160
Arg Pro Met Lys Leu Ser Cys Val Ala Ser Gly Phe Thr Phe Ser Asp Tyr Trp Met Asn
AGG CCC ATG AAA CTC TCC TGT GTT GCC TCT GGA TTC ACT TTT AGT GAC TAC TGG ATG AAC 165                 170                 175                 180
Trp Val Arg Gln Ser Pro Glu Lys Gly Leu Glu Trp Val Ala Gln Ile Arg Asn Lys Pro
TGG GTC CGC CAG TCT CCA GAG AAA GGA CTG GAG TGG GTA GCA CAA ATT AGA AAC AAA CCT 185                 190                 195                 200
Tyr Asn Tyr Glu Thr Tyr Tyr Ser Asp Ser Val Lys Gly Arg Phe Thr Ile Ser Arg Asp
TAT AAT TAT GAA ACA TAT TAT TCA GAT TCT GTG AAA GGC AGA TTC ACC ATC TCA AGA GAT 205                 210                 215                 220
Asp Ser Lys Ser Ser Val Tyr Leu Gln Met Asn Asn Leu Arg Val Glu Asp Met Gly Ile
GAT TCC AAA AGT AGT GTC TAC CTG CAA ATG AAC AAC TTA AGA GTT GAA GAC ATG GGT ATC 225                 230                 235                 240
Tyr Cys Thr Arg Gly Ser Tyr Tyr Gly Met Asp Tyr Trp Gly Gln Gly Thr Ser Val Thr
TAT TGT ACG CGG GGT TCT TAC TAT GGT ATG GAC TAC TGG GGT CAA GGA ACC TCA GTC ACC

Val Ser ***
GTC TCC TAA
```

FIG. 41(cont.)

AMY

AMY start site

ATG ATT CAA AAA CGA AAG CGG ACA GTT TCG TTC AGA CTT GTG CTT ATG

TGC ACG CTG TTA TTT GTC AGT TTG CCG ATT ACA AAA ACA TCA GCC GTA
                                                                                                                             *Val

Asp Gly Asp Pro Ser MET
AAT GGG GAT CCG ATG TCG ATG GAT GTC GTG ATG ACC CAA ACT CCA CTC TCC
        | BamHI |     SCA -->

CTG CCT GTC AGT CTT GGA GAT CAA GCC ...

NPR

NPR start site

GTG GGT TTA GGT AAG AAA TTG TCT GTT GCT GTC GCC GCT TCC TTT ATG AGT
                                                                *Ala Gln Asp Pro Ser MET
TTA ACC ATC AGT CTG CCG GGT GTT CAG GCC GCT CAG GAT CCG TCG ATG GAT
                                                                                    | BamHI |   SCA -->

GTC GTG ATG ACC CAA ACT CCA CTC TCC CTG CCT GTC AGT CTT GGA GAT CAA

GCC ...

FIG. 46

APR

APR start site

GTG AGA GGC AAA AAA GTA TGG ATC AGT TTG CTG TTT GCT TTA GCG TTA ATC

\*Ala Gly Asp Pro
TTT ACG ATG GCG TTC GGC AGC ACA TCC TCT GCC CAG GCG GCA GGG GAT CCG
                                                                                                                                                                                                                | BamHI |

Ser MET
TCG ATG GAT GTC GTG ATG ACC CAA ACT CCA CTC TCC CTG CCT GTC AGT CTT
SCA -->

GGA GAT CAA GCC ...

FIG. 46(cont.)

SINGLE POLYPEPTIDE CHAIN BINDING MOLECULES

This application is a divisional of application Ser. No. 07/299,617, filed Jan. 19, 1989, now U.S. Pat. No. 4,946,778, which is a continuation-in-part of Ser. No. 07/092,110, filed Sep. 21, 1987, now abandoned, which is a continuation-in-part of Ser. No. 06/902,971, filed Sep. 2, 1986, now abandoned.

FIELD OF THE INVENTION

The present invention relates to single polypeptide chain binding molecules having the three dimensional folding, and thus the binding ability and specificity, of the variable region of an antibody. Methods of producing these molecules by genetic engineering are also disclosed.

DESCRIPTION OF THE BACKGROUND ART

The advent of modern molecular biology and immunology has brought about the possibility of producing large quantities of biologically active materials in highly reproducible form and with low cost. Briefly, the gene sequence coding for a desired natural protein is isolated, replicated (cloned) and introduced into a foreign host such as a bacterium, a yeast (or other fungi) or a mammalian cell line in culture, with appropriate regulatory control signals. When the signals are activated, the gene is transcribed and translated, and expresses the desired protein. In this manner, such useful biologically active materials as hormones, enzymes or antibodies have been cloned and expressed in foreign hosts.

One of the problems with this approach is that it is limited by the "one gene, one polypeptide chain" principle of molecular biology. In other words, a genetic sequence codes for a single polypeptide chain. Many biologically active polypeptides, however, are aggregates of two or more chains. For example, antibodies are three-dimensional aggregates of two heavy and two light chains. In the same manner, large enzymes such as aspartate transcarbamylase, for example, are aggregates of six catalytic and six regulatory chains, these chains being different. In order to produce such complex materials by recombinant DNA technology in foreign hosts, it becomes necessary to clone and express a gene coding for each one of the different kinds of polypeptide chains. These genes can be expressed in separate hosts. The resulting polypeptide chains from each host would then have to be reaggregated and allowed to refold together in solution. Alternatively, the two or more genes coding for the two or more polypeptide chains of the aggregate could be expressed in the same host simultaneously, so that refolding and reassociation into the native structure with biological activity will occur after expression. The approach, however, necessitates expression of multiple genes, and as indicated, in some cases, in multiple and different hosts. These approaches have proven to be inefficient.

Even if the two or more genes are expressed in the same organism it is quite difficult to get them all expressed in the required amounts.

A classical example of multigene expression to form multimeric polypeptides is the expression by recombinant DNA technology of antibodies. Genes for heavy and light chains have been introduced into appropriate hosts and expressed, followed by reaggregation of these individual chains into functional antibody molecules (see, for example, Munro, *Nature* 312:597 (1984); Morrison, S. L., *Science* 229:1202' (1985); and Oi et al., *BioTechniques* 4:214 (1986); Wood et al. (*Nature* 314:446–449 (1985)).

Antibody molecules have two generally recognized regions, in each of the heavy and light chains. These regions are the so-called "variable" region which is responsible for binding to the specific antigen in question, and the so-called "constant" region which is responsible for biological effector responses such as complement binding, etc. The constant regions are not necessary for antigen binding. The constant regions have been separated from the antibody molecule, and biologically active (i.e., binding) variable regions have been obtained.

The variable regions of an antibody are composed of a light chain and a heavy chain. Light and heavy chain variable regions have been cloned and expressed in foreign hosts, and maintain their binding ability (Moore et al., European Patent Publication 0088994 (published Sep. 21, 1983)).

Further, it is by now well established that all antibodies of a certain class and their $F_{ab}$ fragments whose structures have been determined by X-ray crystallography, even when from different species, show closely similar variable regions despite large differences in the hypervariable segments. The immunoglobulin variable region seems to be tolerant toward mutations in the combining loops. Thereafter, other than in the hypervariable regions, most of the so-called "variable" regions of antibodies, which are defined by both heavy and light chains, are in fact quite constant in their three dimensional arrangement. See, for example, Huber, R. (*Science* 233:702–703 (1986)).

While the art has discussed the study of proteins in three dimensions, and has suggested modifying their architecture (see, for example, the article "Protein Architecture: Designing from the Ground Up" by Van Brunt, J., *BioTechnology* 4: 277–283 (April, 1986)), the problem of generating single chain structures from multiple chain structures, wherein the single chain structure will retain the three-dimensional architecture of the multiple chain aggregate, has not been satisfactorily addressed.

Given that methods for the preparation of genetic sequences, their replication, their linking to expression control regions, formation of vectors therewith and transformation of appropriate hosts are well understood techniques, it would indeed be greatly advantageous to be able to produce, by genetic engineering, single polypeptide chain binding proteins having the characteristics and binding ability of multi chain variable regions of antibody molecules.

SUMMARY OF THE INVENTION

The present invention starts with a computer based system and method to determine chemical structures for converting two naturally aggregated but chemically separated light and heavy polypeptide chains from an antibody variable region into a single polypeptide chain which will fold into a three dimensional structure very similar to the original structure made of the two polypeptide chains.

The single polypeptide chain obtained from this method can then be used to prepare a genetic sequence coding therefor. The genetic sequence can then be replicated in appropriate hosts, further linked to control regions, and transformed into expression hosts, wherein it can be expressed. The resulting single polypeptide chain binding protein, upon refolding, has the binding characteristics of the aggregate of the original two (heavy and light) polypeptide chains of the variable region of the antibody.

The invention therefore comprises:

A single polypeptide chain binding molecule which has binding specificity substantially similar to the binding specificity of the light and heavy chain aggregate variable region of an antibody.

The invention also comprises genetic sequences coding for the above mentioned single polypeptide chain, cloning and expression vectors containing such genetic sequences, hosts transformed with such vectors, and methods of production of such polypeptides by expression of the underlying genetic sequences in such hosts.

The invention also extends to uses for the binding proteins, including uses in diagnostics, therapy, in vivo and in vitro imaging, purifications, and biosensors. The invention also extends to the single chain binding molecules in immobilized form, or in detectably labelled forms for utilization in the above mentioned diagnostic, imaging, purification or biosensor applications. It also extends to conjugates of the single polypeptide chain binding molecules with therapeutic agents such as drugs or specific toxins, for delivery to a specific site in an animal, such as a human patient.

Essentially all of the uses that the prior art has envisioned for monoclonal or polyclonal antibodies, or for variable region fragments thereof, can be considered for the molecules of the present invention.

The advantages of single chain over conventional antibodies are smaller size, greater stability and significantly reduced cost. The smaller size of single chain antibodies may reduce the body's imunologic reaction and thus increase the safety and efficacy of therapeutic applications. Conversely, the single chain antibodies could be engineered to be highly antigenic. The increased stability and lower cost permits greater use in biosensors and protein purification systems. Because it is a smaller and simpler protein, the single chain antibody is easier to further modify by protein engineering so as to improve both its binding affinity and its specificity. Improved affinity will increase the sensitivity of diagnosis and detection and detection systems while improved specificity will reduce the number of false positives observed.

BRIEF DESCRIPTION OF THE DRAWINGS

The present invention as defined in the claims can be better understood with reference to the text and to the following drawings, as follows:

Below the gap are four linker candidates (labeled 1, 2, 3 & 4), represented by a line joining the alpha carbons. In all cases, the first and penultimate alpha carbons are on lines parallel to the X-axis, spaced 8.0 A apart. Note that the space between dots in linker 1 is much shorter than in the gap.

Figure 20A:
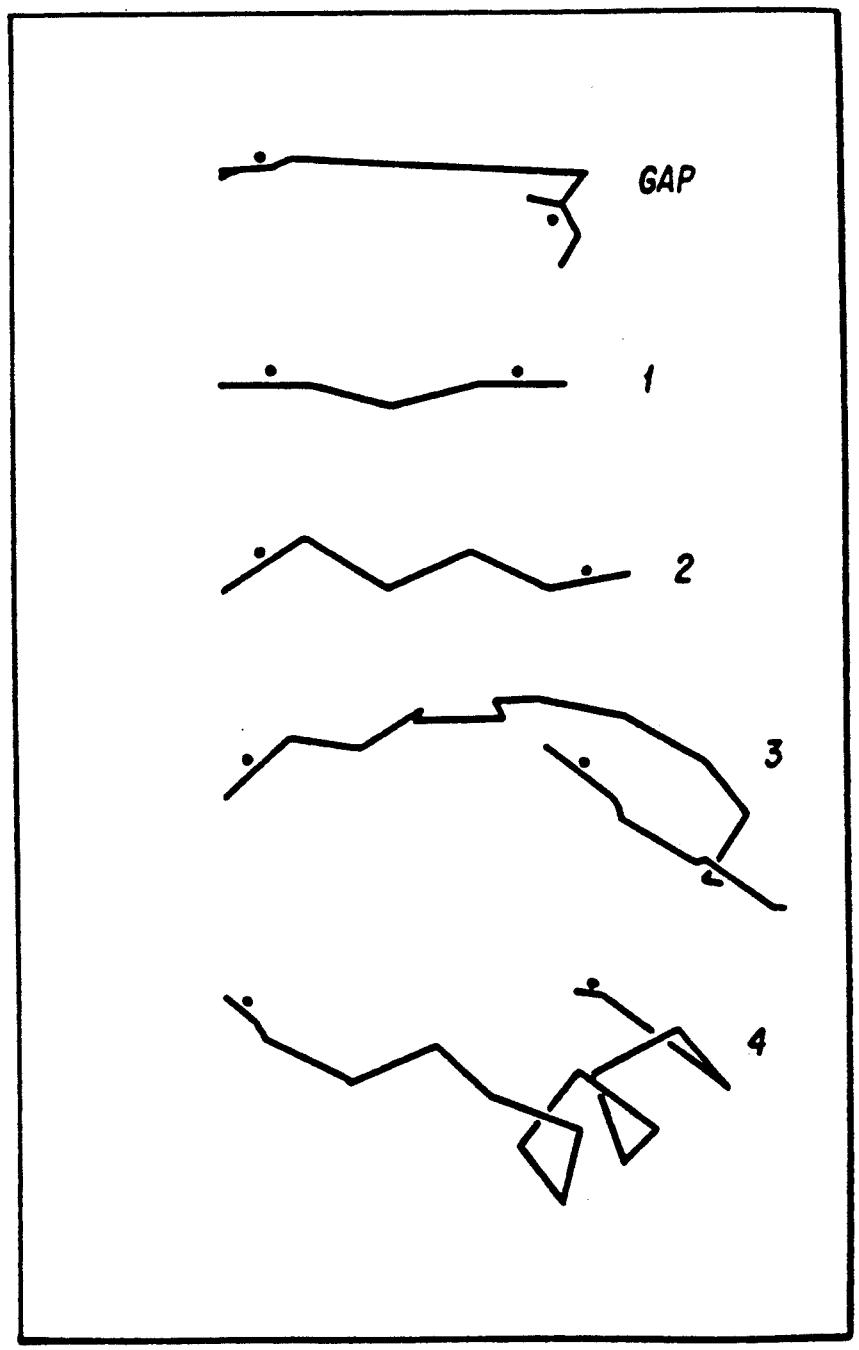
FIG. 20A shows five pieces of molecular structure. The uppermost segment consists of two peptides joined by a long line. The separation between the peptides is 12.7 A. The first C of each peptide lies on the X-axis. The two dots indicate the standard reference point in each peptide.
Figure 20B:
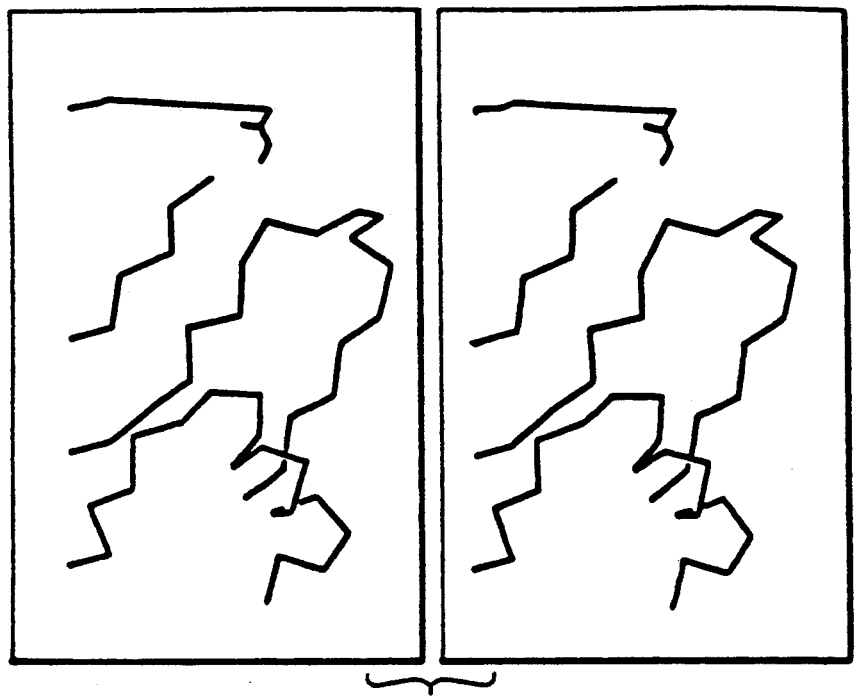

FIG. 20B shows the initial peptides of linkers 2, 3, and 4 which have been aligned with the first peptide of the gap. For clarity, the linkers have been translated vertically to their original positions.

The vector from the first peptide in the gap to the second peptide in the gap lies along the X-axis, a corresponding vector for linkers 3 and 4 also lies along the X-axis. Linker 2, however, has this vector pointing up and to the right, thus linker 2 is rejected.

Figure 20C:
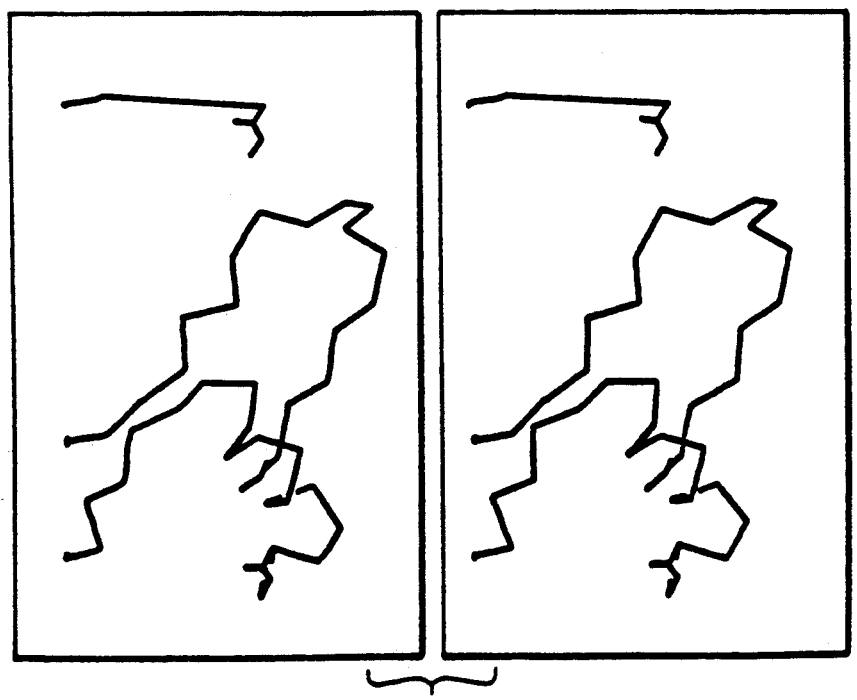

FIG. 20C shows the ten atoms which compose the initial and final peptides of linkers 3 and 4, which have been least-squares fit to the corresponding atoms from the gap. These peptides have been drawn in. Note that in the gap and in linker 4 the final peptide points down and lies more-or-less in the plane of the paper. In linker 3, however, this final peptide points down and to the left and is twisted about 90 degrees so that the carbonyl oxygen points toward the viewer. Thus linker 3 is rejected.

Sections B and C are stereo diagrams which may be viewed with the standard stereo viewer provided.

FIG. 21 shows the nucleotide sequence and translation of the sequence for the heavy chain of a mouse anti-bovine growth hormone (BGH) monoclonal antibody.

FIG. 22 shows the nucleotide sequence and translation of the sequence for the light chain of the same monoclonal antibody as that shown in FIG. 21.

Figure 23A:
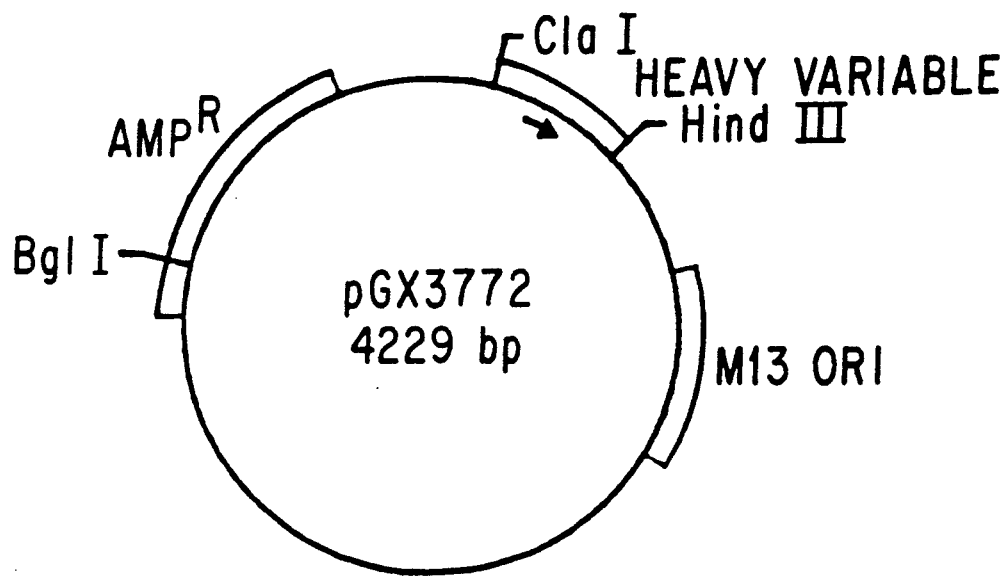
Figure 23B:
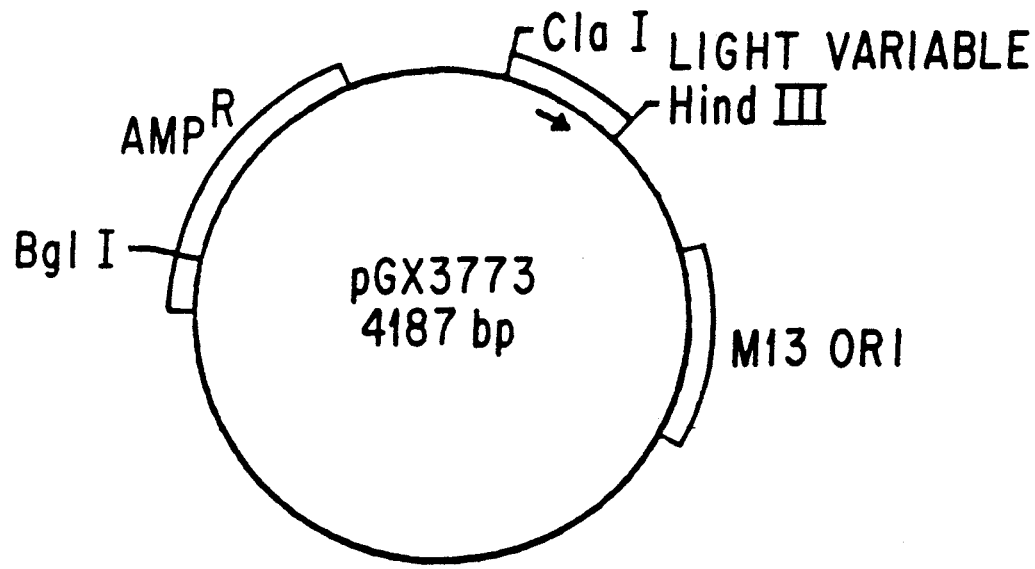

FIGS. 23A–23B are plasmid restriction maps containing the variable heavy chain sequence (pGX3772) and that containing the variable light sequence (pGX3773) shown in FIGS. 21 and 22.

FIG. 24 shows construction- TRY40 comprising the nucleotide sequence and its translation sequence of a single polypeptide chain binding protein prepared according to the methods of the invention.

Figure 25:
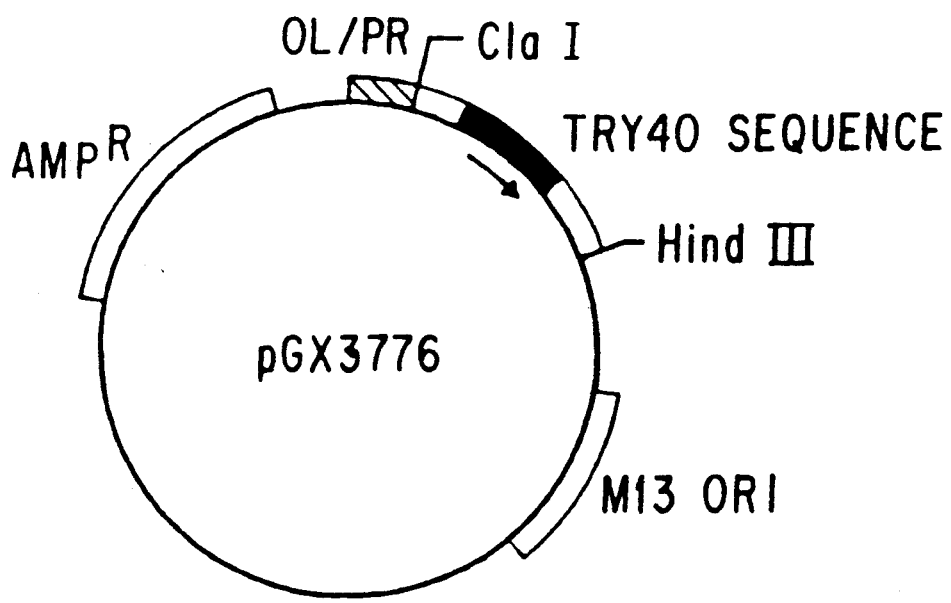

FIG. 25 shows a restriction map of the expression vector pGX3776 carrying a single chain binding protein, the sequence of which is shown in FIG. 24. In this and subsequent plasmid maps (FIGS. 27 and 29) the hashed bar represents the promoter $O_L/P_R$ sequence and the solid bar represents heavy chain variable region sequences.

FIG. 26 shows the sequences of TRY61, another single chain binding protein of the invention.

Figure 27:
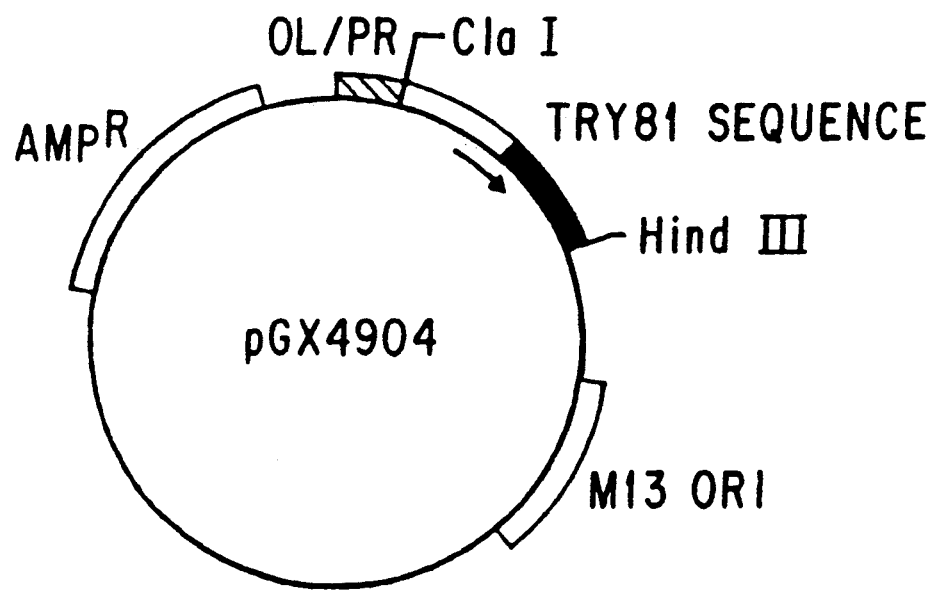

FIG. 27 shows expression plasmic pGX4904 carrying the genetic sequence shown in FIG. 26.

FIG. 28 shows the sequences of TRY59, another single chain binding protein of the invention.

Figure 29:
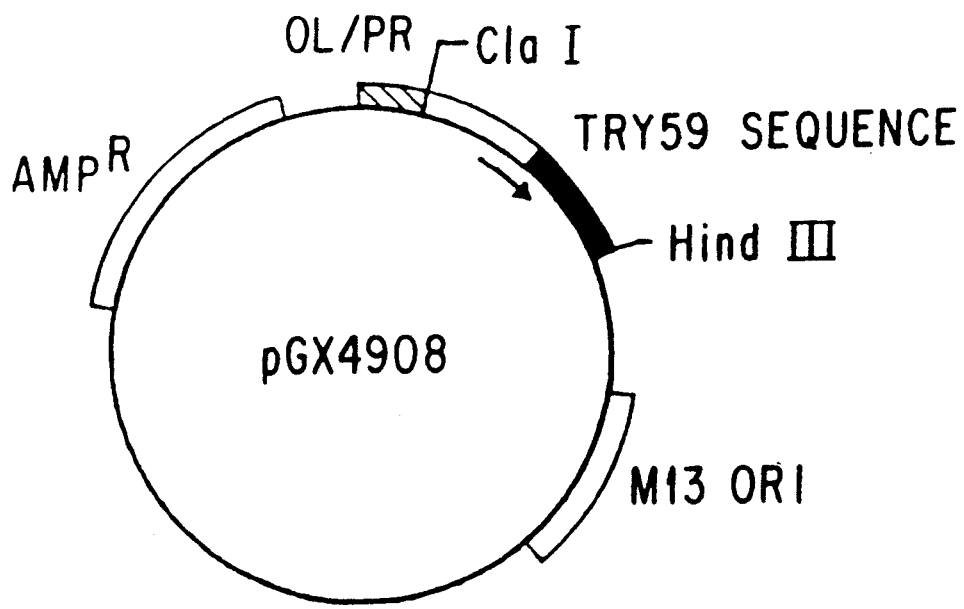

FIG. 29 shows the expression plasmid pGX4908 carrying the genetic sequence shown in FIG. 28.

FIGS. 30A, 30B, 30C, and 30D (stereo) are explained in detail in Example 1. They show the design and construction of double linked single chain antibody TRY40.

Figure 31A:
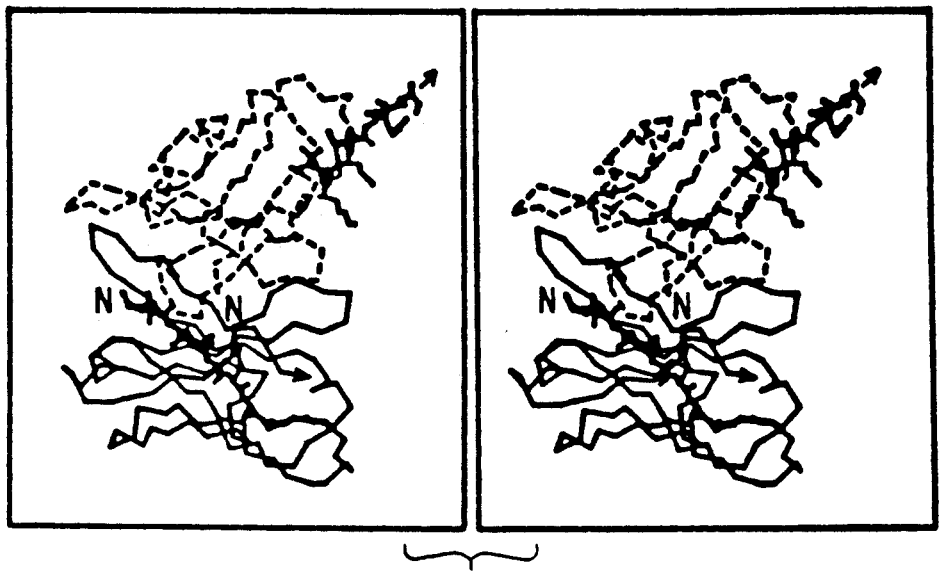
Figure 31B:
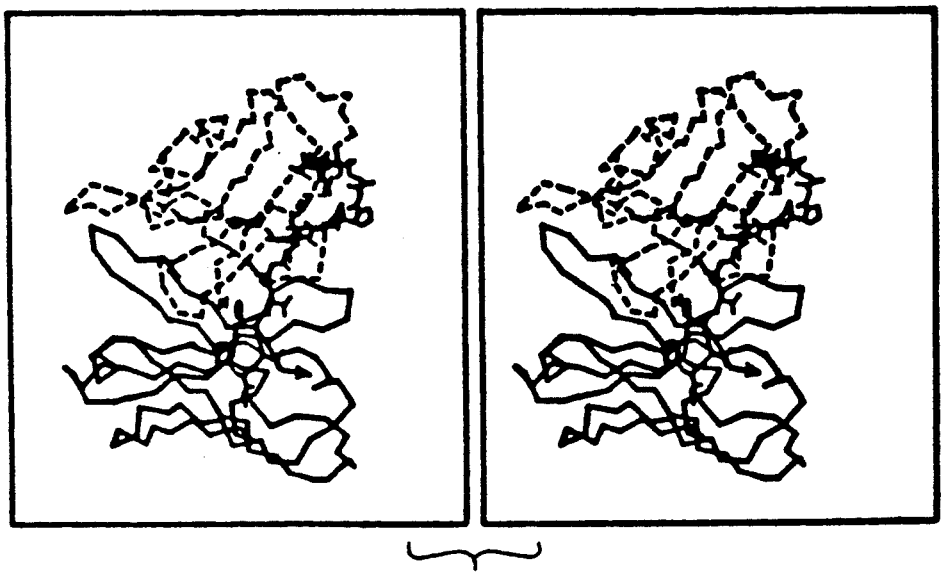

FIGS. 31A and 31B (stereo) are explained in detail in Example 2. They show the design and construction of single linked single chain antibody TRY61.

Figure 32A:
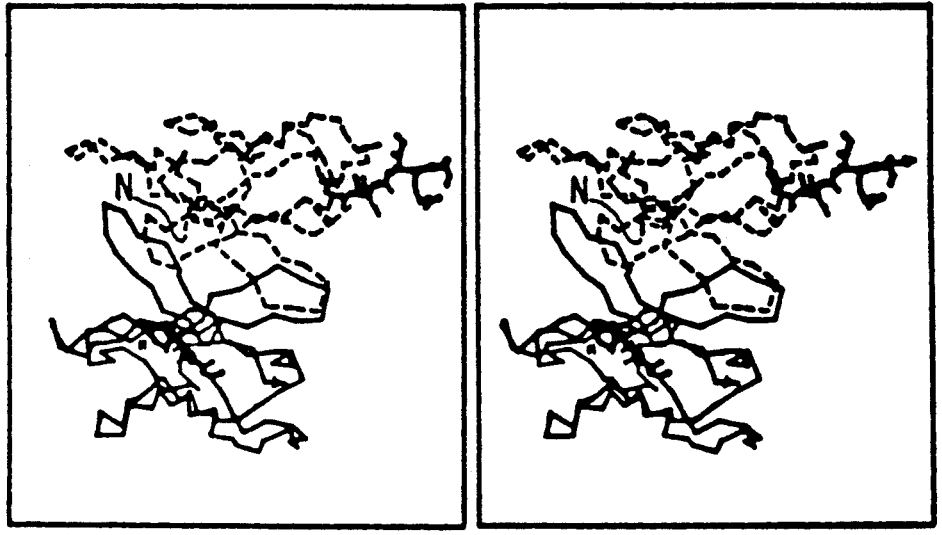
Figure 32B:
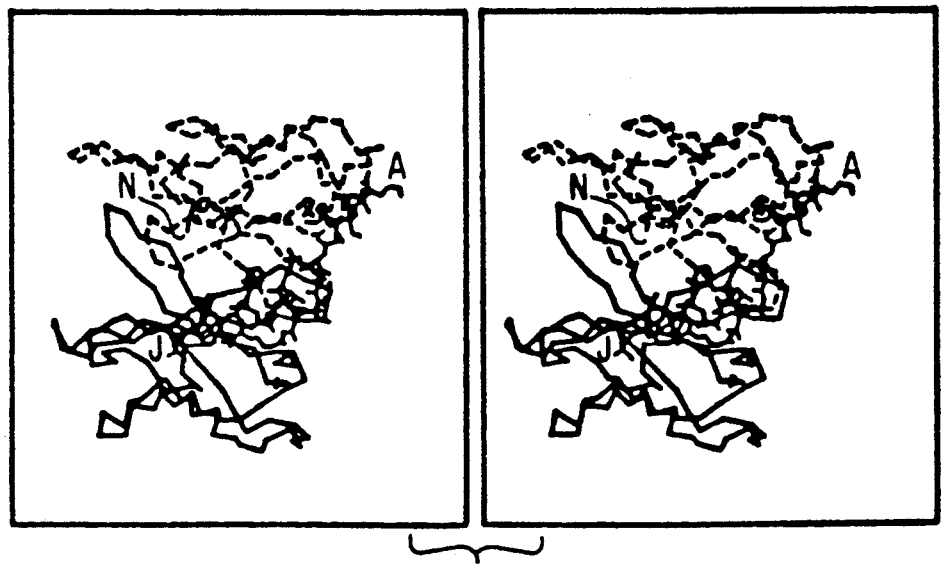

FIGS. 32A and 32B (stereo) are explained in detail in Example 3. They show the design and construction of single linked single chain antibody TRY59.

FIG. 33 is explained in Example 4 and shows the sequence of TRY104b.

Figure 34:
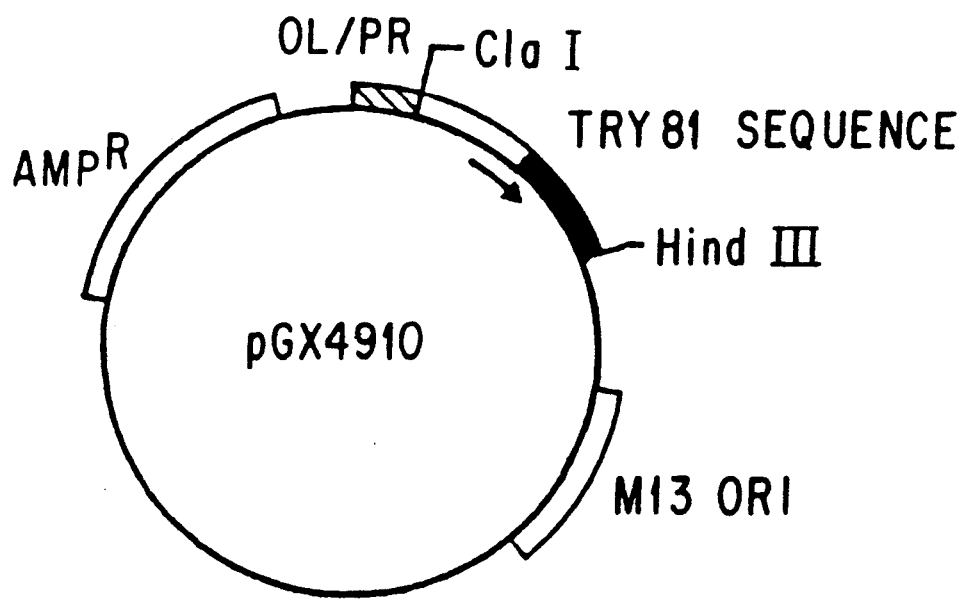

FIG. 34 shows a restriction map of the expression vector pGX4910 carrying a single linker construction, the sequence of which is shown in FIG. 33.

Figure 35:
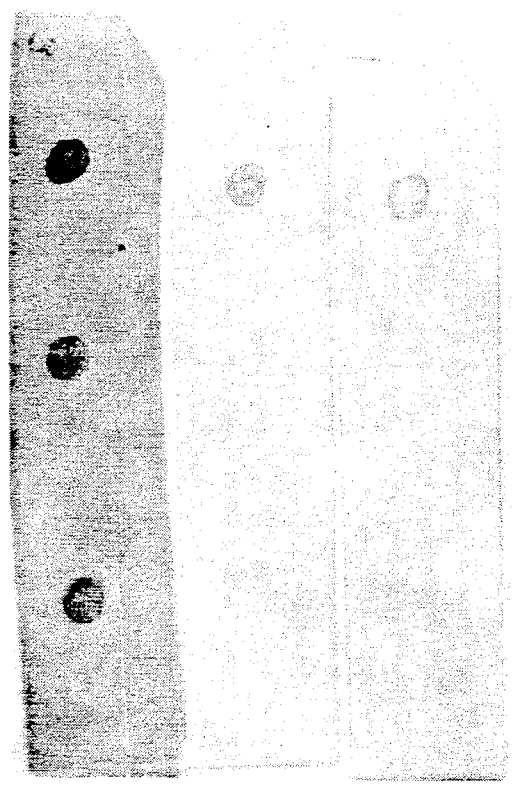

FIG. 35 shows the assay results for BGH binding activity wherein strip one represents TRY61 and strip two represents TRY40.

Figure 36:
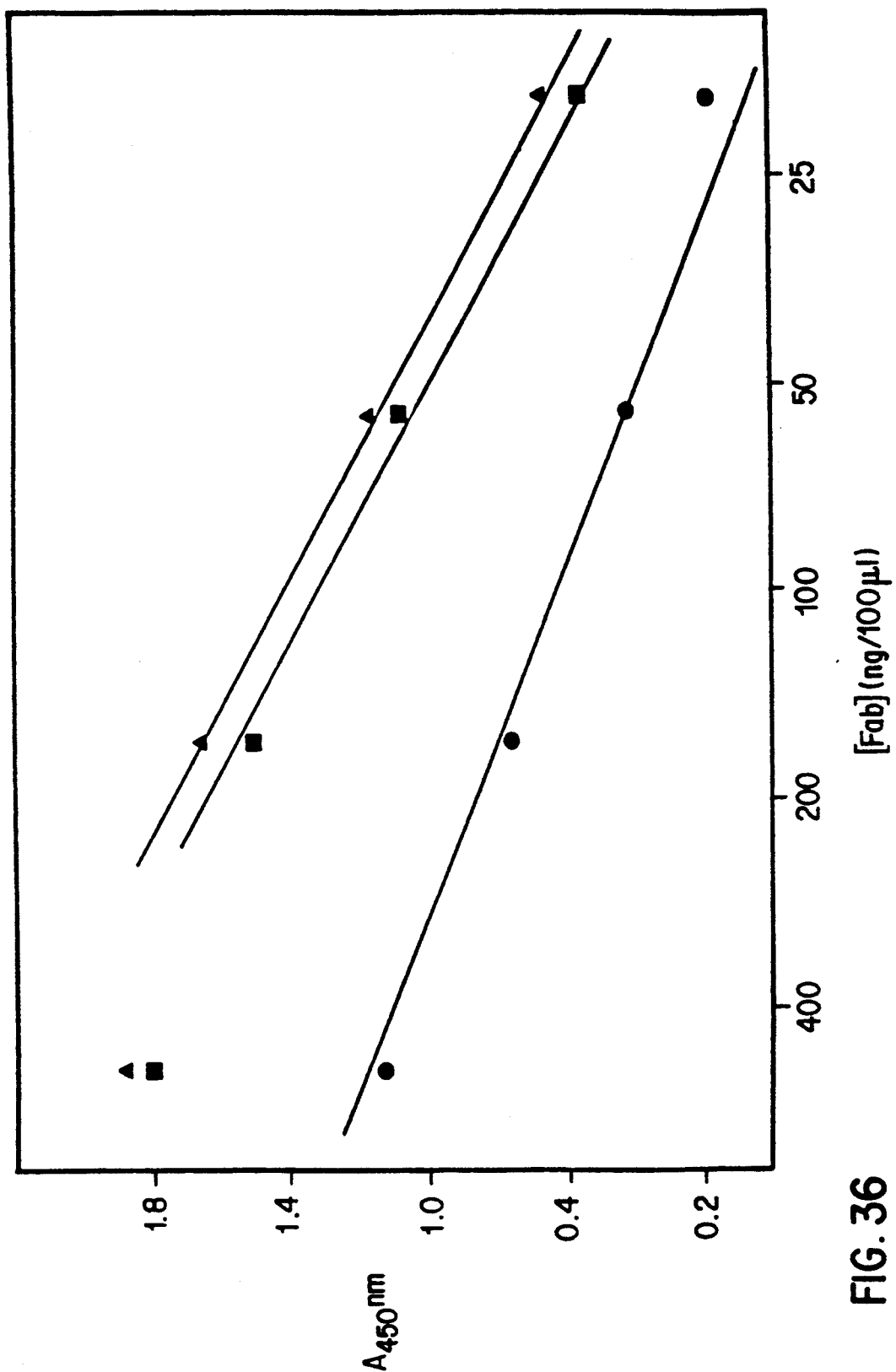

FIG. 36 is explained in Example 4 and shows the results of competing the $F_{ab}$ portion of 3C2 monoclonal with TRY59 protein.

Figure 37:
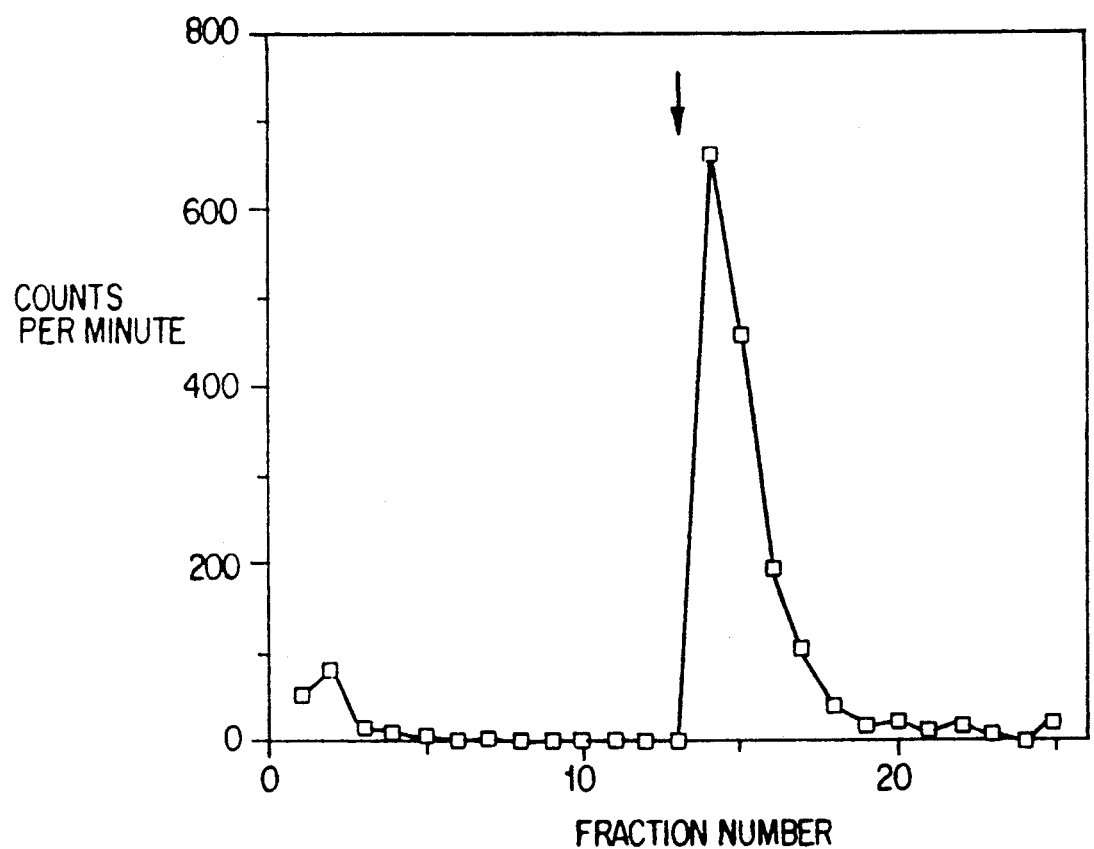

FIG. 37 shows the ability of a single chain binding molecule to bind to Bovine Growth Hormone-Sepharose (BGH-Sepharose).

Figure 38:
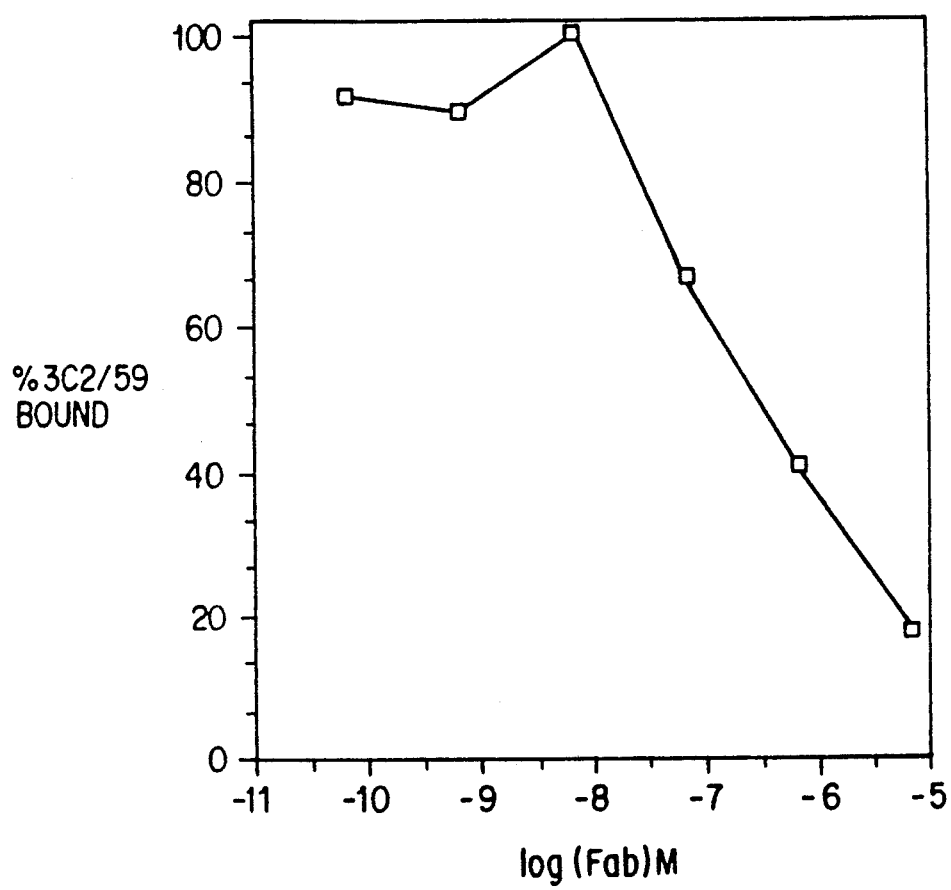

FIG. 38 shows a competition curve indicating the ability of $F_{ab}$ antibody fragments to compete with the single chain binding molecules of the invention for BGH binding.

FIGS. 39, 40, and 41 show the amino acid and nucleotide sequences of the single chain binding molecules: 18-2-3/TRY202', 18-2-3/TRY59, and 4-4-20/TRY202', respectively.

Figure 42A:
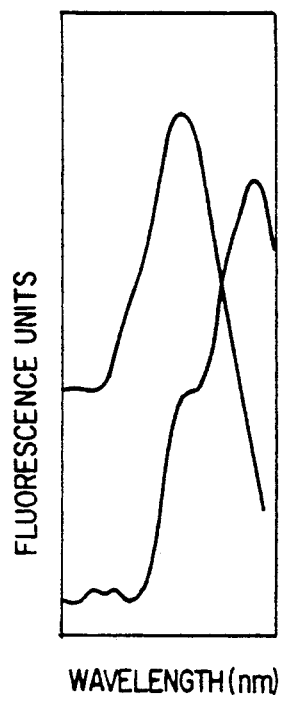
Figure 42B:
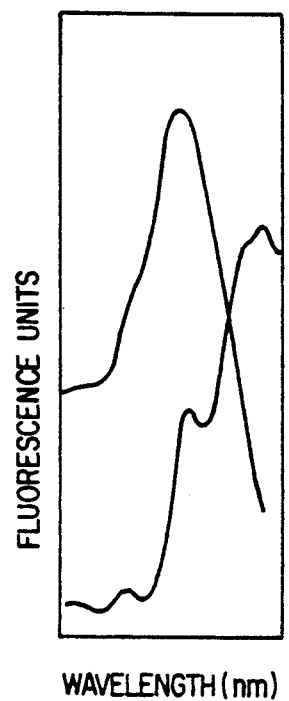
Figure 42C:

FIGS. 42A–42C show the absorption profile of fluorescein bound to 4-4-20 monoclonal antibody (A); an $F_{ab}$ fragment prepared from this antibody (B); and the 4-4-20/TRY202' protein (C).

Figure 43:
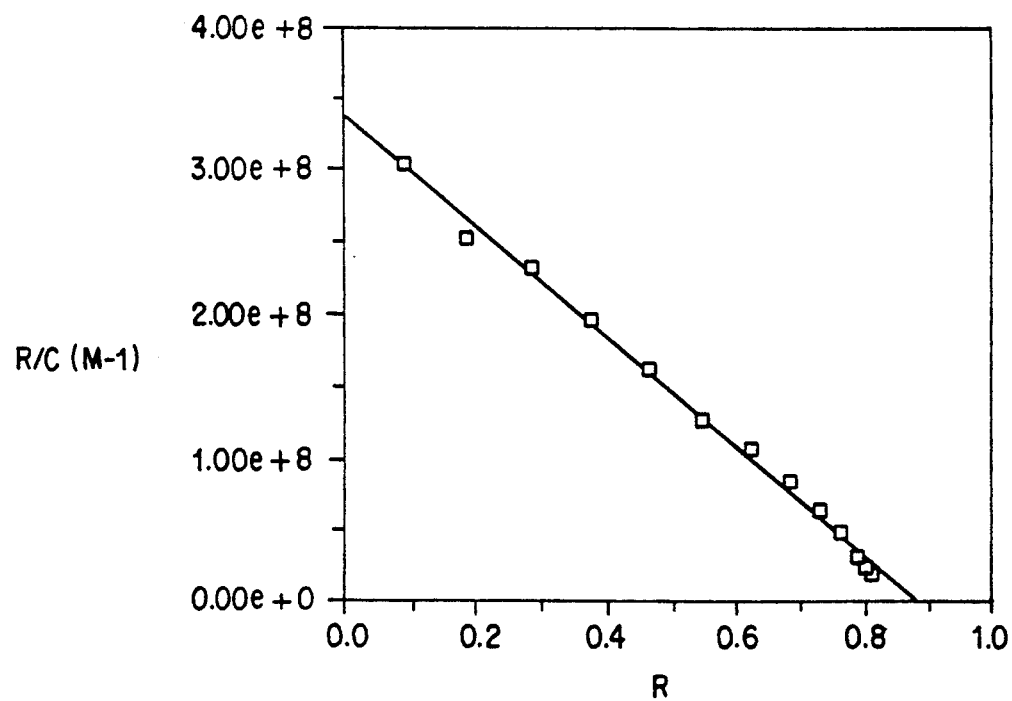

FIG. 43 shows a Scatchard plot analysis of the binding activity of 4-4-20/202' SCAT ™ protein.

Figure 44:
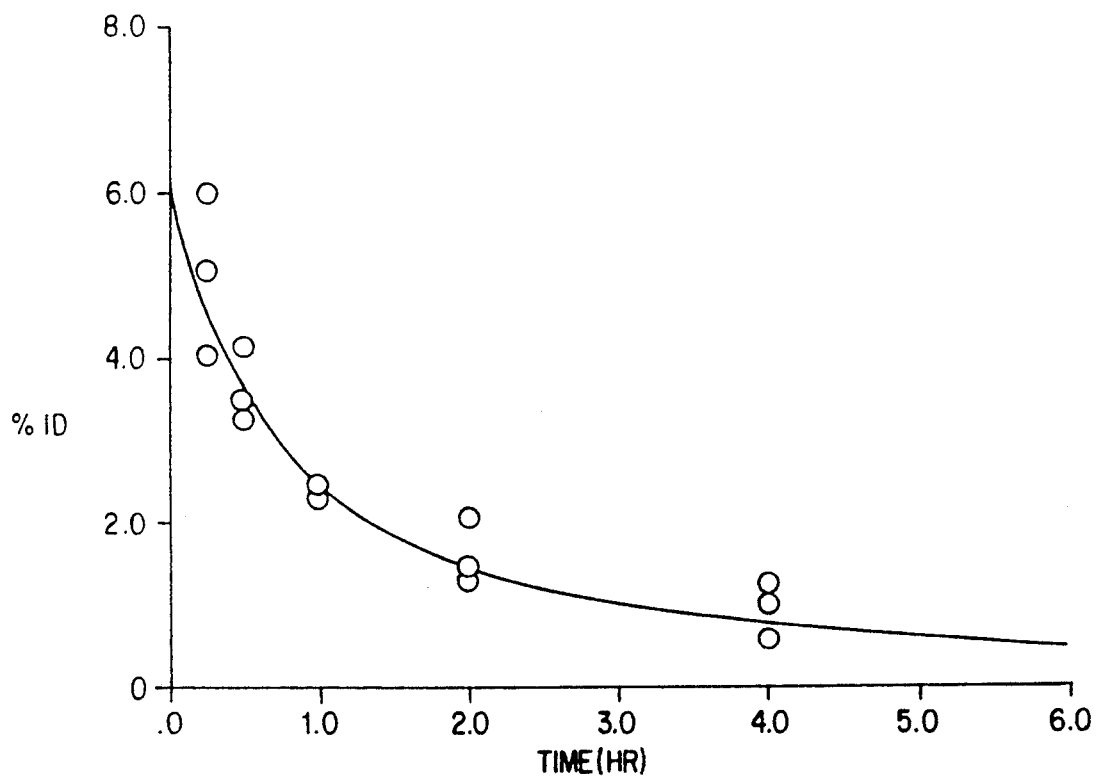

FIG. 44 shows the blood clearance of SCA ™ protein. The $T_{\frac{1}{2}\alpha}$ was 0.42. The $T_{\frac{1}{2}\beta}$ was 2.74.

Figure 45:
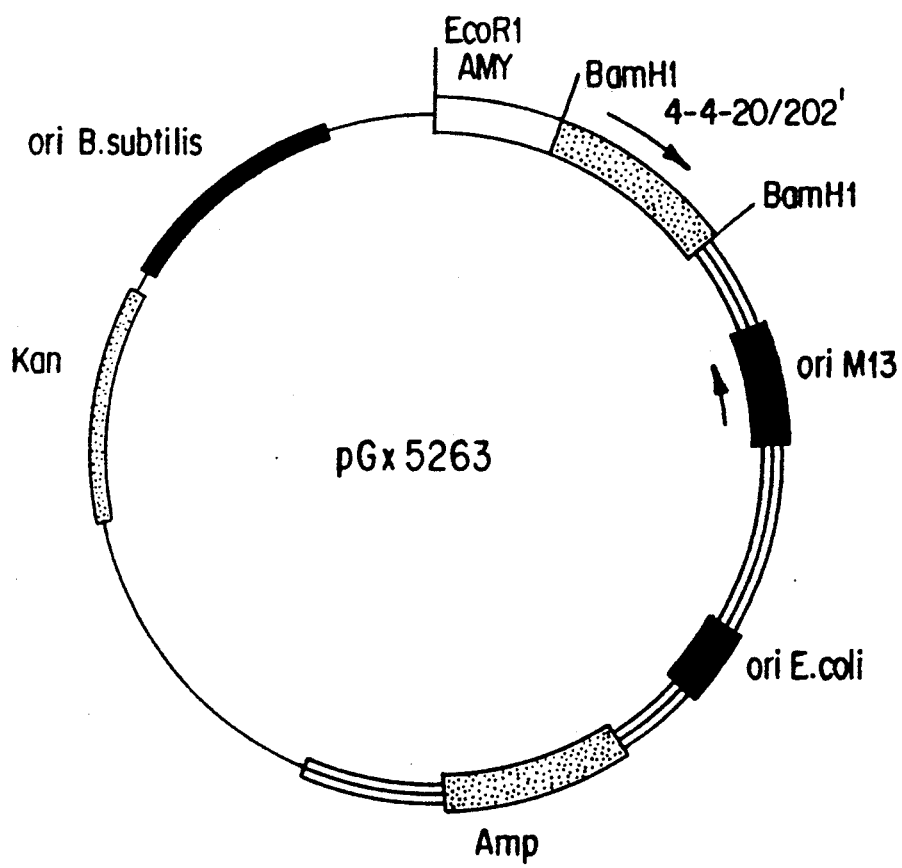

FIG. 45 shows a restriction and organizational map of pGX5263 which contains the amy promoter signal sequence coupled to the 4-4-20/202' gene.

FIG. 46 shows the sequences of the oligonucleotide linkers used to place the expression of the SCA ™ protein under the control of the amy, npr, and apr promoters of *B. subtilis*.

Figure 47:
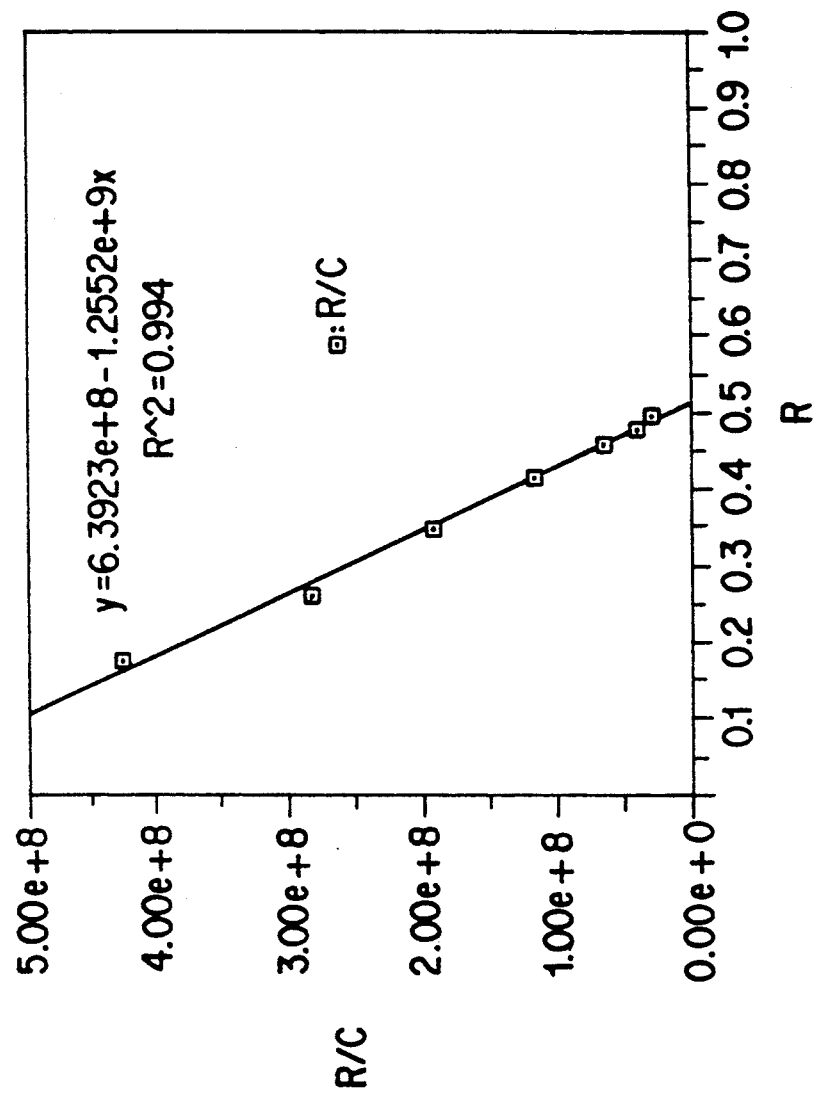

FIG. 47 shows a Scatchard analysis of the SCA ™ protein produced by *Bacillus subtilis*.

DETAILED DESCRIPTION OF THE PREFERRED EMBODIMENTS

Table of Contents

I. General Overview
II. Hardware and Software Environment
III. Single Linker Embodiment
  A. Plausible Site Selection
  B. Selection of Candidates
    1. Selecting Candidates with Proper Distance Between the N Terminal and the C Terminal.
    2. Selecting Candidates with Proper Direction from the N Terminal and the C Terminal.
    3. Selecting Candidates With Proper Orientation between the Termini
  C. Ranking and Eliminating Candidates
IV. Double and Multiple Linker Embodiments
  A. Plausible Site Selection
  B. Candidate Selection and Candidate Rejection Steps
V. Parallel Processing Embodiment

VI. Preparation and Expression of Genetic Sequences and Uses

I. General Overview

The present invention starts with a computer based system and method for determining and displaying possible chemical structures (linkers) for converting two naturally aggregated but chemically separate heavy and light (H and L) polypeptide chains from the variable region of a given antibody into a single polypeptide chain which will fold into a three-dimensional structure very similar to the original structure made of two polypeptide chains. The original structure is referred to hereafter as "native protein."

The first general step of the three general design steps of the present invention involves selection of plausible sites to be linked. In the case of a single linker, criteria are utilized to select a plausible site on each of the two polypeptide chains (H and L in the variable region) which will result in 1) a minimum loss of residues from the native protein chains and 2) a linker of minimum number of amino acids consistent with the need for stability. A pair of sites defines a gap to be bridged or linked.

A two-or-more-linker approach is adopted when a single linker can not achieve the two stated goals. In both the single-linker case and the two-or-more linker case, more than one gap may be selected for use in the second general step.

The second general step of the present invention involves examining a data base to determine possible linkers to fill the plausible gaps selected in the first general step, so that candidates can be enrolled for the third general step. Specifically, a data base contains a large number of amino acid sequences for which the three-dimensional structure is known. In the second general step, this data base is examined to find which amino acid sequences can bridge the gap or gaps to create a plausible one-polypeptide structure which retains most of the three dimensional features of the native (i.e., original aggregate) variable region molecule. The testing of each possible linker proceeds in three general substeps. The first general substep utilizes the length of the possible candidate.

Specifically, the span or length (a scalar quantity) of the candidate is compared to the span of each of the gaps. If the difference between the length of the candidate and the span of any one of the gaps is less than a selected quantity, then the present invention proceeds to the second general substep with respect to this candidate. FIG. 20A shows one gap and four possible linkers. The first linker fails the first general substep because its span is quite different from the span of the gap.

In the second general substep, called the direction substep, the initial peptide of the candidate is aligned with the initial peptide of each gap. Specifically, a selected number of atoms in the initial peptide of the candidate are rotated and translated as a rigid body to best fit the corresponding atoms in the initial peptide of each gap. The three dimensional vector (called the direction of the linker) from the initial peptide of the candidate linker to the final peptide of the candidate linker is compared to the three dimensional vector (called the direction of the gap) from the initial peptide of each gap to the final peptide of the same gap. If the ends of these two vectors come within a preselected distance of each other, the present invention proceeds to the third general substep of the second general step with respect to this candidate linker.

FIG. 20B shows one gap and three linkers. All the linkers have the correct span and the initial peptides have been aligned. The second linker fails the second general substep because its direction is quite different from that of the gap; the other two linkers are carried forward to the third general substep of the second general step.

In the third general substep of the second design of the step of the present invention, the orientations of the terminal peptides of each linker are compared to the orientations of the terminal peptides of each gap. Specifically, a selected number of atoms (3, 4, or 5; 5 in the preferred embodiment) from the initial peptide of the candidate plus the same selected number of atoms (3, 4, or 5; 5 in the preferred embodiment) from the final peptide of the candidate are taken as a rigid body. The corresponding atoms from one of the gaps (viz 5 from the initial peptide and 5 from the final peptide) are taken as a second rigid body. These two rigid bodies are superimposed by a least-squares fit. If the error for this fit is below some preselected value, then the candidate passes the third general substep of the second general step and is enrolled for the third general step of the present invention. If the error is greater than or equal to the preselected value, the next gap is tested. When all gaps have been tested without finding a sufficiently good fit, the candidate is abandoned.

The third general step of the present invention results in the ranking of the linker candidates from most plausible to least plausible. The most plausible candidate is the fragment that can bridge the two plausible sites of one of the gaps to form a single polypeptide chain, where the bridge will least distort the resulting three dimensional folding of the single polypeptide chain from the natural folding of the aggregate of the two originally chemically separate chains.

In this third general step of the present invention, an expert operator uses an interactive computer-graphics approach to rank the linker candidates from most plausible to least plausible. This ranking is done by observing the interactions between the linker candidate with all retained portions of the native protein. A set of rules are used for the ranking. These expert system rules can be built into the system so that the linkers are displayed only after they have satisfied the expert system rules that are utilized.

The present invention can be programmed so that certain expert rules are utilized as a first general substep in the third general step to rank candidates and even eliminate unsuitable candidates before visual inspection by an expert operator, which would be the second general substep of the third general step. These expert rules assist the expert operator in ranking the candidates from most plausible to least plausible. These expert rules can be modified based on experimental data on linkers produced by the system and methods of the present invention.

The most plausible candidate is a genetically producible single polypeptide chain binding molecule which has a very significantly higher probability (a million or more as compared to a random selection) of folding into a three dimensional structure very similar to the original structure made of the heavy and light chains of the antibody variable region than would be produced if random selection of the linker was done. In this way, the computer based system and method of the present invention can be utilized to engineer single polypeptide chains by using one or more linkers which convert naturally aggregated but chemically separated polypeptide chains into the desired single chain.

The elected candidate offers to the user a linked chain structure having a very significantly increased probability of proper folding than would be obtained using a random selection process. This means that the genetic engineering aspect of creating the desired single polypeptide chain is significantly reduced, since the number of candidates that have to be genetically engineered in practice is reduced by a corresponding amount. The most plausible candidate can be used to genetically engineer an actual molecule.

The parameters of the various candidates can be stored for later use. They can also be provided to the user either visually or recorded on a suitable media (paper, magnetic tape, color slides, etc.). The results of the various steps utilized in the design process can also be stored for later use or examination.

The design steps of the present invention operate on a conventional minicomputer system having storage devices capable of storing the amino acid sequence structure data base, the various application programs utilized and the parameters of the possible linker candidates that are being evaluated.

The minicomputer CPU is connected by a suitable serial processor structure to an interactive computer graphics display system. Typically, the interactive computer-graphics display system comprises a display terminal with resident three-dimensional application software and associated input and output devices, such as X/Y plotters, position control devices (potentiometers, an x-y tablet, or a mouse), and keyboard.

The interactive computer-graphics display system allows the expert operator to view the chemical structures being evaluated in the design process of the present invention. Graphics and programs are used to select the gaps (Gen. Step 1), and to rank candidates (Gen. Step 3). Essentially, it operates in the same fashion for the single linker embodiment and for the two or more linker embodiments.

For example, during the first general step of the present invention, the computer-graphics interactive display system allows the expert operator to visually display the two naturally aggregated but chemically separate polypeptide chains. Using three dimensional software resident in the computer-graphics display system, the visual representation of the two separate polypeptide chains can be manipulated as desired. For example, the portion of the chain(s) being viewed can be magnified electronically, and such magnification can be performed in a zoom mode. Conversely, the image can be reduced in size, and this reduction can also be done in a reverse zoom mode. The position of the portion of the molecule can be translated, and the displayed molecule can be rotated about any one of the three axes (x, y and z). Specific atoms in the chain can be selected with an electronic pointer. Selected atoms can be labeled with appropriate text. Specific portions of native protein or linker can be identified with color or text or brightness. Unwanted portions of the chain can be erased from the image being displayed so as to provide the expert operator with a visual image that represents only a selected aspect of the chain(s). Atoms selected by pointing or by name can be placed at the center of the three-dimensional display; subsequent rotation uses the selected atoms as the origin. These and other display aspects provide the expert operator with the ability to visually represent portions of the chains which increase the ability to perform the structural design process.

One of the modes of the present invention utilizes a serial computational architecture. This architecture using the present equipment requires approximately four to six hours of machine and operator time in order to go through the various operations required for the three general steps for a particular selection of gaps. Obviously, it would be desirable to significantly reduce the time since a considerable portion thereof is the time it takes for the computer system to perform the necessary computational steps.

An alternate embodiment of the present invention utilizes a parallel processing architecture. This parallel processing architecture significantly reduces the time required to perform the necessary computational steps. A hypercube of a large number of nodes can be utilized so that the various linkers that are possible for the selected sites can be rapidly presented to the expert system operator for evaluation.

Since there are between 200 and 300 known protein structures, the parallel processing approach can be utilized. There currently are computers commercially available that have as many as 1,024 computing nodes.

Using a parallel processing approach, the data base of observed peptide structures can be divided into as many parts as there are computing nodes. For example, if there are structures for 195 proteins with 219 amino acids each, one would have structures for $195 \times 218$ dipeptides, $195 \times 217$ tripeptides, $195 \times 216$ tetrapeptides, etc. One can extract all peptides up to some length n. For example, if n were 30, one would have $195 \times 30 \times 204$ peptides. Of course, proteins vary in length, but with 100 to 400 proteins of average length 200 (for example), and for peptide linkers up to length 30 amino acids (or any other reasonable number), one will have between 1,000,000 and 4,000,000 peptide structures. Once the peptides have been extracted and labeled with the protein from which they came, one is free to divide all the peptides as evenly as possible among the available computing nodes.

The parallel processing mode operates as follows. The data base of known peptides is divided among the available nodes. Each gap is sent to all the nodes. Each node takes the gap and tests it against those peptides which have been assigned to it and returns information about any peptides which fit the gap and therefore are candidate linkers. As the testing for matches between peptides and gaps proceeds independently in each node, the searching will go faster by a factor equal to the number of nodes.

A first embodiment of the present invention utilizes a single linker to convert the naturally aggregated but chemically separate heavy and light chains into a single polypeptide chain which will fold into a three dimensional structure very similar to the original structure made of two polypeptide chains.

A second embodiment utilizes two or more linkers to convert the two heavy and light chains into the desired single polypeptide chain. The steps involved in each of these embodiments utilizing the present invention are illustrated in the explanation below.

Once the correct amino acid sequence for a single chain binding protein has been defined by the computer assisted methodology, it is possible, by methods well known to those with skill in the art, to prepare an underlying genetic sequence coding therefor.

In preparing this genetic sequence, it is possible to utilize synthetic DNA by synthesizing the entire sequence de novo. Alternatively, it is possible to obtain cDNA sequences coding for certain preserved portions of the light and heavy chains of the desired antibody, and splice them together by means of the necessary sequence coding for the peptide linker, as described.

Also by methods known in the art, the resulting sequence can be amplified by utilizing well known cloning vectors and well known hosts. Furthermore, the amplified sequence, after checking for correctness, can be linked to promoter and terminator signals, inserted into appropriate expression vectors, and transformed into hosts such as procaryotic or eukaryotic hosts. Bacteria, yeasts (or other fungi) or mammalian cells can be utilized. Upon expression, either by itself or as part of fusion polypeptides, as will otherwise be known to those of skill in the art, the single chain binding protein is allowed to refold in physiological solution, at appropriate conditions of pH, ionic strength, temperature, and redox potential, and purified by standard separation procedures. These would include chromatography in its various different types, known to those will skill in the art.

The thus obtained purified single chain binding protein can be utilized by itself, in detectably labelled form, in immobilized form, or conjugated to drugs or other appropriate therapeutic agents, in diagnostic, imaging, biosensors, purifications, and therapeutic uses and compositions. Essentially all uses envisioned for antibodies or for variable region fragments thereof can be considered for the molecules of the present invention.

II. Hardware and Software Environment

Figure 1:
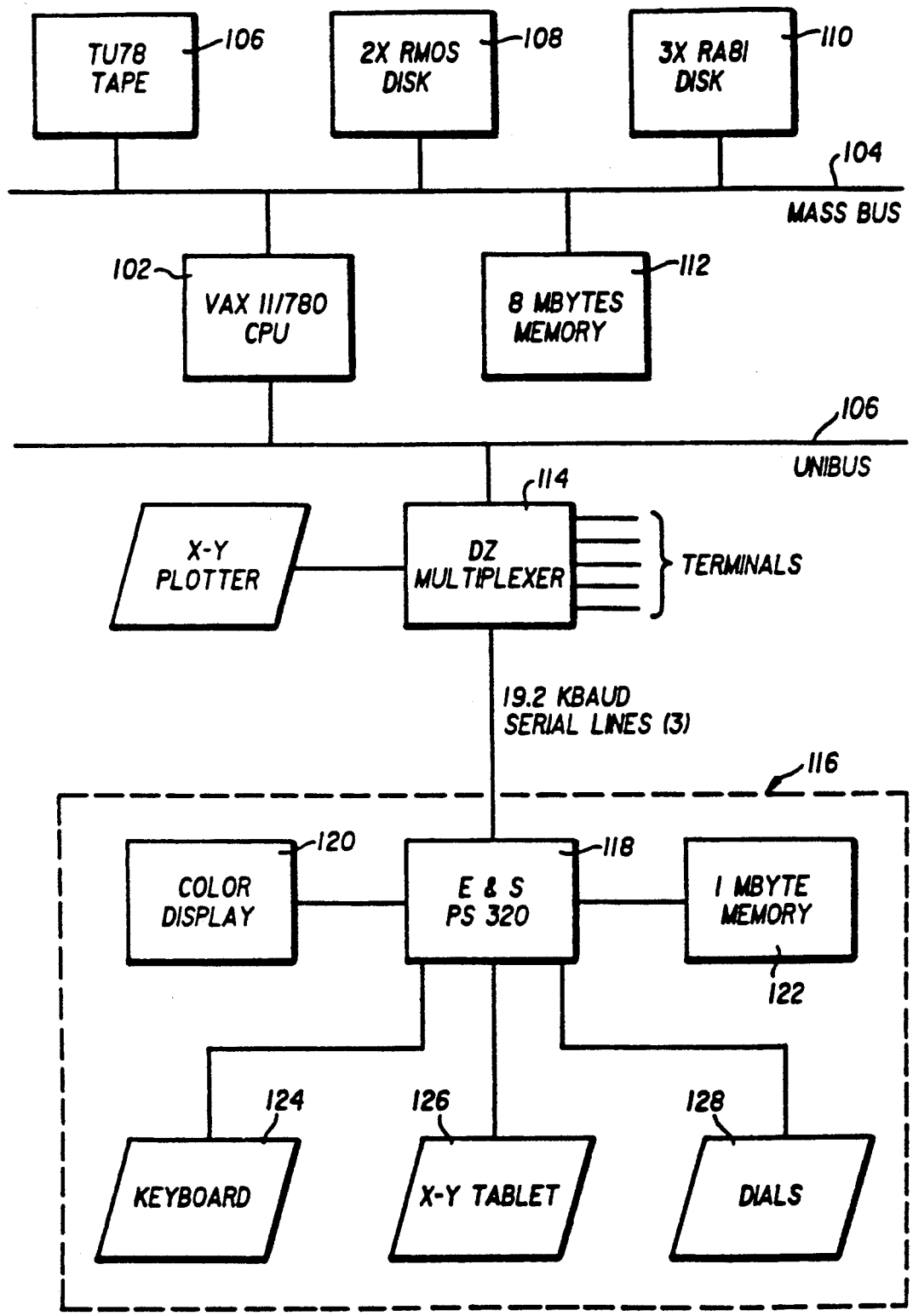
FIG. 1 is a block diagram of the hardware aspects of the serial processor mode of the present invention.

A block diagram of the hardware aspects of the present invention is found in FIG. 1. A central processing unit (CPU) 102 is connected to a first bus (designated massbus 104) and to a second bus (designated Unibus 106). A suitable form for CPU 102 is a model Vax 11/780 made by Digital Equipment Corporation of Maynard, Mass. Any suitable type of CPU, however, can be used.

Bus 104 connects CPU 102 to a plurality of storage devices. In the best mode, these storage devices include a tape drive unit 106. The tape drive unit 106 can be used, for example, to load into the system the data base of the amino acid sequences whose three dimensional structures are known. A suitable form for tape drive 106 is a Digital Equipment Corporation model TU 78 drive, which operates at 125 inches per second, and has a 1600–6250 bit per inch (BPI) dual capability. Any suitable type of tape drive can be used, however.

Another storage device is a pair of hard disk units labeled generally by reference numeral 108. A suitable form for disk drive 108 comprises two Digital Equipment Corporation Rmφ5 disk drives having, for example, 256 Mbytes of storage per disk. Another disk drive system is also provided in the serial processor mode and is labeled by reference numeral 110. This disk drive system is also connected to CPU 102 by bus 104. A suitable form for the disk system 110 comprises three Digital Equipment Corporation model Ra 81 hard disk drives having, for example, 450 Mbytes of storage per disk.

Dynamic random access memory is also provided by a memory stage 112 also connected to CPU 102 by bus 104. Any suitable type of dynamic memory storage device can be used. In the serial processor mode, the memory is made up of a plurality of semiconductor storage devices found in a DEC model Ecc memory unit. Any suitable type of dynamic memory can be employed.

The disk drives 108 and 110 store several different blocks of information. For example, they store the data base containing the amino acid sequences and structures that are read in by the tape drive 106. They also store the application software package required to search the data base in accordance with the procedures of the present invention. They also store the documentation and executables of the software. The hypothetical molecules that are produced and structurally examined by the present invention are represented in the same format used to represent the protein structures in the data base. Using this format, these hypothetical molecules are also stored by the disk drives 108 and 110 for use during the structural design process and for subsequent use after the process has been completed.

A Digital Equipment Corporation VAX/VMS DEC operating system allows for multiple users and assures file system integrity. It provides virtual memory, which relieves the programer of having to worry about the amount of memory that is used. Initial software was developed under versions 3.0 to 3.2 of the VAX/VMS operating system. The serial processor mode currently is running on version 4.4. DEC editors and FORTRAN compiler were utilized.

The CPU 102 is connected by Bus 106 to a multiplexer 114. The multiplexer allows a plurality of devices to be connected to the CPU 102 via Bus 106. A suitable form for multiplexer 114 is a Digital Equipment Corporation model Dz 16 terminal multiplexer. In the preferred embodiment, two of these multiplexers are used. The multiplexer 114 supports terminals (not shown in FIG. 1) and the serial communications (at 19.2 Kbaud, for example) to the computer-graphics display system indicated by the dash lined box 116.

The computer-graphics display system 116 includes an electronics stage 118. The electronic stage 118 is used for receiving the visual image prepared by CPU 102 and for displaying it to the user on a display (typically one involving color) 120. The electronic stage 118 in connection with the associated subsystems of the computer-graphics display system 116 provide for local control of specific functions, as described below. A suitable form of the electronics system 118 is a model PS 320 made by Evans & Sutherland Corp. of Salt Lake City, Utah. A suitable form for the display 120 is either a 25 inch color monitor or a 19 inch color monitor from Evans & Sutherland.

Dynamic random access memory 122 is connected to the electronic stage 118. Memory 122 allows the electronic system 118 to provide the local control of the image discussed below. In addition, a keyboard 124 of conventional design is connected to the electronic stage 118, as is an x/y tablet 126 and a plurality of dials 128. The keyboard 124, x/y tablet 126, and dials 128 in the serial processor mode are also obtained from Evans & Sutherland.

The computer generated graphics system 116, as discussed above, receives from CPU 102 the image to be displayed. It provides local control over the displayed image so that specific desired user initiated functions can be performed, such as:

(1) zoom (so as to increase or decrease the size of the image being displayed;

(2) clipping (where the sides, front or back of the image being displayed are removed);

(3) intensity depth queuing (where objects further away from the viewer are made dimmer so as to provide a desired depth effect in the image being displayed);

(4) translation of the image in any of the three axes of the coordinate system utilized to plot the molecules being displayed;

(5) rotation in any of the three directions of the image being displayed;

(6) on/off control of the logical segments of the picture. For example, a line connecting the alpha carbons of the native protein might be one logical segment; labels on some or all of the residues of the native protein might be a second logical segment; a trace of the alpha carbons of the linker(s) might be a third segment; and a stick figure connecting Carbon, Nitrogen, Oxygen, and Sulphur atoms of the linker(s) and adjacent residue of the native protein might be a fourth logical segment. The user seldom wants to see all of these at once; rather the operator first becomes oriented by viewing the first two segments at low magnification. Then the labels are switched off and the linker carbon trace is turned on. Once the general features of the linker are seen, the operator zooms to higher magnification and turns on the segments which hold more detail;

(7) selection of atoms in the most detailed logical segment. Despite the power of modern graphics, the operator can be overwhelmed by too much detail at once. Thus the operator will pick one atom and ask to see all amino acids within some radius of that atom, typically 6 Angstroms, but other radii can be used. The user may also specify that certain amino acids will be included in addition to those that fall within the specified radius of the selected atom;

(8) changing of the colors of various portions of the image being displayed so as to indicate to the viewer particular information using visual queuing.

As stated above, the serial processor mode of the present invention currently is running the application software on version 4.4 of the Vax/Vms operating system used in conjunction with CPU 102. The application programs were programed using the FLECS (FORTRAN Language with Extended Control Sections) programming language written in 1974 by Terry Beyer of the University of Oregon, Eugene, Oreg. FLECS is a FORTRAN preprocessor, which allows more logical programming. All of the code used in the serial processor mode was developed in FLECS. It can be appreciated, however, that the present invention encompasses other operating systems and programming languages.

The macromolecules displayed on color display 120 of the computer-graphics display system 116 utilize an extensively modified version of version 5.6 of FRODO. FRODO is a program for displaying and manipulating macromolecules. FRODO was written by T. A. Jones at Max Planck Institute for Biochemistry, Munich, West Germany, for building or modeling in protein crystallography. FRODO version 5.6 was modified so as to be driven by command files; programs were then written to create the command files. It is utilized by the electronic stage 118 to display and manipulate images on the color display 120. Again, any suitable type of program can be used for displaying and manipulating the macromolecules, the coordinates of which are provided to the computer-graphics display system 116 by the CPU 102.

Design documentation and memos were written using PDL (Program Design Language) from Caine, Farber & Gordon of Pasadena, Calif. Again, any suitable type of program can be used for the design documents and memos.

Figure 2:
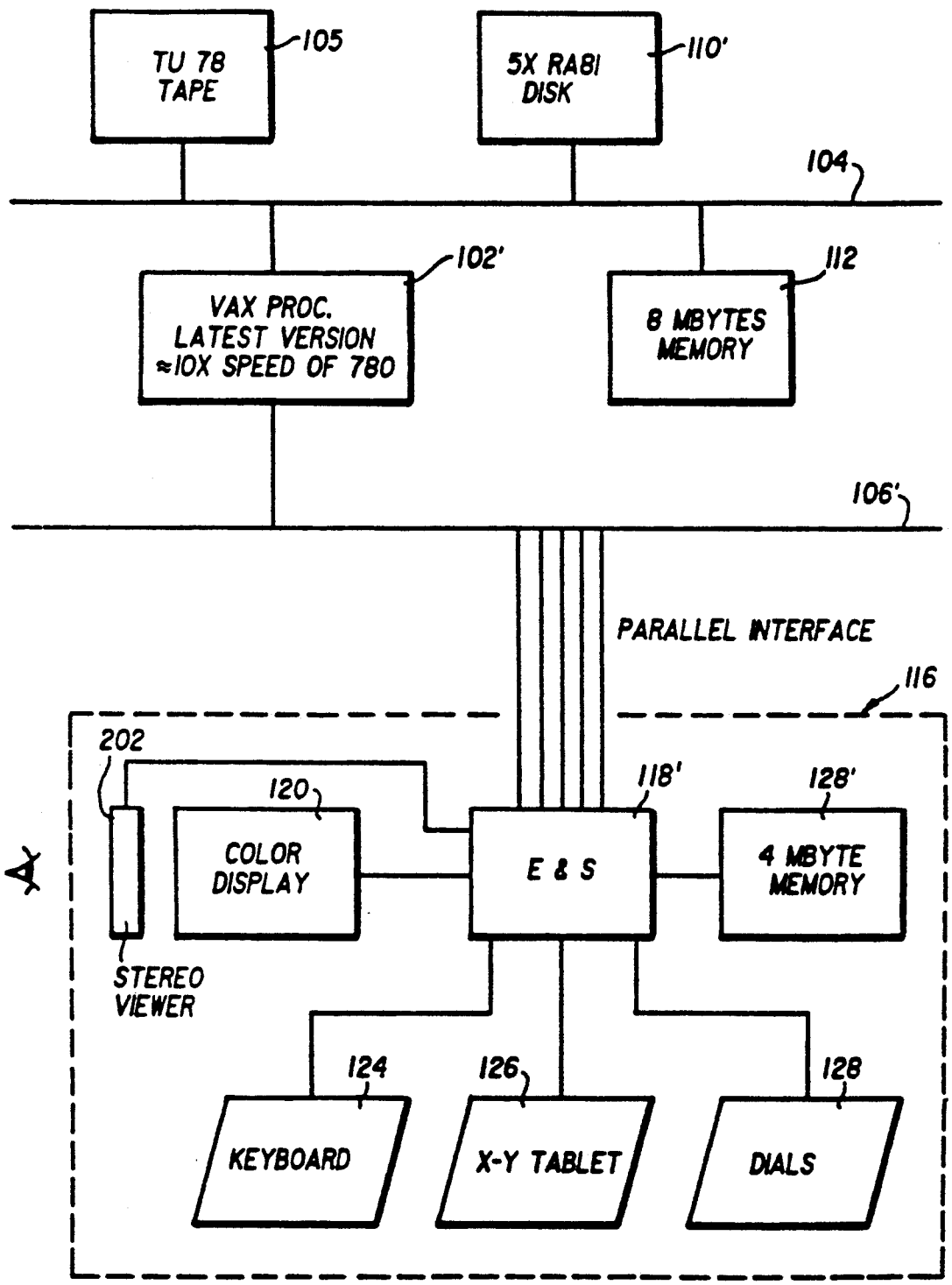
FIG. 2 is a block diagram of an alternate embodiment of the hardware aspects of the present invention.

FIG. 2 shows a block diagram for an improved version of the hardware system of the present invention. Like numbers refer to like items of FIG. 1. Only the differences between the serial processor mode system of FIG. 1 and the improved system of FIG. 2 are discussed below.

The CPU 102' is the latest version of the Vax 11/780 from Digital Equipment Corporation. The latest processor from DEC in the VAX product family is approximately ten times faster than the version shown in the serial,processor mode of FIG. 1.

Instead of the two Rm$\phi$5 disk drives 108 of FIG. 1, the embodiment of FIG. 2 utilizes five RA 81 disk drive units 110'. This is to upgrade the present system to more state of the art disk drive units, which provide greater storage capability and faster access.

Serial processor 106 is connected directly to the electronic stage 118' of the computer-graphics display system 116. The parallel interface in the embodiment of FIG. 2 replaces the serial interface approach of the serial processor mode of FIG. 1. This allows for faster interaction between CPU 102' and electronic stage 118' so as to provide faster data display to the expert operator.

Disposed in front of color display 120 is a stereo viewer 202'. A suitable form for stereo viewer 202' is made by Terabit, Salt Lake City, Utah. Stereo viewer 202' would provide better 3-D perception to the expert operator than can be obtained presently through rotation of the molecule.

In addition, this embodiment replaces the FRODO macromolecule display programs with a program designed to show a series of related hypothetical molecules.

This newer program performs the operations more quickly so that the related hypothetical molecules can be presented to the expert operator in a short enough time that makes examination less burdensome on the operator.

The programs can be modified so as to cause the present invention to eliminate candidates in the second general step where obvious rules have been violated by the structures that are produced. For example, one rule could be that if an atom in a linker comes closer than one Angstrom to an atom in the native structure the candidate would be automatically eliminated.

In addition, the surface accessibility of molecules could be determined and a score based on the hydrophobic residues in contact with the solvent could be determined. After the hydrophobic residues have been calculated, the candidates could be ranked so that undesired candidates could automatically be eliminated. The protein is modeled in the present invention without any surrounding matter. Proteins almost always exist in aqueous solution; indeed, protein crystals contain between 20% and 90% water and dissolved salts which fill the space between the protein molecules. Certain kinds of amino acids have side chains which make favorable interactions with aqueous solutions (serine, threonine, arginine, lysine, histidine, aspartic acid, glutamic acid, proline, asparagine, and glutamine) and are termed hydrophilic. Other amino acids have side chains which are apolar and make unfavorable interactions with water (phenylalanine, tryptophan, leucine, isoleucine, valine, methionine, and tyrosine) and are termed hydrophobic. In natural proteins, hydrophilic amino acids are almost always found on the surface, in contact with solvent; hydrophobic amino acids are almost always inside the protein in contact with other hydrophobic amino acids. The remaining amino acids (alanine, glycine, and cysteine) are found both inside proteins and on their surfaces. The designs of the present invention should resemble natural proteins as much as possible, so hydrophobic residues are placed inside and hydrophilic residues are placed outside as much as possible.

Programs could be utilized to calculate an energy for each hypothetical structure. In addition, programs could make local adjustments to the hypothetical molecules to minimize the energy. Finally, molecular dynamics could be used to identify particularly unstable parts of the hypothetical molecule. Although existing programs could calculate a nominal energy for each hypothetical structure, it has not yet been demonstrated that such calculations can differentiate between sequences which will fold and those that will not. Energy minimization could also be accomplished with extant program, but energy minimization also can not differentiate between sequences which will fold and those that will not. Molecular dynamics simulations currently cannot be continued long enough to simulate the actual folding or unfolding of a protein and so cannot distinguish between stable and unstable molecules.

Two megabytes of storage 128' in the computer generated display system 116 is added so that several different molecules can be stored at the display level. These molecules then can be switched back and forth on the color display 120 so that the expert operator can sequentially view them while making expert decisions. The parallel interface that is shown in FIG. 2 would allow the coordinates to be transferred faster from the CPU 102' to the electronics stage 118' of the computer generated display system 116.

The parallel processing architecture embodiment of the present invention is described below in Section V. This parallel architecture embodiment provides even faster analysis and display.

III. Single Linker Embodiment

This first embodiment of the present invention determines and displays possible chemical structures for using a single linker to convert the naturally aggregated but chemically separate heavy and light polypeptide chains into a single polypeptide chain which will fold into a three dimensional structure very similar to the original structure made of two polypeptide chains.

A. Plausible Site Selection

Figure 3:
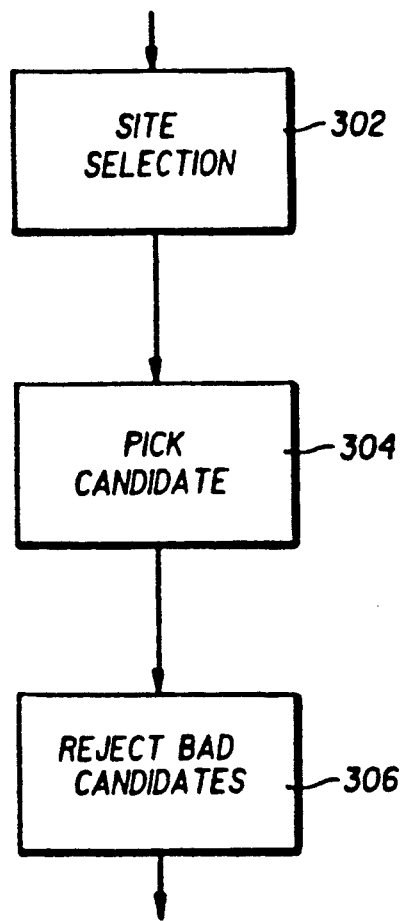
FIG. 3 is a block diagram of the three general steps of the present invention.

There are two main goals of the plausible site selection step 302 of the present invention shown in very generalized block diagram form in FIG. 3. The first goal is to select a first plausible site on the first chain that is the minimum distance from the second plausible site on the second chain. The first point on the first chain and the second point on the second chain comprise the plausible site.

The second goal of the site selection is to select plausible sites that will result in the least loss of native protein. Native protein is the original protein composed of the two aggregated polypeptide chains of the variable region. It is not chemically possible to convert two chains to one without altering some of the amino acids. Even if only one amino acid was added between the carboxy terminal of the first domain and the amino terminal of the second domain, the charges normally present at these termini would be lost. In the variable regions of antibodies, the termini of the H and L chains are not very close together. Hypothetical linkers which join the carboxy terminus of one chain to the amino terminus of the other do not resemble the natural variable region structures. Although such structures are not impossible, it is more reasonable to cut away small parts of the native protein so that compact linkers which resemble the native protein will span the gap. Many natural proteins are known to retain their structure when one or more residues are removed from either end.

Figure 4:
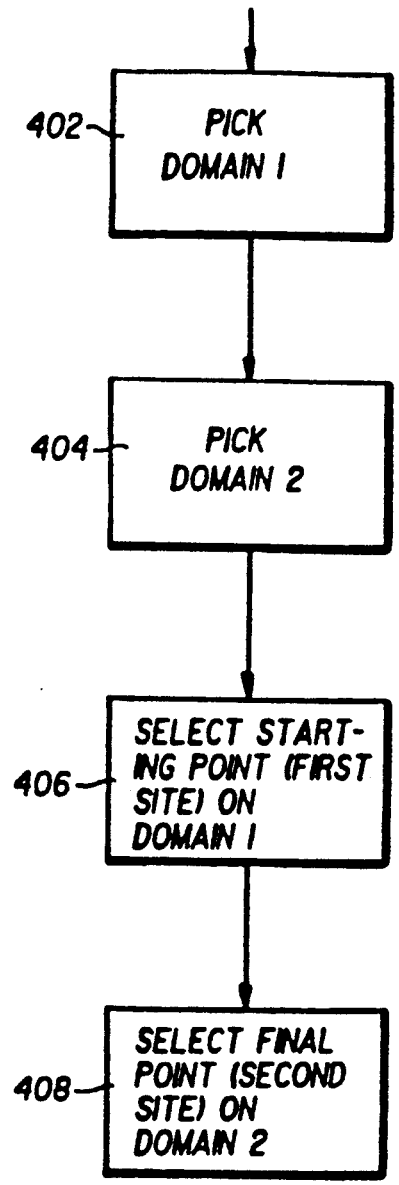
FIG. 4 is a block diagram of the steps in the site selection step in the single linker embodiment.

In the present embodiment, only a single linker (amino acid sequence or bridge for bridging or linking the two plausible sites to form a single polypeptide chain) is used. FIG. 4 shows in block diagram form the steps used to select plausible sites in the single linker. The steps of FIG. 4 are a preferred embodiment of step 302 of FIG. 3.

Figure 5A:
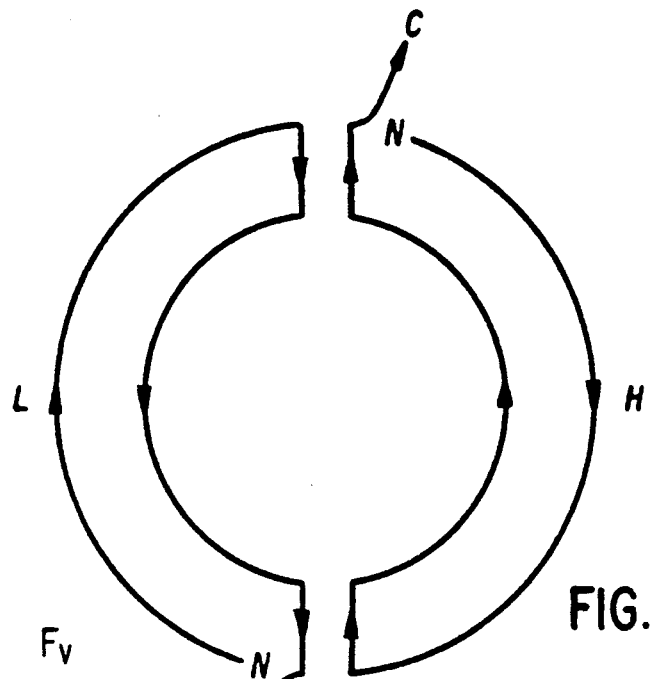
FIG. 5A is a schematic two dimensional simplified representation of the light chain L and heavy chain H of two naturally aggregated antibody variable region $F_v$ polypeptide chains used to illustrate the site selection process.
Figure 5B:
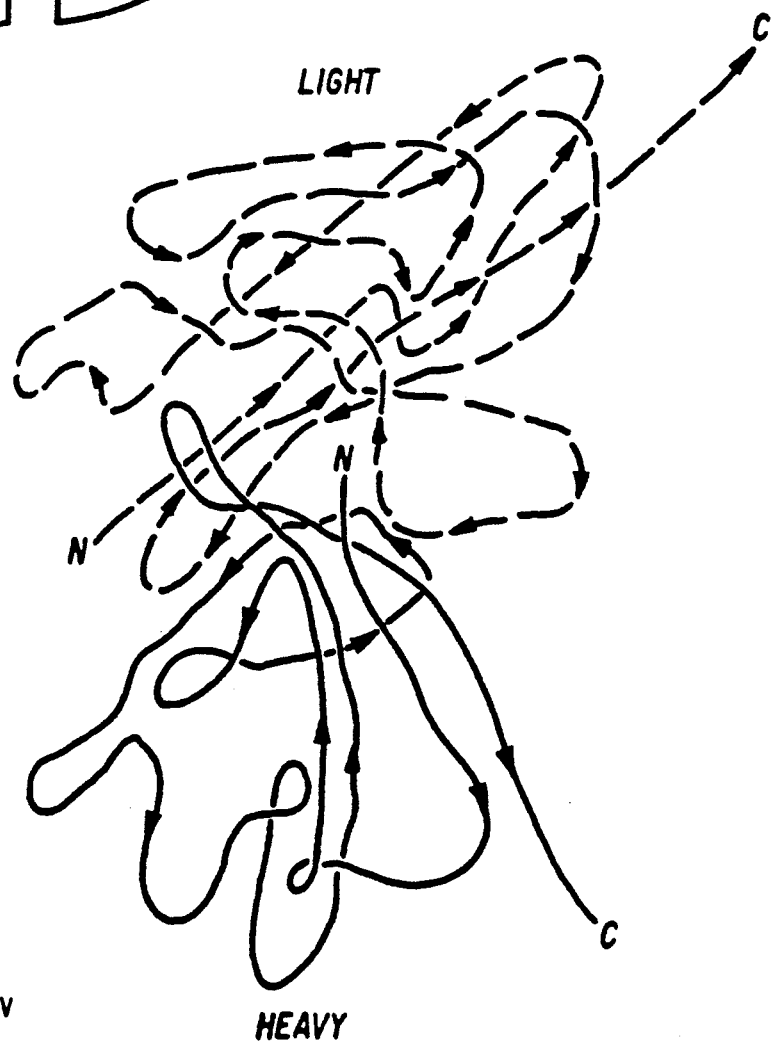
FIG. 5B is a two dimensional representation of the three dimensional relationship of the two aggregated polypeptide chains showing the light chain L (----) and the heavy chain H (-) of the variable region of one antibody.

A domain 1 is picked in a step 402 (see FIG. 4). A schematic diagram of two naturally aggregated but chemically separate polypeptide chains is shown in FIG. 5A. For purposes of illustration, assume that L is the light chain of the antibody variable region (the first polypeptide chain) and is domain 1. As shown in FIG. 5A, light chain L is on the left side, and heavy chain H is on the right side.

The next step 404 is to pick the domain 2, which, as indicated, is the heavy chain H of the antibody variable region on the right side of FIG. 5A.

Figure 6A:
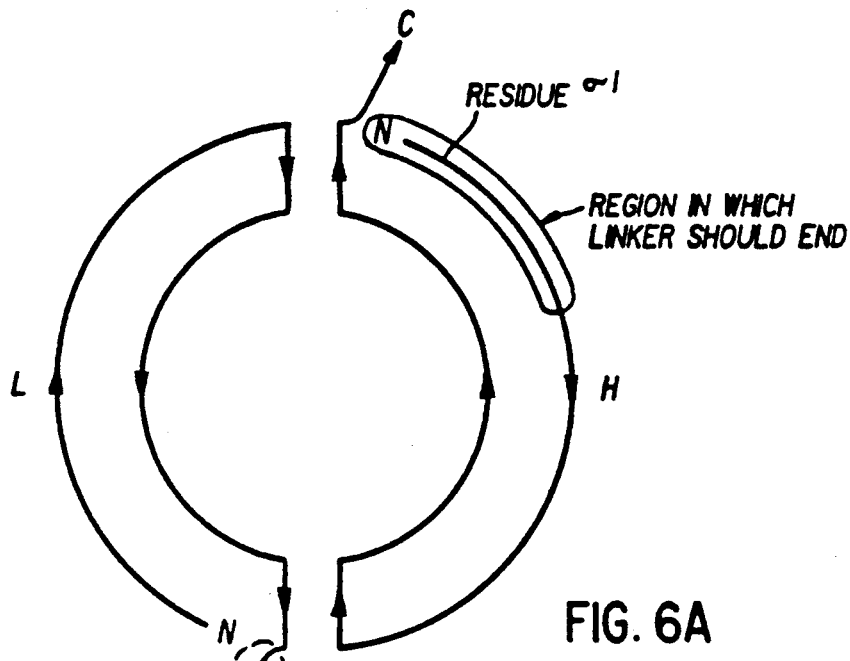
FIG. 6A is a simplified two dimensional schematic diagram of the two polypeptide chains showing the location of the residue tau 1 and the residue sigma 1.
Figure 6B:
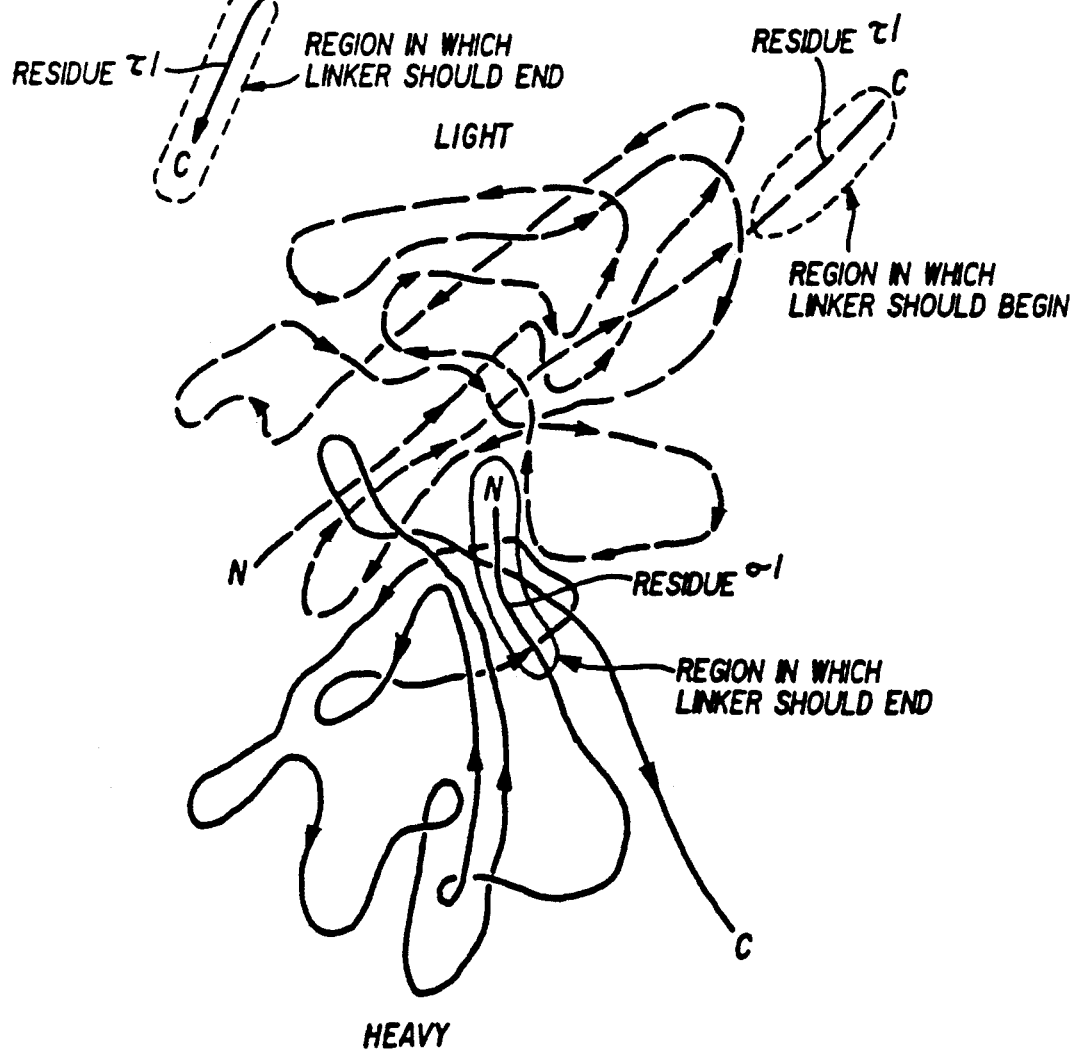
FIG. 6B is a two dimensional representation of the actual relationship of the two polypeptide chains showing the residue tau 1 and the residue sigma 1.

The linker that will be selected will go from domain 1 (the light chain L) towards domain 2 (heavy chain, H). As the linker will become part of the single polypeptide chain, it must have the same directionality as the polypeptides it is linking; i.e., the amino end of the linker must join the carboxy terminal of some amino acid in domain 1, and the carboxy terminal of the linker must join the amino terminal of some residue in domain 2. A starting point (first site) on domain 1 is selected, as represented by step in 406 in FIG. 4. The starting point is chosen to be close to the C (C for carboxy) terminal of domain 1, call this amino acid tau 1. It is important to pick tau 1 close to the C terminal to minimize loss of native protein structure. Residue tau 1 is shown schematically in two dimensions in FIG. 6A; it is also shown in FIG. 6B where it is presented in a two-dimensional representation of the naturally aggregated but chemically separate H and L polypeptide chains.

Next, the final point (second site) close the N (N for amino) terminal of domain 2 is selected, as indicated by step 408 of FIG. 4. The final site is an amino acid of domain 2 which will be called sigma 1. It is important that amino acid sigma 1 be close to the N terminal of domain 2 to minimize loss of native protein structure. Amino acid sigma 1 is shown schematically in FIG. 6A and in the more realistic representation of FIG. 6B.

Figure 7:
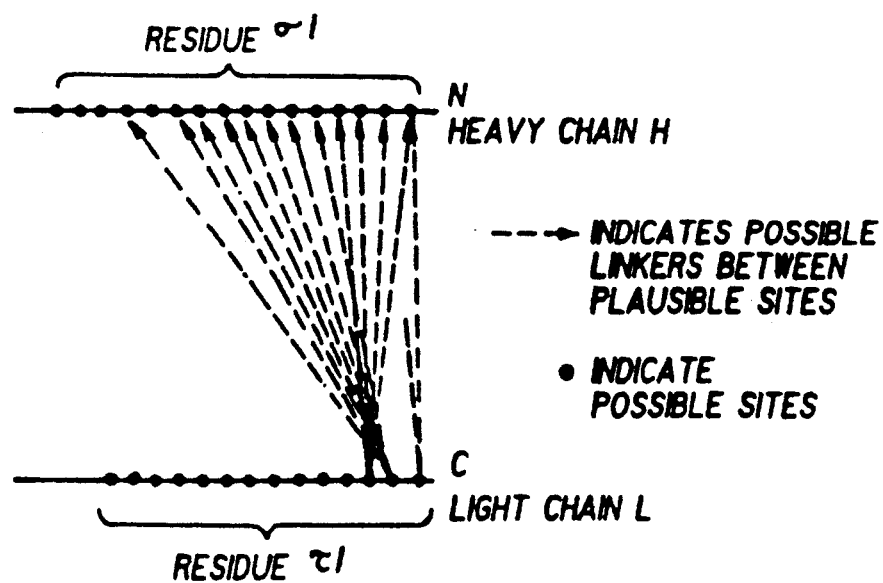
FIG. 7 shows in very simplified schematic way the concept of the direction linkers that are possible between the various possible sites on the light chain L and the heavy chain H in the residue tau 1 and residue sigma 1 respectively.

FIG. 7 shows in simplified form the concept that the linker goes from a first side at amino acid tau 1 in domain 1 to a second site at amino acid sigma 1 in domain 2. There are a plurality of possible first sites and a plurality of second sites, as is shown in FIG. 7. A computer program prepares a table which contains for each amino acid in domain 1 the identity of the closest amino acid in domain 2 and the distance. This program uses the position of the alpha carbon as the position of the entire amino acid. The expert operator prepares a list of plausible amino acids in domain 1 to be the first site, tau 1, and a list of plausible amino acids in domain 2 to be the second site, sigma 1. Linkers are sought from all plausible sites tau 1 to all plausible sites sigma 1. The expert operator must exercise reasonable judgement in selecting the sites tau 1 and sigma 1 in deciding that certain amino acids are more important to the stability of the native protein than are other amino acids. Thus the operator may select sites which are not actually the closest.

Figure 8A:
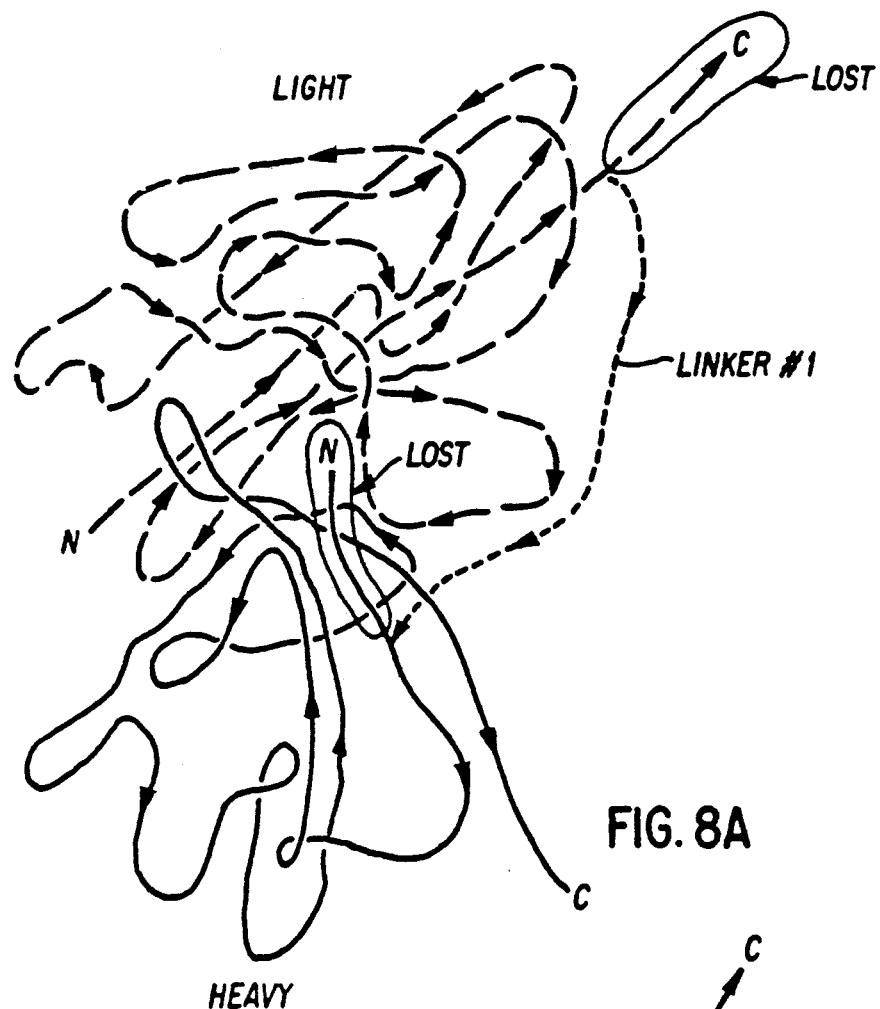
FIG. 8A is a two dimensional simplified schematic diagram of a single chain antibody linking together two separate chains (_____) (heavy)) and (...) (light)) by linker 1 (---) to produce a single chain antibody.
Figure 8B:
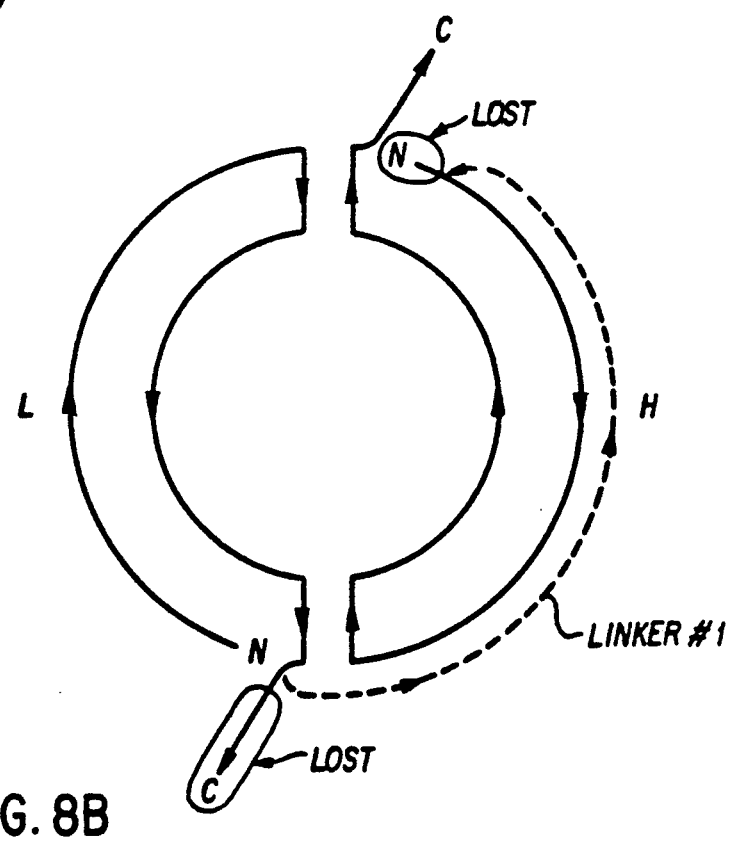
FIG. 8B is a two dimensional representation showing a single chain antibody produced by linking two aggregated polypeptide chains using linker 1.

The complete designed protein molecule in accordance with the present invention consists of the domain 1 (of the light chain L) up to the amino acid tau 1, the linker, as shown by the directional-line in FIG. 8A and in FIG. 8B, and the domain 2 from amino acid sigma 1 to the C terminus of the heavy chain, H. As shown in FIGS. 8A and 8B, in the representative example, this results in the following loss of native protein.

The first loss in native protein is from the residue after residue tau 1 to the C terminus of domain 1 (light chain L). The second loss of native protein is from the N terminus of domain 2 (heavy chain, H) to the amino acid before sigma 1.

As is best understood from FIG. 8A, the introduction of linker 1 produces a single polypeptide chain from the two naturally aggregated chains. The polypeptide chain begins with the N terminal of domain 1. Referring now to FIG. 8B, the chain proceeds through almost the entire course of the native light chain, L, until it reaches amino acid tau 1. The linker then connects the carboxy terminal of a very slightly truncated domain 1 to residue sigma 1 in the very slightly truncated domain 2. Since a minimum amount of native protein is eliminated, and the linker is selected to fit structurally as well as possible (as described below in connection with general steps 2 and 3 of the present invention), the resulting single polypeptide chain has a very high probability (several orders of magnitude greater than if the linker was selected randomly) to fold into a three-dimensional structure very similar to the original structure made of two polypeptide chains.

The single polypeptide chain results in a much more stable protein which contains a binding site very similar to the binding site of the original antibody. In this way a single polypeptide chain can be engineered from the naturally occurring two-polypeptide chain variable region, so as to create a polypeptide of only one chain, but maintaining the binding site of the antibody.

In the current mode of the present invention, the expert operator selects the sites with minimal help from the computer. The computer prepares the table of closest-residue-in-other-domain. The computer can provide more help in the following ways.

(1) Prepare a list of conserved and variable residues for variable regions of antibodies ($F_v$ region). Residues which vary from $F_v$ to $F_v$ would be much better starting or ending sites for linkage than are residues which are conserved over many different $F_v$ sequences.

(2) Prepare a list of solvent accessibilities. Amino acids exposed to solvent can be substituted with less likelihood of destabilizing the native structure than amino acids varied within the native structure. Exposed amino acids are better choices to start or end linkage.

With respect to each of the plurality of possible first sites (on domain 1 or light chain L) there are available a plurality of second sites (on domain 2 or heavy chain H) (See FIGS. 7 and 8A). As the second site is selected closer to the N terminus of domain 2, the distance to any of the plausible first sites increases. Also, as the first site is selected closer to the C terminus of domain 1 the distance to any of the plausible second sites increases. It is this tension between shortness of linker and retention of native protein which the expert operator resolves in choosing gaps to be linked. The penalty for including extra sites in the list of gaps are:

(1) searching in general step 2 will be slower; and
(2) more candidates will pass from step 2 many of which must be rejected in step 3. As step 3 is currently a manual step, this is the more serious penalty.

FIG. 8B shows diagrammatically by a directional arrow the possible links that can occur between the various sites near the C terminal of domain 1 and the various sites near the N terminal of domain 2.

B. Selection of Candidates

In the second of the three general steps of the present invention as used in the single linker embodiment, plausible candidates for linking the site 1 on domain 1 with site 2 on domain 2 are selected from a much larger group of candidates. This process of winnowing out candidates results in the expert operator and/or expert system having a relatively small group of candidates to rank from most plausible to least plausible in the third general step of the present invention, as described in subsection C below.

Currently, there are approximately 250 protein structures, determined at 2.0 A or higher resolution, in the public domain. The structures of these very complicated molecules are determined using sophisticated scientific techniques such as X-ray crystallography, neutron diffraction, and nuclear magnetic resonance. Structure determination produces a file of data for each protein. The Brookhaven Protein Data Bank (BPDB) exemplifies a repository of protein structural information. Each file in BPDB contains many records of different types. These records carry the following information:

(1) Name of the protein and standard classification number, (2) Organism from which protein was obtained, (3) Name and address of contributor, (4) Amino-acid sequence of each polypeptide chain, if known, (5) Connectivity of disulfides, if any, (6) Names and connectivities of any prosthetic groups, if any, (7) References to literature, (8) Transformation from reported coordinates to crystallographic coordinates, (9) Coordinates of each atom determined.

There is at least one record for each atom for which a coordinate was determined. Some parts of some proteins are disordered and do not diffract X-rays, so no sensible coordinates can be given. Thus there may be amino acids in the sequence for which only some or none of the atoms have coordinates. Coordinates are given in Angstrom units (100,000,000 A=1 cm) on a rectangular Cartesian grid. As some parts of a protein may adopt more than one spatial configuration, there may be two or more coordinates for some atoms. In such cases, fractional occupancies are given for each alternative position. Atoms move about, some more freely than others. X-ray data can give an estimate of atomic motion which is reported as a temperature (a.k.a. Debye-Waller) factor.

Any other data base which included, implicitly or explicitly, the following data would be equally useful:

(1) Amino acid sequence of each polypeptide chain,
(2) Connectivity of disulfides, if any,
(3) Names and connectivities of any prosthetic groups, if any,
(4) Coordinates (x, y, z) of each atom in each observed configuration,
(5) Fractional occupancy of each atom,
(6) Temperature factor of each atom.

Proteins usually exist in aqueous solution. Although protein coordinates are almost always determined for proteins in crystals, direct contacts between proteins are quite rare. Protein crystals contain from 20% to 90% water by volume. Thus one usually assumes that the structure of the protein in solution will be the same as that in the crystal. It is now generally accepted that the solution structure of a protein will differ from the crystal structure only in minor details. Thus, given the coordinates of the atoms, one can calculate quite easily the solvent accessibility of each atom.

In addition, the coordinates implicitly give the charge distribution throughout the protein. This is of use in estimating whether a hypothetical molecule (made of native protein and one or more linkers) will fold as designed. The typical protein whose structure is known comprises a chain of amino acids (there are 21 types of amino acids) in the range of 100 to 300 amino acids.

Each of these amino acids alone or in combination with the other amino acids as found in the known protein molecule can be used as a fragment to bridge the two sites. The reason that known protein molecules are used is to be able to use known protein fragments for the linker or bridge.

Even with only 250 proteins of known structure, the number of possible known fragments is very large. A linker can be from one to twenty or thirty amino acids long. Let "Lmax" be the maximum number of amino acids allowed in a linker, for example, Lmax might be 25. Consider a protein of "Naa" amino acids. Proteins have Naa in the range 100 to 800, 250 is typical. From this protein one can select Naa-1 distinct two-amino-acid linkers, Naa-2 distinct three-amino acid linkers, ... and (Naa+1−Lmax) distinct linkers containing exactly Lmax amino acids. The total number of linkers containing Lmax or fewer linkers is "Nlink,"

$$Nlink = \sum_{j=1,Lmax} (Naa + 1 - j) =$$

$$Naa \times (Lmax) - (Lmax \times Lmax)/2 + Lmax/2$$

If Naa is 250 and Lmax is 25, Nlink will be 5975. If the number of known proteins is "Nprot," then the total number of linkers, "Nlink total" will be $$Nlink\_total = \sum_{k=1,Nprot} \sum_{j=1,Lmax} (Naa(k) + 1 - j)$$

$$= \sum_{k=1,Nprot} (Naa(k) \times (Lmax) -$$

$$(Lmax \times Lmax)/2 + Lmax/2]$$

$$= Nprot \times (Lmax/2 - Lmax \times$$

$$Lmax)/2 + Lmax \times \sum_{k=1,Nprot} Naa(k)$$

Where Naa(k) is the number of amino acids in the kth protein. With 250 proteins, each containing 250 amino acids (on average), and Lmax set to 25, Nlink total is 1,425,000.

This is the number of linkers of known structure. If one considers the number of possible amino acid sequences up to length Lmax (call it "Nlink-possible"), it is much larger.

$$Nlink\_possible = \sum_{J=1,Lmax} 20^J$$

For $Lmax = 25$ $Nlink\_possible = 353, 204, 547, 368, 421, 052, 631,$ $578, 947, 368, 420$ $= 3.53 * 10^{32}$ Using known peptide fragments thus reduces the possibilities by twenty-six orders of magnitude. Appropriate searching through the known peptide fragments reduces the possibilities a further five orders of magnitude.

Essentially, the present invention utilizes a selection strategy for reducing a list of possible candidates. This is done as explained below in a preferred form in a three step process. This three step process, as is illustrated in the explanation of the each of the three steps of the process, significantly reduces the computer time required to extract the most promising candidates from the data base of possible candidates. This should be contrasted with a serial search throughout the entire data base of candidates, which would require all candidates to be examined in total. The present invention examines certain specific parameters of each candidate, and uses these parameters to produce subgroups of candidates that are then examined by using other parameters. In this way, the computer processing speed is significantly increased.

The best mode of the present invention uses a protein data base created and supplemented by the Brookhaven National Laboratory in Upton, Long Island, N.Y. This data base is called the Brookhaven Protein Data Base (BPDB). It provides the needed physical and chemical parameters that are needed by the present invention. It should be understood, that the candidate linkers can be taken from the Brookhaven Protein Data Base or any other source of three-dimensional protein structures. These sources must accurately represent the proteins. In the current embodiment, X-ray structures determined at resolution of 2.5A or higher and appropriately refined were used. Each peptide is replaced (by least-squares fit) by a standard planar peptide with standard bond lengths and angles. Peptides which do not accurately match a standard peptide (e.g., cis peptides) are not used to begin or end linkers, but may appear in the middle.

Each sequence up to some maximum number of amino acids (Lmax) is taken as a candidate. In the preferred embodiment, the maximum number of amino acids (Lmax) is set to 30. However, the present invention is not limited to this number, but can use any maximum number that is desired under the protein engineering circumstances involved.

Figure 9:
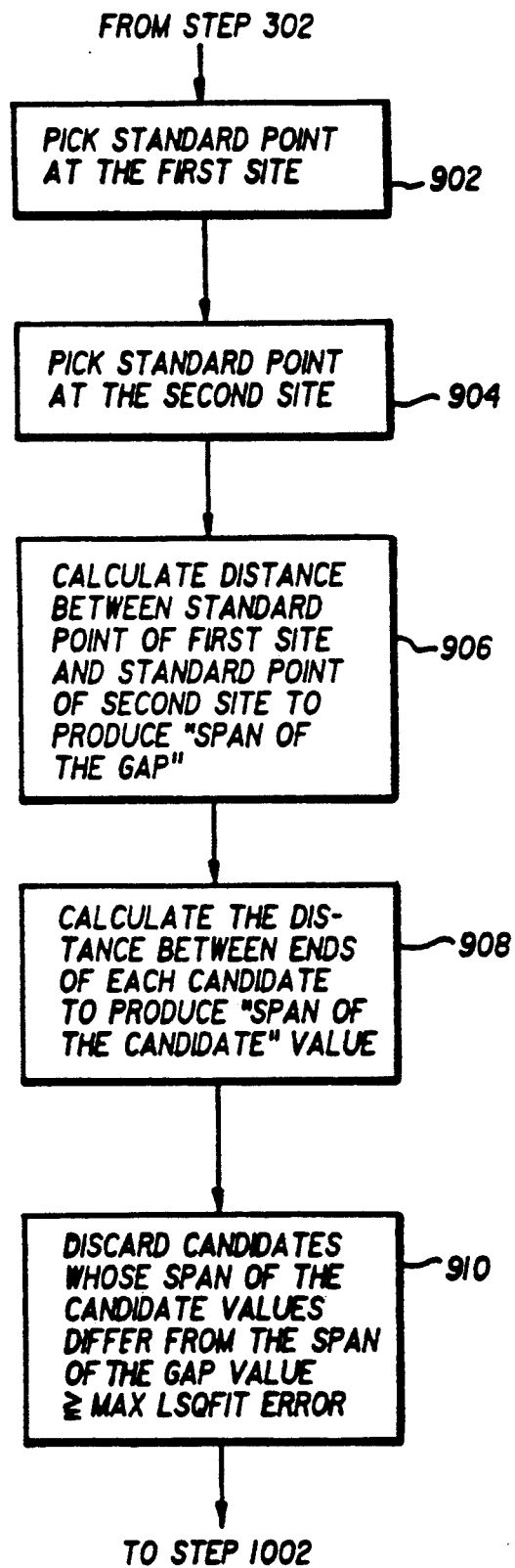
FIG. 9 shows a block diagram of candidate selection for correct span.

1. Selecting Candidates with Proper Distance Between the N Terminal and the C Terminal The first step in the selection of candidates step is to select the candidate linkers with a proper distance between the N terminal and the C terminal from all of the candidate linkers that exist in the protein data base that is being used. FIG. 9 shows in block diagram form the steps that make up this candidate selection process utilizing distance as the selection parameter.

Referring to FIG. 9, a standard point relative to the peptide unit at the first site is selected, as shown by block 902.

A standard point relative to the peptide unit in the second site is also picked, as indicated by a block 904. Note that in the best mode the geometric centers of the peptide units of the first and second sites are used, but any other standard point can be utilized, if desired.

The distance between the standard points of the two peptides at the first and second sites defining the gap to be bridged by the linker is then calculated, as indicated by block 906. This scalar distance value is called the span of the gap. Note that this scalar value does not include any directional information.

Next, as indicated by a step 908, the distance between the ends of the possible linker candidates are calculated. The distance between the ends of a particular candidate is called the span of the candidate. Note that each possible linker candidate has a span of the candidate scalar value.

The final step in the distance selection candidate selection process is that of a step 910. In step 910, candidates are discarded whose span of the candidate values differ from the span of the gap value by more than a preselected amount (this preselected amount is Max LSQFIT error). In the best mode of the present invention, the preselected amount for Max LSQFIT error is 0.50 Angstroms. However, any other suitable value can be used.

The preceding discussion has been for a single gap. In fact, the expert user often selects several gaps and the search uses all of them. The span of each candidate is compared to the span of each gap until it matches one, within the preset tolerance, or the list of gaps is exhausted. If the candidate matches none of the gaps, it is discarded. If it matches any gap it is carried to the next stage.

The inventors have determined that the use of the distance as the first parameter for discarding possible linker candidates results in a significant reduction in the number of possible candidates with a minimum amount of computer time that is needed. In terms of the amount of reduction, a representative example (using linkers up to 20 amino acids) starts out with 761,905 possible candidates that are in the protein data base. This selection of candidates using the proper distance parameter winnows this number down to approximately 63,727 possible candidates. As is discussed below, the distance selection operation requires much less computer time than is required by the other two steps which make up this selection step 304.

The result of this selection of candidates according to proper distance is a group (called a first group of candidates) which exhibit a proper length as compared to the gap that is to be bridged or linked. This first group of candidates is derived from the protein data' base using the distance criteria only.

2. Selecting Candidates with Proper Direction from N Terminal to C Terminal

This substep essentially creates a second group of possible candidates from the first group of possible candidates which was produced by the distance selection substep discussed in connection with FIG. 9. The second group of candidates is selected in accordance with the orientation of the C terminal residue (i.e., the final residue) of the linker with respect to the N terminal residue (i.e., the initial residue) which is compared to the orientation of the C terminal residue (i.e., the second site) of the gap with respect to the N terminal residue (i.e., the first site). See FIG. 20B. In this way, this direction evaluation determines if the chain of the linker ends near the second site of the gap, when the amino terminal amino acid of the linker is superimposed on the first site of the gap so as to produce the minimum amount of unwanted molecular distortion.

Figure 10:
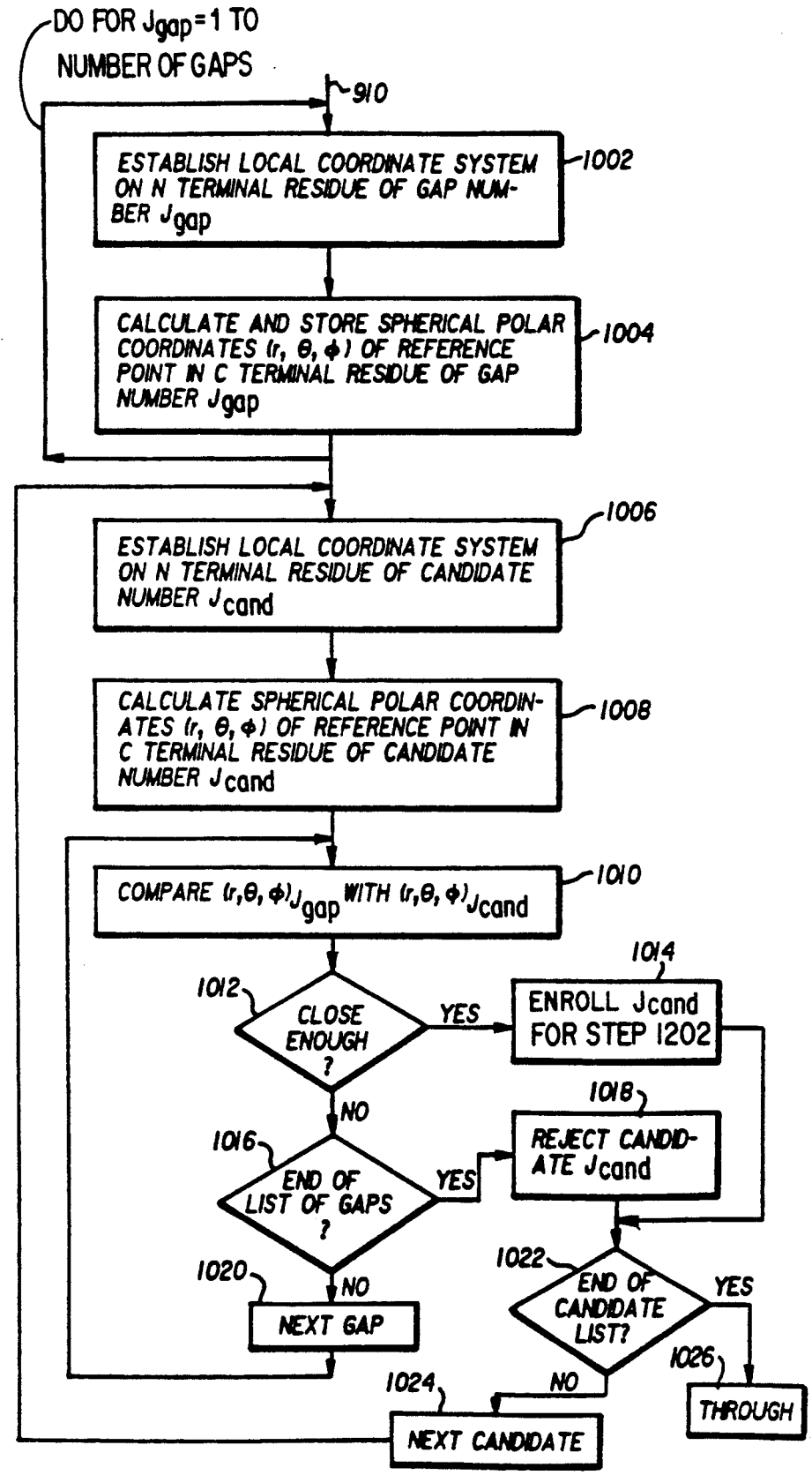
FIG. 10 shows a block diagram of candidate selection for correct direction from N terminal to C terminal.

Referring now to FIG. 10, the first step used in producing the second group of possible candidates is a step 1002. In step 1002 a local coordinate system is established on the N terminal residue of one of the selected gaps. For example, one might take the local X-axis as running from the first alpha carbon of the N terminal residue to the second alpha carbon of the N terminal residue, with the first alpha carbon at the origin the second alpha carbon on the plus X-axis. The local Y-axis is selected so that the carbonyl oxygen lies in the xy plane with a positive y coordinate. The local Z-axis is generated by crossing X into Y. Next, as indicated by step 1004, a standard reference point in the C terminal residue of the gap is located and its spherical polar coordinates are calculated in the local system. The standard reference point could be any of the atoms in the C terminal peptide (throughout this application, peptide, residue, and amino acid are used interchangeably) or an average of their positions. Steps 1002 and 1004 are repeated for all gaps in the list of gaps. As indicated by step 1006, a local coordinate system is established on the N terminal residue of one of the candidates. This local coordinate system must be established in the same manner used for the local coordinate systems established on each of the gaps. Various local systems could be used, but one must use the same definition throughout. In step 1008, the standard reference point is found in the C terminal residue of the current candidate. This standard point must be chosen in the same manner used for the gaps. The spherical polar coordinates of the standard point are calculated in the local system of the candidate. (This use of local coordinate system is completely equivalent to rotating and translating all gaps and all candidates so that their initial peptide lies in a standard position at the origin.) In step 1010, the spherical polar coordinates of the gap vector (r, theta, phi) are compared to the spherical polar coordinates of the candidate vector (r, theta, phi). In step 1012 a preset threshold is applied, if the two vectors agree closely enough, then one proceeds to step 1014 and enrolls the candidate in the second group of candidates. Currently, this preset threshold is set to 0.5 Å, but other values could be used. From step 1014, one skips forward to step 1022, vide infra. On the other hand, if the vectors compared in step 1012 are not close enough, one moves to the next gap vector in the list, in step 1016. If there are no more gaps, one goes to step 1018 where the candidate is rejected. If there are more gaps, step 1020 increments the gap counter and one returns to step 1010. From steps 1014 or 1018 one comes to step 1022 where one tests to see if all candidates have been examined. If not, step 1024 increments the candidate counter and one returns to step 1006. If all candidates have been examined, one has finished, step 1026.

Figure 11A:
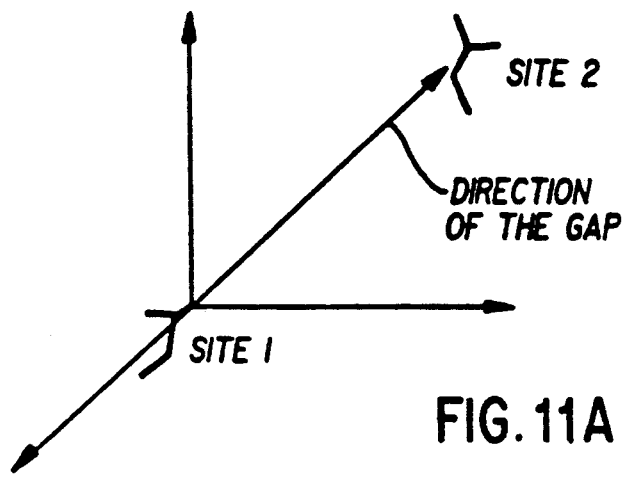
FIG. 11 shows a comparison of direction of a gap to direction of a candidate.
Figure 11B:
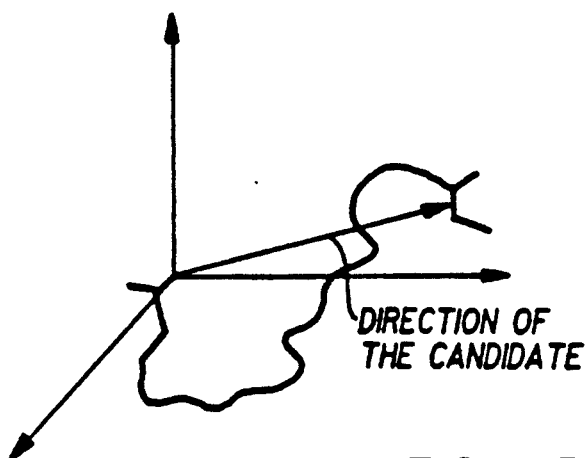
Figure 11C:
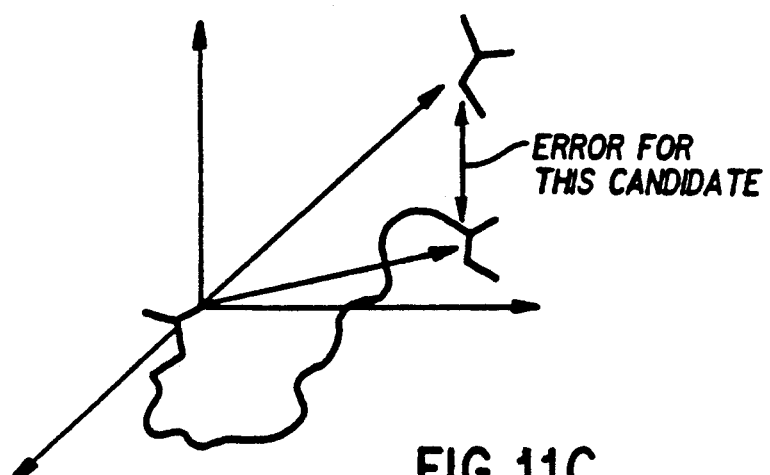

FIG. 11 shows the concept of comparing the direction of the gap to the direction of the candidate.

The inventors have determined that in the example discussed above where 761,905 possible candidates are in the protein data base, the winnowing process in this step reduces the approximate 63,727 candidates in the first group to approximately 50 candidates in the second group. The inventors have also determined that as referenced to the units of computer time referred to above in connection with the scalar distance parameter, it takes approximately 4 to 5 computer units of time to perform the selection of this step. Thus, it can be appreciated that it preserves computer time to perform the distance selection first, and the direction selection second since the direction selection process takes more time than the distance selection process.

3. Selecting Candidates with Proper Orientation at Both Termini

Figure 12:
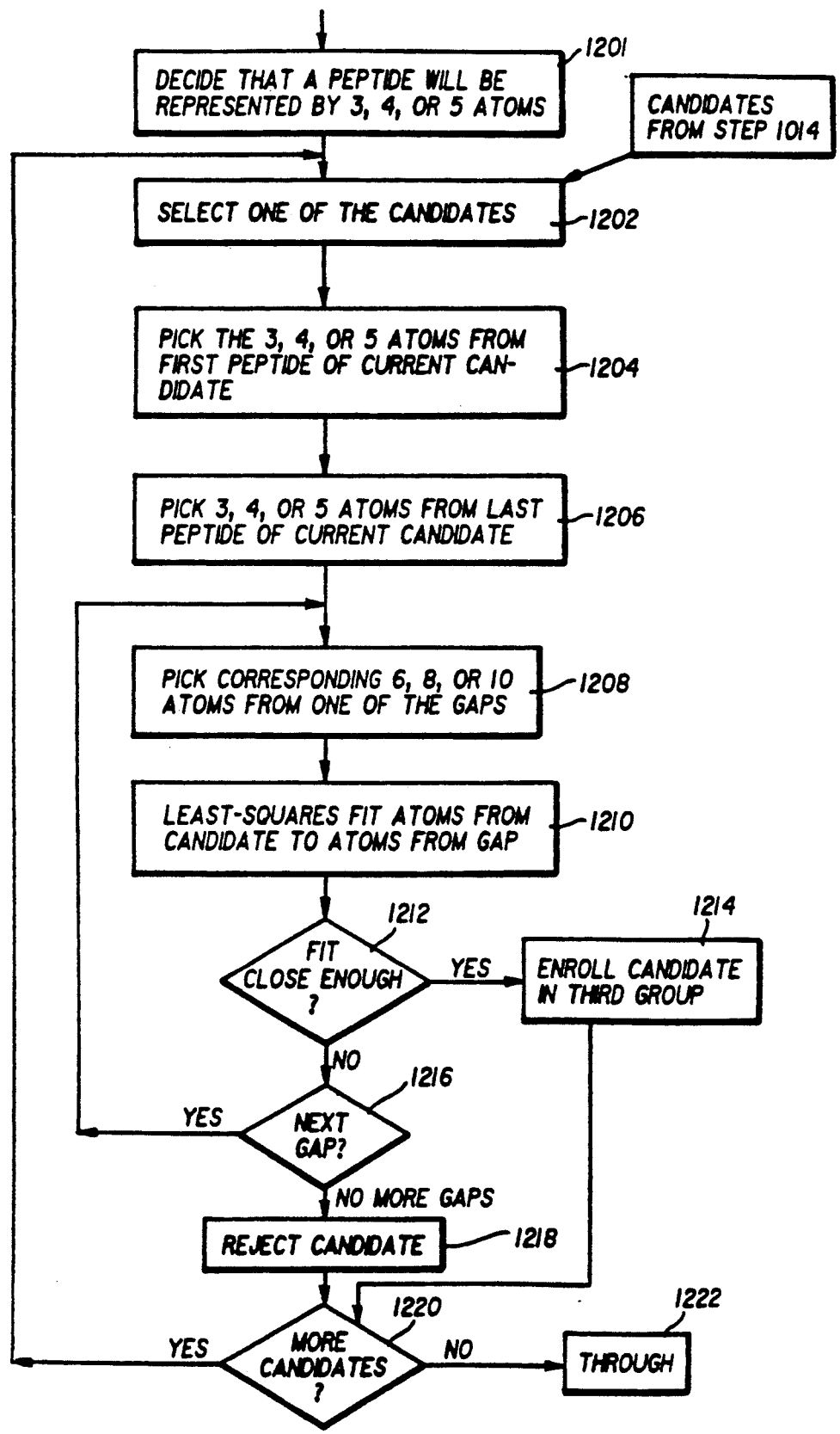
FIG. 12 shows a block diagram of candidate selection for correct orientation at both ends.

In this step, the candidates in the second group of step 1016 of FIG. 10 are winnowed down to produce a third group of plausible candidates using an evaluation of the relative orientation between the peptide groups at either end of the candidate, compared to the relative orientation between the peptide groups at either end of the gap. In a step 1201, (FIG. 12) decide that a peptide will be represented by 3, 4, or 5 atoms (vide infra). Specifically, in a step 1202', one of the candidates in the second group (step 1014) is selected for testing. In a step 1204, three to five atoms in the first peptide are selected to define the orientation of the first peptide. So long as the atoms are not collinear, three atoms is enough, but using four or five atoms makes the least-squares procedure which follows over-determined and therefore compensates for errors in the coordinates. For example, assume selection of four atoms: C alpha, C, N, and C beta. Next, in a step 1206, one selects the corresponding 3, 4, or 5 atoms from the final peptide of the selected candidate. These 6, 8, or 10 atoms define a three-dimensional object. In a step 1208, select one of the gaps. Select the corresponding 6, 8, or 10 atoms from the gap. In a step 1210, least-squares fit the atoms from the candidate to the atoms from the gap. This least-squares fit allows degrees of freedom to superimpose the two three-dimensional objects. Assume that one object is fixed and the other is free to move. Three degrees of freedom control the movement of the center of the free object. Three other degrees of freedom control the orientation of the free object. In a step 1212, the result of the least-square fit is examined. If the Root-Mean-Square (RMS) error is less than some preset threshold, the candidate is a good fit for the gap being considered and is enrolled in the third group in a step 1214. If, on the other hand, the RMS error is greater than the preset threshold, one checks to see if there is another gap in the list in a step 1216. If there is, one selects the next gap and returns to step 1208. If there are no more gaps in the list, then the current candidate from the second group is rejected in step 1218. In step 1220, one checks to see if there are more candidates in the second group; if so, a new candidate is selected and one returns to step 1201. If there are no more candidates, one is finished (step 1222). Again referring to a representative case, where linkers of length up to twenty amino acids were sought for a single gap with separation 12.7 A, the protein data bank contained 761,905 potential linkers. Of these, 63,727 passed the distance test. The direction test removed all but 50 candidates. The orientation test passed only 1 candidate with RMS error less than or equal to 0.5 A. There were two additional candidates with RMS error between 0.5 A and 0.6 A. Moreover, the inventors have determined that it takes about 25 units of computer time to evaluate each candidate in group 2 to decide whether they should be selected for group 3. It can be appreciated now that the order selected by the inventors for the three steps of winnowing the candidates has been selected so that the early steps take less time per candidate than the following steps. The order of the steps used to select the candidate can be changed, however, and still produce the desired winnowing process. Logically, one might even omit steps one and two and pass all candidates through the least-squares process depicted in FIG. 12 and achieve the same list of candidates, but at greater cost in computing. This may be done in the case of parallel processing where computer time is plentiful, but memory is in short supply.

Another approach (not illustrated) for determining whether the proper orientation exists between the ends of the candidate, is to examine only the atoms at the C terminal of the candidate as compared to the atoms at the final peptide of the gap. In step 2, the inventors aligned the first peptide of the candidate with the first peptide in the gap. Having done this, one could merely compare the atoms at the C terminal of the candidate with the atoms of the second peptide of the gap. This approach is inferior to that discussed above because all the error appears at the C terminus, while the least-squares method discussed above distributes the errors evenly.

C. Ranking and Eliminating Candidates

As shown in FIG. 3, the third general step in the present invention is that of ranking the plausible candidates from most plausible to least plausible, and eliminating those candidates that do not appear to be plausible based on criteria utilized by an expert operator and/or expert system.

In the best mode, the candidates in the third group (step 1214) are provided to the expert operator, who can sequentially display them in three dimensions utilizing the computer-graphics display system 116. The expert operator then can make decisions about the candidates based on knowledge concerning protein chemistry and the physical relationship of the plausible candidate with respect to the gap being bridged. This analysis can be used to rank the plausible candidates in the third group from most plausible to least plausible. Based on these rankings, the most plausible candidates can be selected for genetic engineering.

As noted above in connection with the illustrative example, there are typically few (under 100) candidates which make it to the third group of step 1214. Consequently, a moderately expert operator (one having a Bachelor of Science degree in chemistry, for example), can typically winnow down this number of plausible candidates to a group of 10 to 15. Thereafter, a more expert operator and/or expert system can further winnow down the number. In this way, only a very few of the plausible candidates needs to be tested in practice as compared to the hundreds, thousands or more of candidates that would have to be tested if no selection process like that of the present invention was used. This speeds up the process of engineering the single chain molecules by orders of magnitude, while reducing costs and other detriments by orders of magnitude as well.

In certain situations, however, automatic ranking in this third general step may be warranted. This could occur, for example, where the expert operator was presented with quite a few candidates in the third group, or where it is desired to assist the expert operator in making the ranking selections and eliminating candidates based on prior experience that has been derived from previous engineering activities and/or actual genetic engineering experiments.

Figure 13:
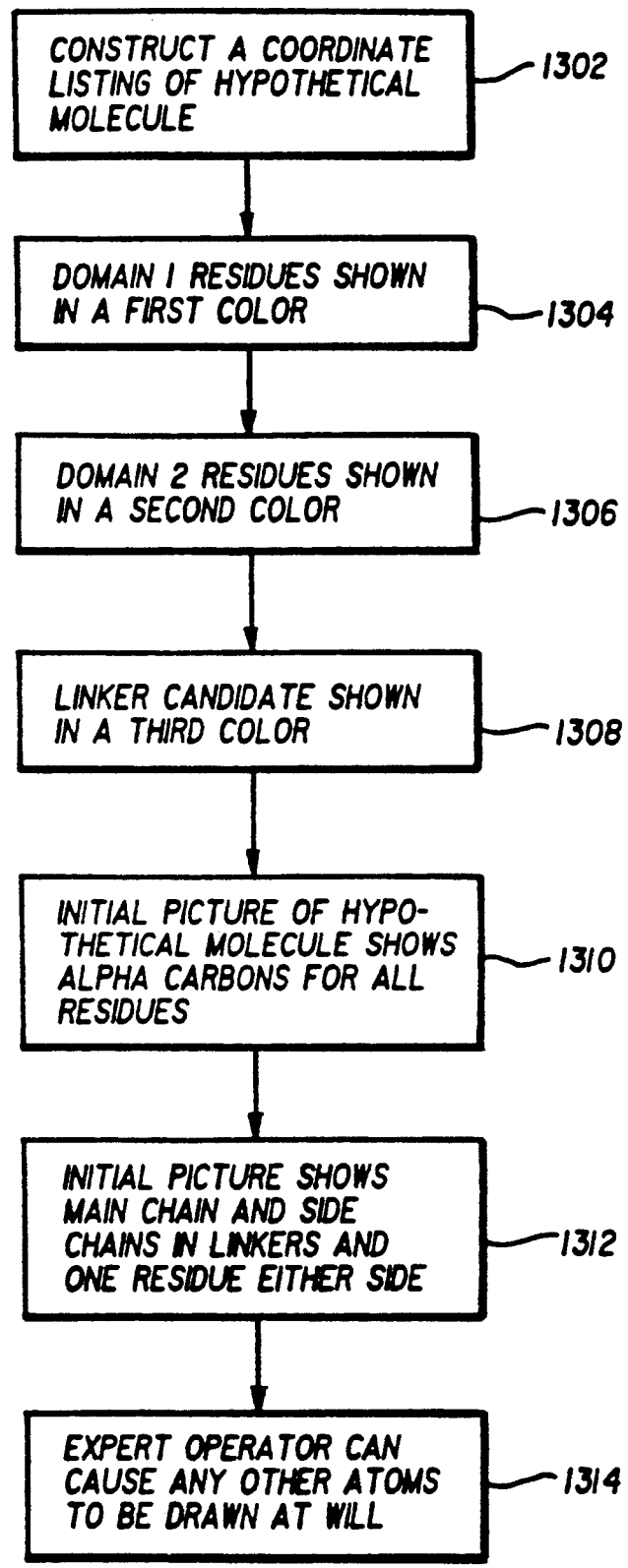
FIG. 13 shows a block diagram of selection of sites for the two-linker embodiment.

Referring now to FIG. 13, a coordinate listing of the hypothetical molecule (candidate) is automatically constructed, as is indicated by a block 1302. The expert operator can then display using a first color the residues from domain 1 of the native protein. Color display 120 can provide a visual indication to the expert operator of where the residues lie in domain 1. This is indicated by a block 1304.

The expert operator then can display on color display 120 the residues from domain 2 of the native protein using a second color, as is indicated by a block 1306. The use of a second color provides a visual indication to the user which assists in distinguishing the residues from domain 1 from the residues from domain 2.

The linker (candidate) being ranked can be displayed in a selected color, which color can be different from the first color of step 1304 and/or the second color from step 1306. Again, by using this visual color indication, the expert operator can distinguish the residues of domain 1 and 2 of the native protein. This display of the linker candidate is indicated by a block 1308.

The initial picture on the color display 120 provided to the expert operator typically shows the alpha carbons for all of the residues. This is indicated by a block 1310. In addition, the initial picture shows the main-chain and side-chains for residues and linkers and one residue before the linker and one residue after the linker. This is indicated by a block 1312.

The expert operator can also cause any of the other atoms in the native protein or linker candidate to be drawn at will. The molecule can be rotated, translated, and enlarged or reduced, by operator command, as was discussed generally in connection with the computer-graphics display system 116 above. The block diagram of FIG. 13 indicates that each of the steps just discussed are accomplished in serial fashion. However, this is only for purposes of illustration. It should be understood that the operator can accomplish any one or more of these steps as well as other steps at will and in any sequence that is desired in connection with the ranking of the plausible candidates in group 3.

Figure 14:
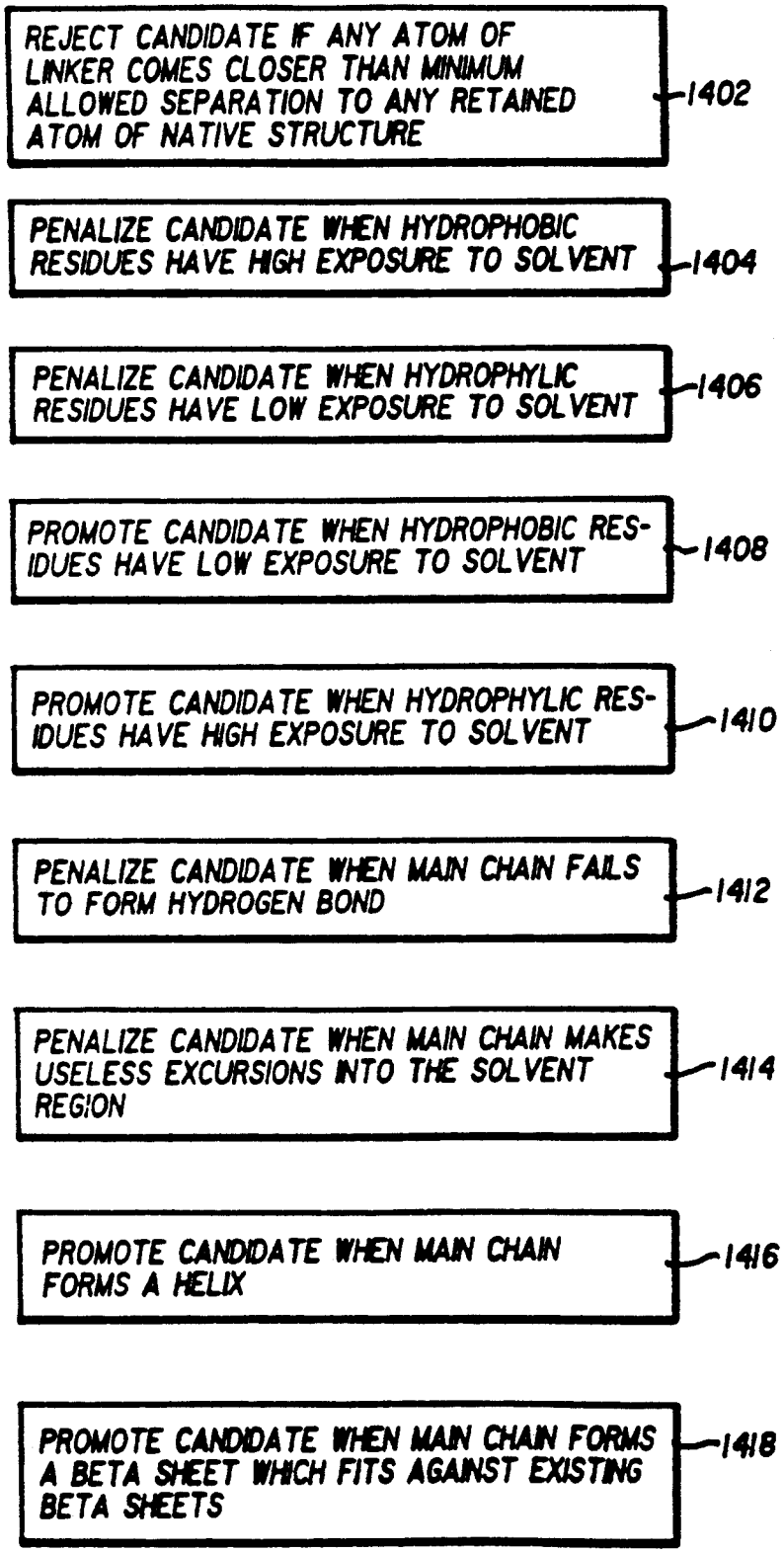
FIG. 14 shows examples of rules by which candidates may be ranked.

The expert operator and/or expert system utilized in this third general step in ranking the candidates from most plausible to least plausible and in eliminating the remaining candidates from group 3, can use a number of different rules or guidelines in this selection process. Representative of these rules and guidelines are the following which are discussed in connection with FIG. 14. Note that the blocks in FIG. 14 show the various rules and/or criteria, which are not necessarily utilized in the order in which the boxes appear. The order shown is only for purposes of illustration. Other rules and/or criteria can be utilized in the ranking process, as well.

As shown in step 1402, a candidate can be rejected if any atom of the linker comes closer than a minimum allowed separation to any retained atom of the native protein structure. In the best mode, the minimum allowed separation is set at 2.0 Angstroms. Note that any other value can be selected. This step can be automated, if desired, so that the expert operator does not have to manually perform this elimination process.

A candidate can be penalized if the hydrophobic residues have high exposure to solvent, as is indicated by a block 1404. The side chains of phenylalanine, tryptophan, tyrosine, leucine, isoleucine, methionine, and valine do not interact favorably with water and are called hydrophobic. Proteins normally exist in saline aqueous solution; the solvent consists of polar molecules ($H_2O$) and ions.

A candidate can be penalized when the hydrophilic residues have low exposure to solvent. The side chains of serine, threonine, aspartic acid, glutamic acid, asparagine, glutamine, lysine, arginine, and proline do interact favorably with water and are called hydrophilic. This penalization step for hydrophilic residues is indicated by a block 1406.

A candidate can be promoted when hydrophobic residues have low exposure to solvent, as is indicated by a block 1408.

A candidate can be promoted when hydrophilic residues have high exposure to solvent, as indicated by a block 1410.

A candidate can be penalized when the main chain fails to form hydrogen bonds, as is indicated by a block 1412.

A candidate can be penalized when the main chain makes useless excursions into the solvent region. Useless excursions are those which do not make any evident interaction with the retained native protein. This is indicated by a block 1414.

A candidate can be promoted when the main chain forms a helix, as is indicated by a block 1416. Helices are self-stabilizing. Thus a linker which is helical will be more stable because its main-chain polar atoms (0 and N) will form hydrogen bonds within the linker.

As is indicated by a block 1418, a candidate can be promoted when the main chain forms a beta sheet which fits against existing beta sheets. The strands of beta sheets stabilize each other. If a linker were found which was in a beta-sheet conformation such that it would extend an existing beta sheet, this interaction would stabilize both the linker and the native protein.

Another expert design rule penalizes candidates which have sterically bulky side chains at undesirable positions along the main chain. Furthermore, it is possible to "save" a candidate with a bulky side chain by replacing the bulky side chain by a less bulky one. For example if a side chain carries a bulky substituent such as leucine or isoleucine, a possible design step replaces this amino acid by a glycine, which is the least bulky side chain.

Other rules and/or criteria can be utilized in the selection process of the third general step 306, and the present invention is not limited to the rules and/or criteria discussed. For example, once the linker has been selected it is also possible to add, delete, or as stated, modify one or more amino acids therein, in order to accomplish an even better 3-D fit.

IV. Double and Multiple Linker Embodiments

Section III above described the single linker embodiment in accordance with the present invention. This section describes double linker and multiple linker embodiments in accordance with the present invention. For brevity purposes, only the significant differences between this embodiment and the single linker embodiment will be described here and/or illustrated in separate figures. Reference should therefore be made to the text and figures that are associated with the single linker embodiment.

A. Plausible Site Selection

The two main goals of minimizing distance between the sites to be linked and the least loss of native protein apply in the site selection in the double and multiple linker embodiments as they did apply in the single linker embodiment discussed above.

Figure 15A:
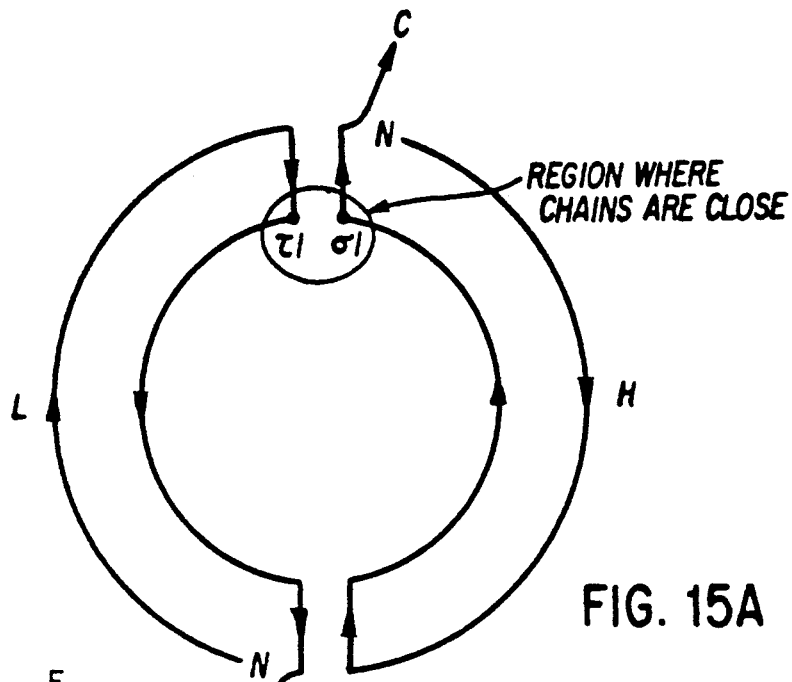
FIG. 15A shows a two-dimensional simplified representation of the variable domain of an $F_v$ light chain, L, and the variable domain of an $F_v$ heavy chain, H, showing the first two sites to be linked.
Figure 15B:
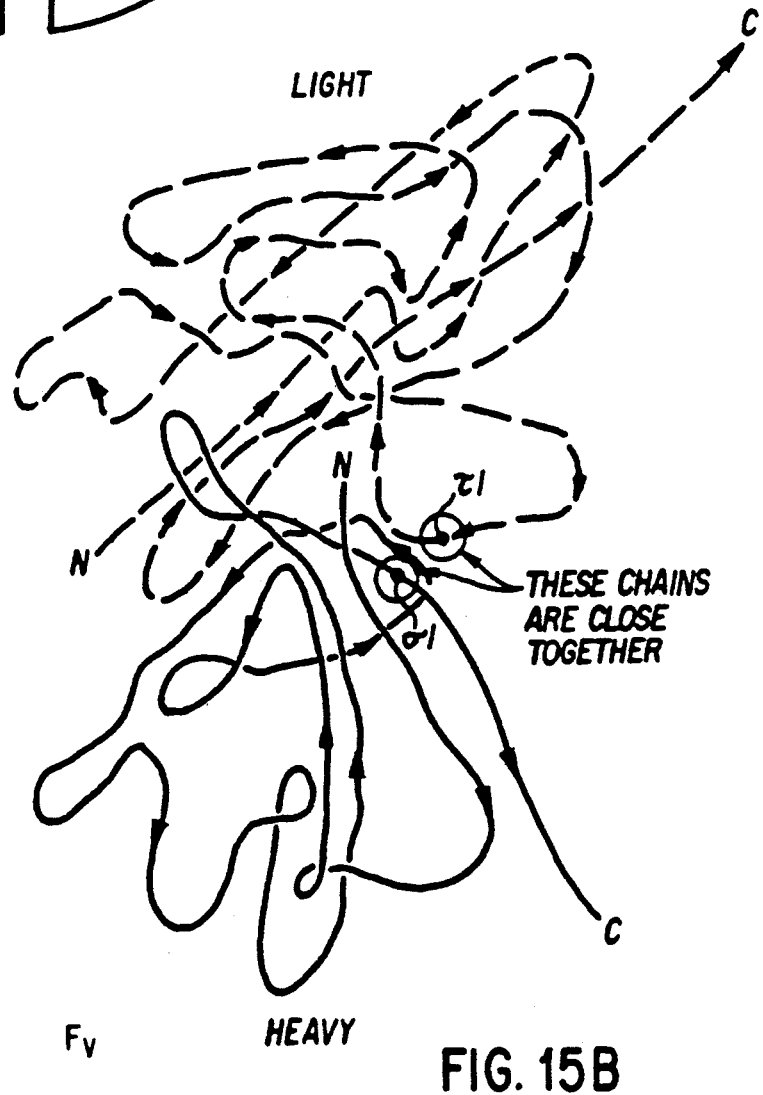
FIG. 15B shows a two-dimensional representation of the three-dimensional relationships between the variable domain of an $F_v$ light chain, L, and the variable domain of an $F_v$ heavy chain, H, showing the regions in which the second sites to be linked can be found and the linker between the first pair of sites.

FIG. 15A shows a simplified two dimensional representation of the use of two linkers to create the single polypeptide chain from the two naturally aggregated but chemically separate polypeptide chains. FIG. 15B shows in two dimensions a three dimensional representation of the two chains of FIG. 15A. Referring now to FIGS. 15A and B, the first step in determining suitable sites is to find a site in domain 1 which is close to either the C or N terminus of domain 2. For purposes of illustration, and as is shown in FIGS. 15A and 15B, it is assumed that the most promising location is the C terminus of domain 2. The residue in domain 1 is called tau 1, while the residue in domain 2 is called sigma 1.

Figure 16A:
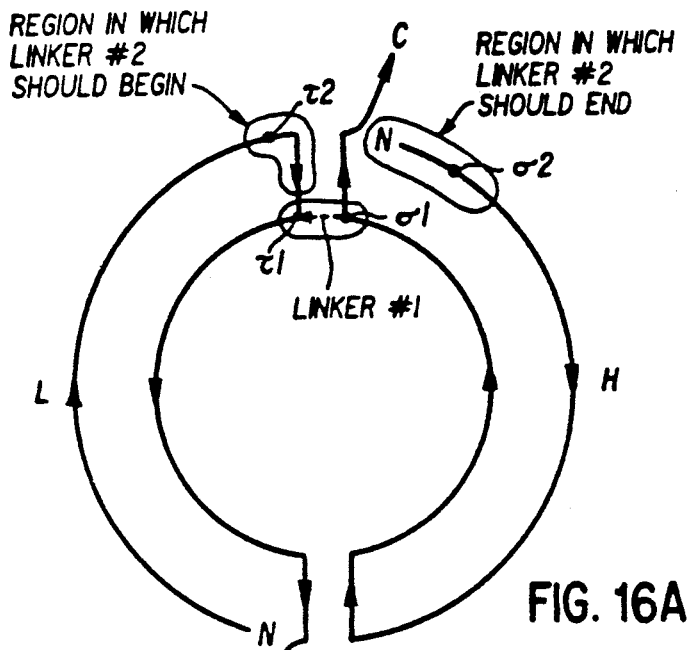
FIG. 16A shows the two-dimensional simplified representation of the variable domain of an $F_v$ light chain, L, and the variable domain of an $F_v$ heavy chain, H, showing the regions in which the second sites to be linked can be found and the linker between the first pair of sites.
Figure 16:
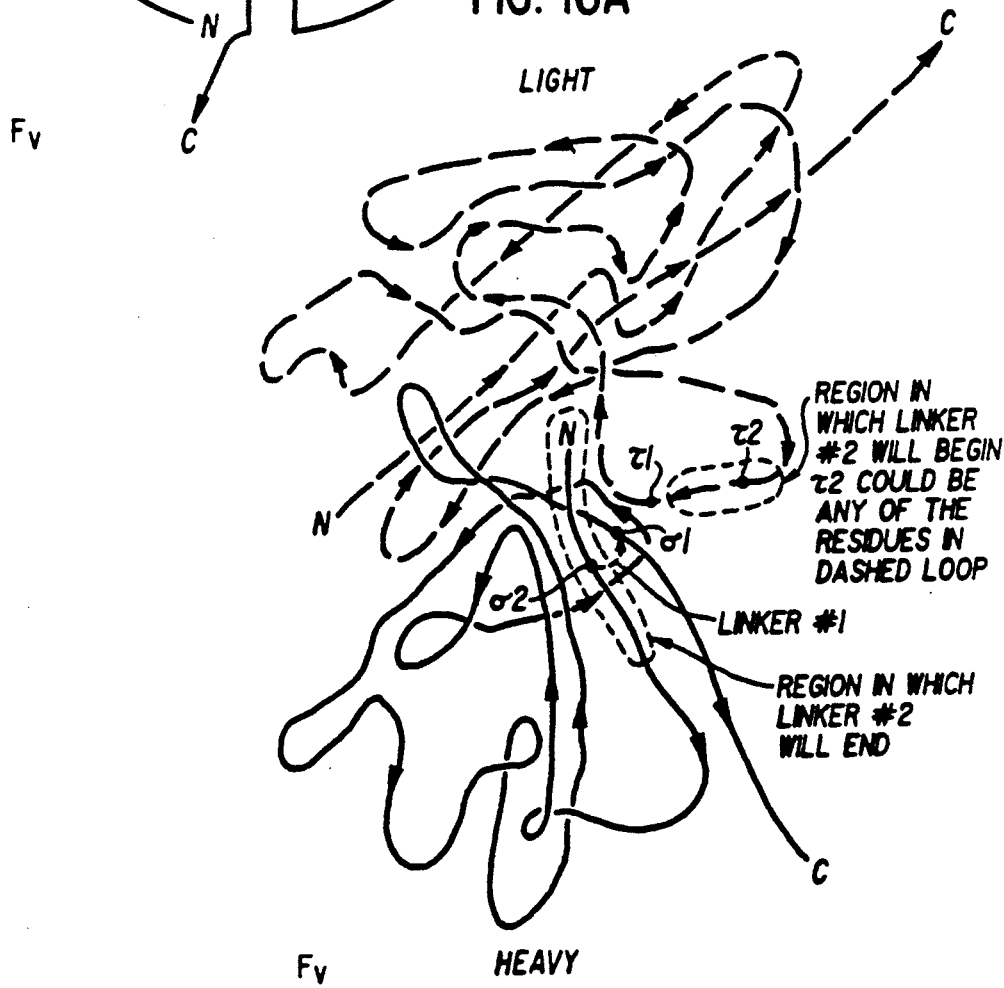
FIG. 16B shows the two-dimensional representation of the three-dimensional relationships between the variable domain of an $F_v$ light chain, L, and the variable domain of an $F_v$ heavy chain, H, showing the regions in which the second sites to be linked can be found and the linker between the first pair of sites.

FIGS. 16A and 16B are respectively two dimensional simplified plots of the two chains, and two dimensional plots of the three dimensional representation of the two chains. They are used in connection with the explanation of how plausible sites are selected for the second linker in the example situation.

The first step in connection with finding plausible sites for the second linker is to find a residue in domain 1 that is before tau 1 in the light chain. This residue is called residue tau 2. It is shown in the top portion in FIG. 16A, and in the right middle portion in FIG. 16B.

The next step in the site selection process for the second linker is to find a residue in domain 2 near the N terminus of domain 2. This residue is called residue sigma 2. Reference again is made to FIGS. 16A and B to show the location of sigma 2.

Figure 17A:
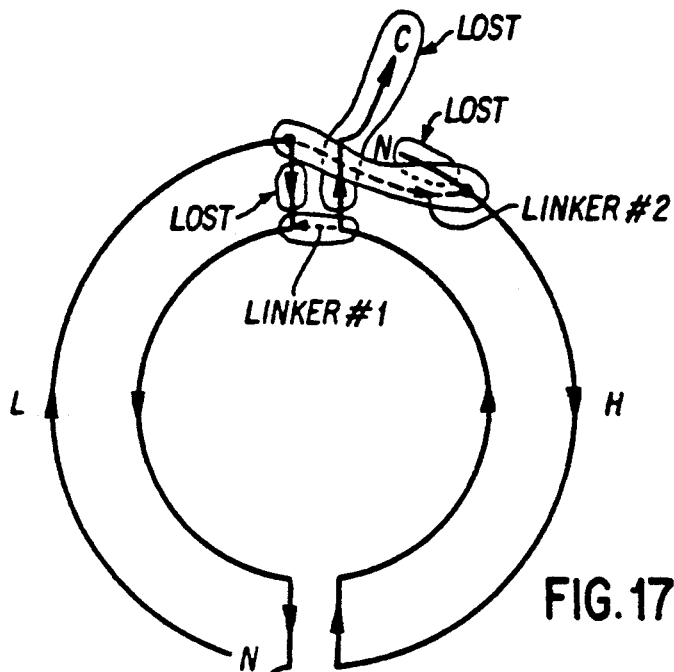
FIG. 17A shows the two-dimensional simplified representation of the variable domain of an $F_v$ light chain, L, and the variable domain of an $F_v$ heavy chain, H, showing the second linker and the portions of the native protein which are lost.
Figure 17B:
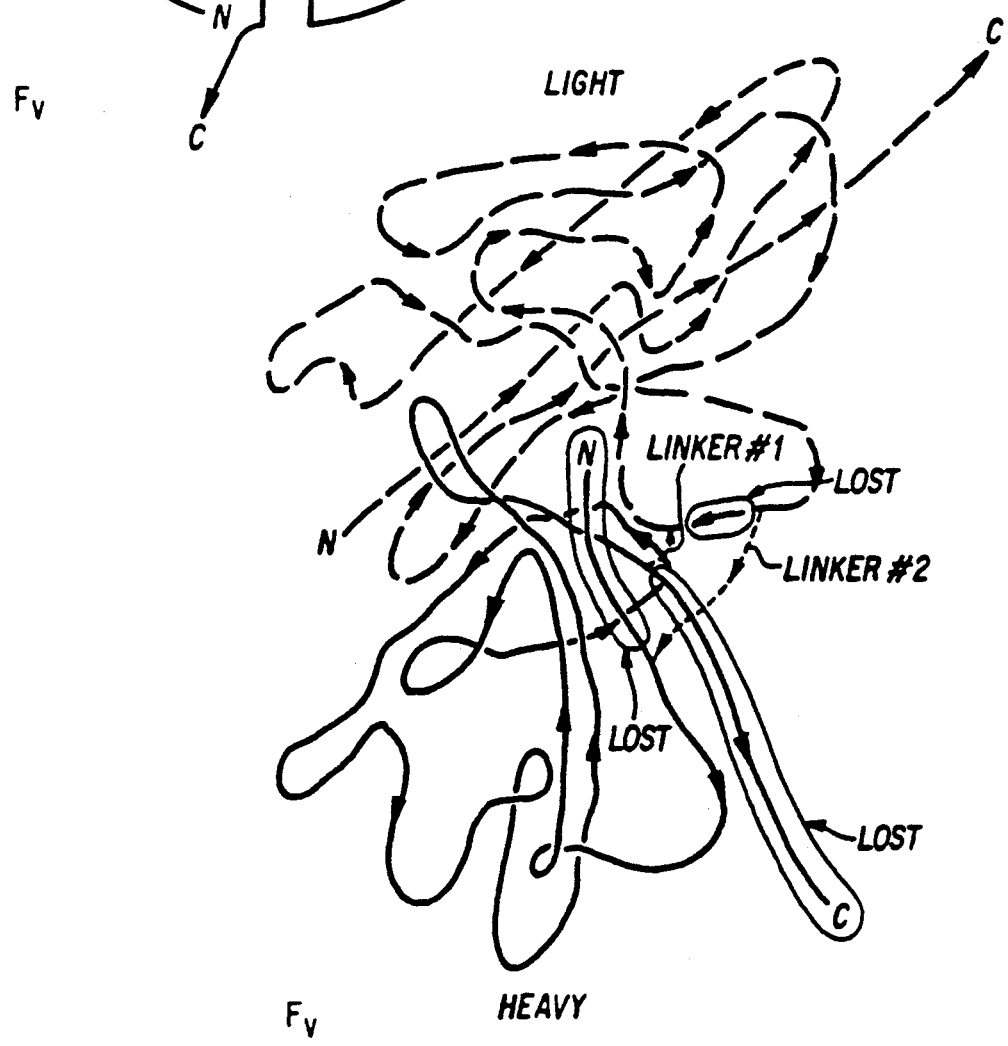
FIG. 17B shows the two-dimensional representation of the three-dimensional relationships between the variable domain of an $F_v$ light chain, L, and the variable domain of an $F_v$ heavy chain, H, showing the second linker and the portions of native protein which are lost.
Figure 18:
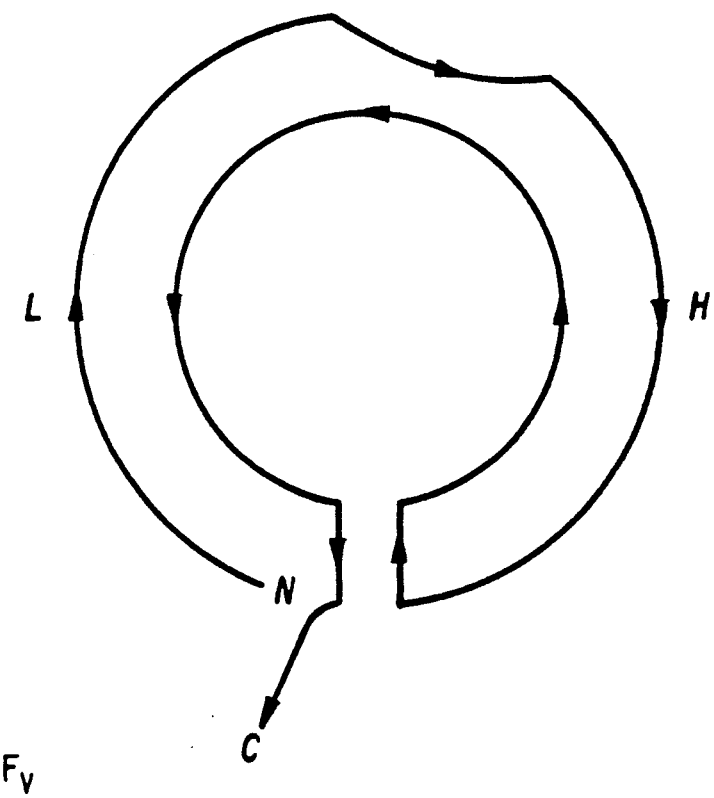
FIG. 18 shows the two-dimensional simplified representation of the variable domain of an $F_v$ light chain, L, and the variable domain of an $F_v$ heavy chain, H, showing the complete construction.

The second linker (linker 2) thus runs from tau 2 to 2. This is shown in FIGS. 17A and 17B. Note that the chain that is formed by these two linkers has the proper direction throughout. FIG. 18 shows in two dimensional simplified form the single polypeptide chain that has been formed by the linking of the two independent chains using the two linkers. Note that the approach outlined above resulted in the minimal loss of native protein. The completely designed protein is shown in FIG. 17 and consists of domain 1 from the N terminal to tau 2, linker 2, domain 2 from sigma 2 to sigma 1, linker 1, and domain 1 from tau 1 to the C terminus. The arrows that are shown in FIG. 17 indicate the direction of the chain.

FIG. 17 shows that the residues lost by the utilization of the two linkers are: (a) from the N terminus of domain 2 up to the residue before sigma 2; and (b) from the residue after sigma 1 to the C terminus of domain 2; and (c) from the residue after tau 2 to the residue before tau 1 of domain 1.

If one of the linkers in the two linker case is very long, one could link from tau 2 to a residue in domain 2 after sigma 1. A third linker (not shown) would then be sought from a residue near the C terminal of domain 2 to a residue near the-N terminal of domain 2.

Additionally, one could use two linkers to reconnect one of the domains in such a way that a single linker or a pair of linkers would weld the two domains into one chain.

B. Candidate Selection and Candidate Reject on Steps

Ranking of linkers in the multilinker cases follows the same steps as in the single linker case except there are some additional considerations.

(1) There may be a plurality of linkers for each of the two (or more) gaps to be closed. One must consider all combinations of each of the linkers for gap A with each of the linkers for gap B.

(2) One must consider the interactions between linkers.

As one must consider combinations of linkers, the ranking of individual linkers is used to cut down to a small number of very promising linkers for each gap. If one has only three candidates for each gap, there are nine possible constructs.

The process of examining interactions between linkers and discarding poor candidates can be automated by applying the rules discussed above.

V. Parallel Processing Embodiment

Figure 19:
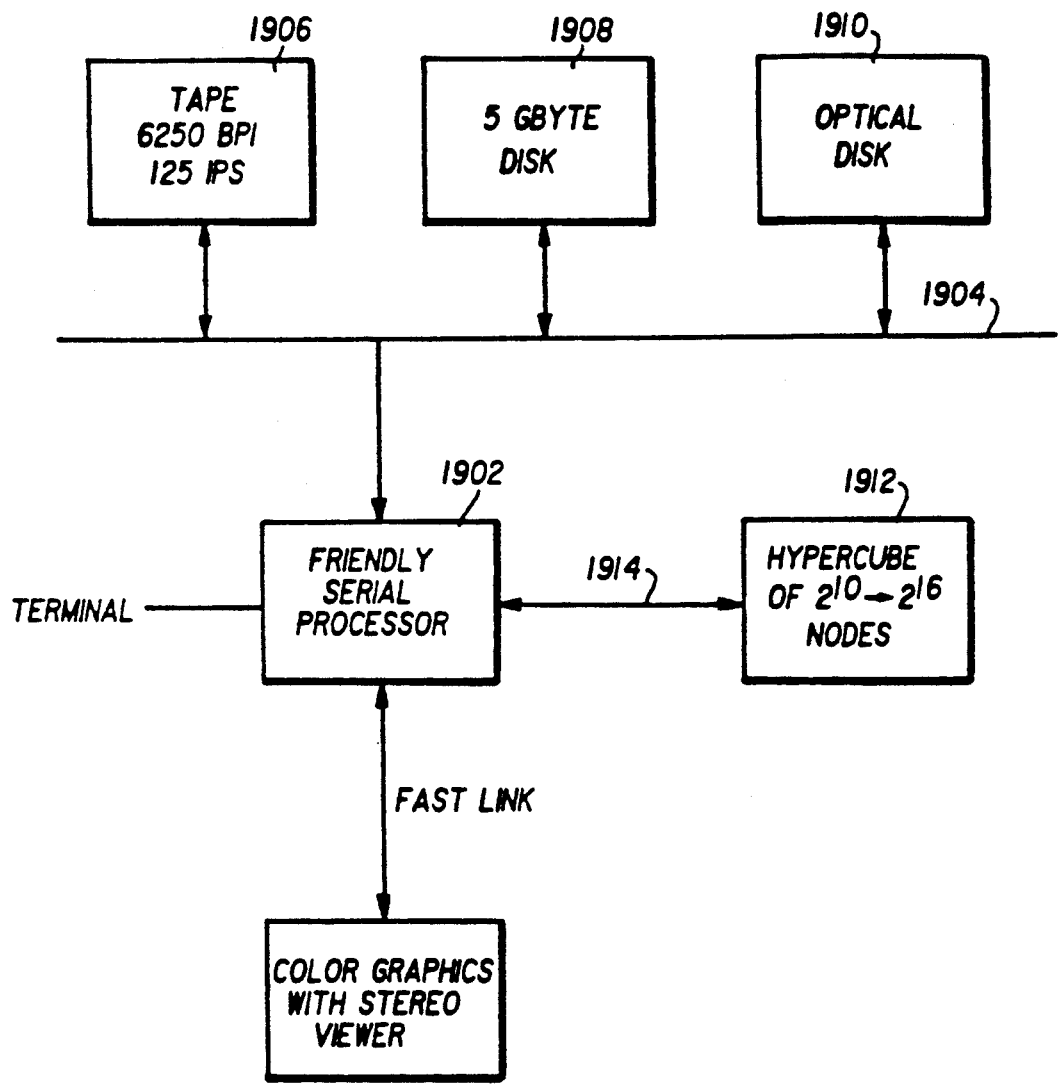
FIG. 19 shows a block diagram of the parallel processing mode of the present invention.

FIG. 19 shows in block diagram form the parallel processing approach that can be utilized in the present invention.

As shown in FIG. 19, a friendly serial processor 1902 is connected by a first bus 1904 to a plurality of data storage devices and input devices. Specifically, and only for purposes of illustration, a tape input stage 1906 is connected to bus 1904 so as to read into the system the parameters of the protein data base that is used. A high storage disk drive system 1908 (having, for example, 5 gigabits of storage) is also connected to bus 1904. Operationally, for even larger storage capabilities, an optical disk storage stage 1910 of conventional design can be connected to bus 1904.

The goal of the hypercube 1912 that is connected to the friendly serial, processor 1902 via a bidirectional bus 1914 is twofold: to perform searching faster, and to throw out candidates more automatically.

The hypercube 1912, having for example, $2^{10}$ to $2^{16}$ nodes provides for parallel processing. There are computers currently available which have up to 1,024 computing nodes. Thus each node would need to hold only about 1400 candidate linkers and local memory of available machines would be sufficient. This is the concept of the hypercube 1912. Using the hypercube parallel processing approach, the protein data base can be divided into as many parts as there are computing nodes. Each node is assigned to a particular known protein structure.

The geometry of the gap that has to be bridged by a linker is sent by the friendly serial processor 1902 via bus 1914 to the hypercube stage 1912. Each of the nodes in the hypercube 1912 then processes the geometrical parameters with respect to the particular candidate linker to which it is assigned. Thus, all of the candidates can be examined in a parallel fashion, as opposed to the serial fashion that is done in the present mode of the present invention. This results in much faster location (the inventors believe that the processing speed can be brought down from 6 hours to 3 minutes using conventional technology) in locating the candidates that can be evaluated by the second step 304 of the present invention.

Another advantage for the parallel processing embodiment is that it will provide sufficient speed to allow candidates to be thrown out more automatically. This would be achieved using molecular dynamics and energy minimization. While this could be done currently on serial processing computers (of the super computer variety such as those manufactured by Cray and Cyber) the parallel processing approach will perform the molecular dynamics and energy minimization much faster and cheaper than using the super computing approach.

In particular, hypercube computers exist which have inexpensive computing nodes which compare very favorably to supercomputers for scalar arithmetic. Molecular dynamics and energy minimization are only partly vectorizable because the potential functions used have numerous data-dependent branches.

VI. Preparation and Expression of Genetic Sequences, and Uses

The polypeptide sequences generated by the methods described herein, give rise by application of the genetic code, to genetic sequences coding therefor. Given the degeneracy of the code, however, there are in many instances multiple possible codons for any one amino acid. Therefore, codon usage rules, which are also well understood by those of skill in the art, can be utilized for the preparation of optimized genetic sequences for coding in any desired organism. (See, for example, Ikemura, *J. Molec. Biol.* 151:389–409 (1981)).

Generally, it is possible to utilize the cDNA sequences obtained from the light and heavy chains of the variable region of the original antibody as a starting point. These sequences can then be joined by means of genetic linkers coding for the peptide linker candidates elucidated by the methods of the invention. The genetic sequence can be entirely synthesized de novo or fragments of cDNA can be linked together with the synthetic linkers, as described.

A large source of hybridomas and their corresponding monoclonal antibodies are available for the preparation of sequences coding for the H and L chains of the variable region. As indicated previously, it is well known that most "variable" regions of antibodies of a given class are in fact quite constant in their three dimensional folding pattern, except for certain specific hypervariable loops. Thus, in order to choose and determine the specific binding specificity of the single chain binding protein of the invention it becomes necessary only to define the protein sequence (and thus the underlying genetic sequence) of the hypervariable region. The hypervariable region will vary from binding molecule to molecule, but the remaining domains of the variable region will remain constant for a given class of antibody.

Source mRNA can be obtained from a wide range of hybridomas. See for example the catalogue *ATCC Cell Lines and Hybridomas*, December 1984, American Type Culture Collection, 20309 Parklawn Drive, Rockville, Md. 20852, U.S.A., at pages 5–9. Hybridomas secreting monoclonal antibodies reactive with a wide variety of antigens are listed therein, are available from the collection, and usable in the invention. Of particular interest are hybridomas secreting antibodies which are reactive with viral antigens, tumor associated antigens, lymphocyte antigens, and the like. These cell lines and others of similar nature can be utilized to copy mRNA coding for the variable region or determine amino acid sequence from the monoclonal antibody itself. The specificity of the antibody to be engineered will be determined by the original selection process. The class of antibody can be determined by criteria known to those skilled in the art. If the class is one for which there is a three-dimensional structure, one needs only to replace the sequences of the hypervariable regions (or complementary determining regions). The replacement sequences will be derived from either the amino acid sequence or the nucleotide sequence of DNA copies of the mRNA.

It is to be specifically noted that it is not necessary to crystallize and determine the 3-D structure of each variable region prior to applying the method of the invention. As only the hypervariable loops change drastically from variable region to variable region (the remainder being constant in the 3-D structure of the variable region of antibodies of a given class), it is possible to generate many single chain 3-D structures from structures already known or to be determined for each class of antibody.

For example, linkers generated in the Examples in this application (e.g., TRY40, TRY61, TRY59, or TRY202', see below) are for $F_v$ regions of antibodies of the IgA class. They can be used universally for any antibody, having any desired specificity, especially if the antibody is of the IgA class.

Expression vehicles for production of the molecules of the invention include plasmids or other vectors. In general, such vectors containing replicon and control sequences which are derived from species compatible with a host cell are used in connection with the host. The vector ordinarily carries a replicon site, as well as specific genes which are capable of providing phenotypic selection in transformed cells. For example, *E. coli* is readily transformed using pBR322, a plasmid derived from an *E. coli* species. pBR322 contains genes for ampicillin and tetracycline resistance, and thus provides easy means for identifying transformed cells. The pBR322 plasmid or other microbial plasmids must also contain, or be modified to contain, promoters which can be used by the microbial organism for expression of its own proteins. Those promoters most commonly used in recombinant DNA construction include the beta lactamase, lactose promoter systems, lambda phage promoter's, and the tryptophan promoter systems. While these are the most commonly used, other microbial promoters have been discovered and can be utilized.

For example, a genetic construct for a single chain binding protein can be placed under the control of the leftward promoter of bacteriophage lambda. This promoter is one of the strongest known promoters which can be controlled. Control is exerted by the lambda repressor, and adjacent restriction sites are known.

The expression of the single chain antibody can also be placed under control of other regulatory sequences which may be homologous to the organism in its untransformed state. For example, lactose dependent *E. coli* chromosomal DNA comprises a lactose or lac operon which mediates lactose utilization by elaborating the enzyme beta-galactosidase. The lac control elements may be obtained from bacteriophage lambda plac5, which is infective for *E. coli*. The lac promoter-operator system can be induced by IPTG.

Other promoter/operator systems or portions thereof can be employed as well. For example, colicin E1, galactose, alkaline phosphatase, tryptophan, xylose, tac, and the like can be used.

Of particular interest is the use of the $O_L/P_R$ hybrid lambda promoter (see for example U.S. patent application Ser. No. 534,982 filed Sep. 3, 1983, and herein incorporated by reference).

Other preferred hosts are mammalian cells, grown in vitro in tissue culture, or in vivo in animals. Mammalian cells provide post translational modifications to immunoglobulin protein molecules including correct folding or glycosylation at correct sites.

Mammalian cells which may be useful as hosts include cells of fibroblast origin such as VERO or CHO-K1, or cells of lymphoid origin, such as the hybridoma SP2/O-AG14 or the myeloma P3x63Sg8, and their derivatives.

Several possible vector systems are available for the expression of cloned single chain binding proteins in mammalian cells. One class of vectors utilizes DNA elements which provide autonomously replicating extrachromosomal plasmids, derived from animal viruses such as bovine papilloma virus, polyoma virus, or SV40 virus. A second class of vectors relies upon the integration of the desired gene sequences into the host cell chromosome. Cells which have stably integrated the introduced DNA into their chromosomes can be selected by also introducing drug resistance genes such as *E. coli* GPT or Tn5neo. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H. (*Molec, Cell. Biol,* 3:280 (1983)), and others.

Another preferred host is yeast. Yeast provides substantial advantages in that it can also carry out post translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products, and secretes peptides bearing leader sequences (i.e., pre-peptides).

Any of a series of yeast gene expression systems incorporating promoter and termination elements from the actively expressed genes coding for glycolytic enzymes produce in large quantities when yeasts are grown in mediums rich in glucose can be utilized. Known glycolytic genes can also provide very efficient transcription control signals. For example, the promoter and terminator signals of the phosphoglycerate kinase gene can be utilized.

Once the strain carrying the single chain binding molecule gene has been constructed, the same can also be subjected to mutagenesis techniques using, chemical agents or radiation, as is well known in the art. From the colonies thus obtained, it is possible to search for those producing binding molecules with increased binding affinity. In fact, if the first linker designed with the aid of the computer fails to produce an active molecule, the host strain containing the same can be mutagenized. Mutant molecules capable of binding antigen can then be screened by means of a routine assay.

The expressed and refolded single chain binding proteins of the invention can be labelled with detectable labels such as radioactive atoms, enzymes, biotin/avidin labels, chromophores, chemiluminescent labels, and the like for carrying out standard immunodiagnostic procedures. These procedures include competitive and immunometric (or sandwich) assays. These assays can be utilized for the detection of antigens in diagnostic samples. In competitive and/or sandwich assays, the binding proteins of the invention can also be immobilized on such insoluble solid phases as beads, test tubes, or other polymeric materials.

For imaging procedures, the binding molecules of the invention can be labelled with opacitying agents, such as NMR contrasting agents or X-ray contrasting agents. Methods of binding, labelling or imaging agents to proteins as well as binding the proteins to insoluble solid phases are well known in the art. The refolded protein can also be uses for therapy when labelled or coupled to enzymes or toxins, and for purification of products, especially those produced by the biotechnology industry. The proteins can also be used in biosensors.

Having now generally described this invention the same will be better understood by reference to certain specific examples which are included for purposes of illustration and are not intended to be limited unless otherwise specified.

EXAMPLES

In these experiments, the basic $F_v$ 3-D structure used for the computer assisted design was that of the anti-phosphoryl choline myeloma antibody of the IgA class, MCPC-603. The X-ray structure of this antibody is publicly available from the Brookhaven data base.

The starting material for these examples was monoclonal antibody cell line 3C2 which produced a mouse anti-bovine growth hormone (BGH). This antibody is an IgG1 with a gamma 1 heavy chain and kappa light chain. cDNA's for the heavy and light chain sequences were cloned and the DNA sequence determined. The nucleotide sequences and the translation of these sequences for the mature heavy and mature light chains are shown in FIGS. 21 and 22 respectively.

Plasmids which contain just the variable region of the heavy and light chain sequences were prepared. A ClaI site and an ATG initiation codon (ATCGATG) were introduced before the first codon of the mature sequences by site directed mutagenesis. A HindIII site and termination codon (TAAGCTT) were introduced after the codon 123 of the heavy chain and the codon 109 of the light chain. The plasmid containing the $V_H$ sequences is pGX3772 and that containing the $V_L$ is pGX3773 (FIG. 23).

The examples below were constructed and produced by methods known to those skilled in the art.

EXAMPLE 1

Preparation of a Single Chain Binding Molecule

A. Computer Design

A two-linker example (referred to as TRY40) was designed by the following steps.

First, it was observed that light chains were much easier to make in *E. coli* than were heavy chains. It was thus decided to start with light chain. (In the future, one could certainly make examples which begin with heavy chain because there is a very similar contact between a turn in the heavy chain and the exit strand of the light chain.)

Figure 30A:
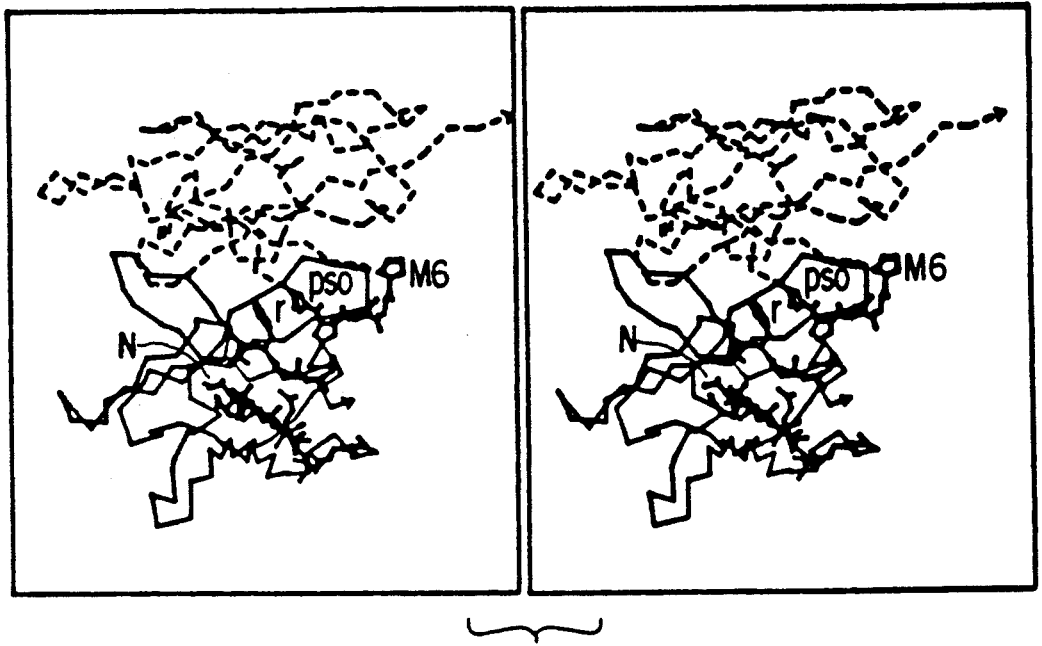

Refer to stereo FIG. 30A which shows the light and heavy domains of the $F_v$ from MCPC-603 antibody; the constant domains are discarded. A line joining the alpha carbons of the light chain is above and dashed. The amino terminus of the light chain is to the back and at about 10 o'clock from the picture center and is labeled "N." At the right edge of the picture, at about 2 o'clock is an arrow showing the path toward the constant domain. Below the light chain is a line joining the alpha carbons of the heavy chain. The amino terminus of the heavy chain is toward the viewer at about 7 o'clock and is also labeled "N." At about 4:30, one sees an arrow showing the heavy chain path to its constant domain.

The antigen-binding site is to the left, about 9 o'clock and between the two loops which project to the right above (light chain) and below (heavy chain).

In addition to the alpha carbon traces, there are three segments in which all non-hydrogen atoms have been drawn. These strands are roughly parallel and from upper right to lower left. They are (a) Proline 46 to Proline 50 of the light chain.
(b) Valine I11 to Glycine 113 of the heavy chain.
(c) Glutamic acid 1 to glycine 10 of the heavy chain.

Figure 30B:

The contact between tryptophan 112 of the heavy chain and proline 50 of the light chain seems very favorable. Thus it was decided that these two residues should be conserved. Several linkers were sought and found which would join a residue at or following Tryptophan 112 (heavy) to a residue at or following Proline 50 (light). Stereo FIG. 30B shows the region around TRP 112H in more detail. The letter "r" stands between the side-chain of TRP 112H and PRO 50L; it was wished to conserve this contact. The letter "q" labels the carboxy terminal strand which leads towards the constant domain. It is from this strand that a linker will be found which will connect to PRO 50L.

Once a linker is selected to connect 112H to 50L, one needs a linker to get from the first segment of the light chain into the beginning portion of the heavy chain. Note that PRO 46L turns the chain toward PRO 50L. This turning seemed very useful, so it was decided to keep PRO 46L. Thus the second linker had to begin after 46L and before 50L, in the stretch marked "s." A search for linkers was done beginning on any of the residues 46L, 47L, or 48L. Linkers beginning on residue 49L were not considered because the chain has already turned toward 50L and away from the amino terminal of the heavy chain. Linkers were sought which ended on any of the residues 1H to 10H.

Figure 30C:
Figure 30D:
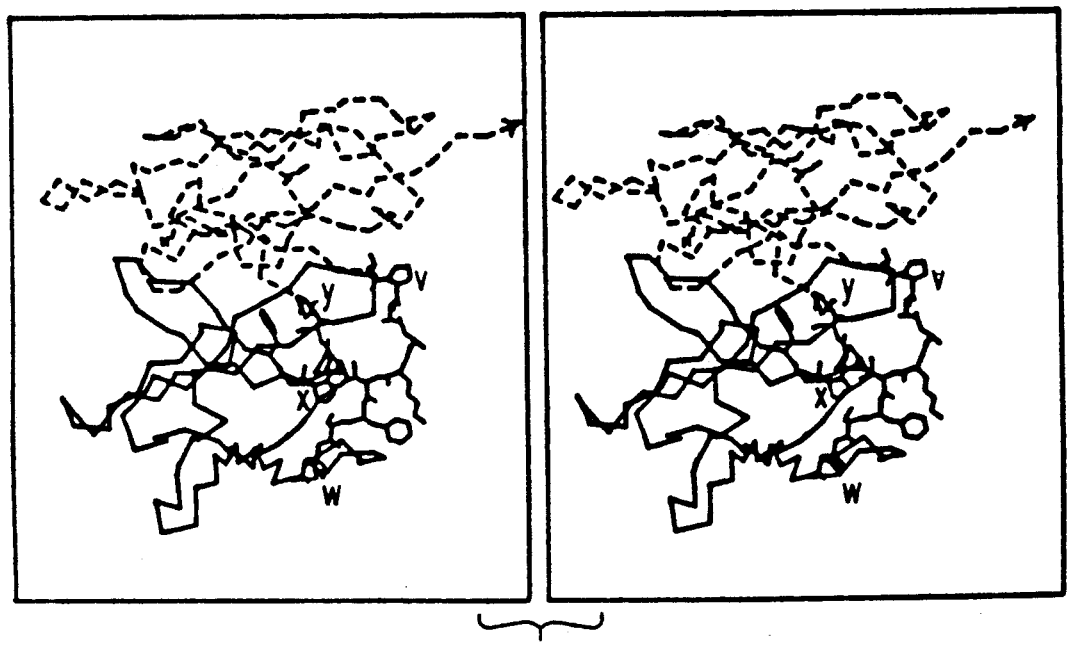

FIG. 30C shows the linked structure in detail. After TRP 112H and GLY 113H, was introduced the sequence PRO-GLY-SER, and then comes PRO 50L. A computer program was used to look for short contacts between atoms in the linker and atoms in the retained part of the $F_v$. There is one short contact between the beta carbon of the SER and PRO 50L, but small movements would relieve that. This first linker runs from the point labeled "x" to the point labeled "y." The second linker runs from "v" to "w." Note that most of the hydrophobic residues (ILE and VAL) are inside. There is a PHE on the outside. In addition, the two lysine residues and the asparagine residue are exposed to solvent as they ought to be. FIG. 30D shows the overall molecule linked into a single chain.

B. Genetic Constructs

These constructs were prepared and the plasmids containing them using *E. coli* hosts. Once constructed, the sequences can be inserted into whichever expression vehicle used in the organism of choice. The first construction was TRY40 (the two-linker construction) which produces a protein with the following sequence: Met-[L-chain 1-41]-Ile-Ala-Lys-Ala-Phe-Lys-Asn-[H-chain 8-105]-Pro-Gly-Ser-[L-chain 45-109]. The nucleotide sequence and its translation are seen in FIG. 24. The hypervariable regions in TRY40 (as in TRY61, 59, and 104B, see below) correspond, as indicated, to an IgG1 anti BGH antibody, even though the 3-D analysis was done on the $F_v$ region of MCPC-603 antibody, having a different specificity (anti-phosphoryl choline) but having a similar framework in the variable region.

The antibody sequences in the plasmids pGX3772 and pGX3773 were joined to give the sequence of TRY40 in the following manner. The plasmids used contained an M13 bacteriophage origin of DNA replication. When hosts containing these plasmids are superinfected with bacteriophage M13 two types of progeny are produced, one containing the single-strand genome and the other containing a specific circular single-strand of the plasmid DNA. This DNA provided template for the oligonucleotide directed site specific mutagenesis experiments that follow. Template DNA was prepared from the two plasmids. An EcoRI site was introduced before codon 8 of the $V_H$ sequence in pGX3772, by site directed mutagenesis, producing pGX3772'. Template from this construction was prepared and an XbaI site was introduced after codon 105 of the $V_H$ sequence producing pGX3772".

An EcoRI and an XbaI site were introduced into pGX3773 between codons 41 and 45 of the $V_L$ sequence by site directed mutagenesis producing pGX3773'.

To begin the assembly of the linker sequences plasmid pGX3773' ($V_L$) DNA was cleaved with EcoRI and XbaI and treated with calf alkaline phosphatase. This DNA was ligated to the EcoRI to XbaI fragment purified from plasmid pGX3772" ($V_H$) which had been cleaved with the two restriction enzymes. The resulting plasmid pGX3774, contained the light and heavy chain sequences in the correct order linked by the EcoRI and XbaI restriction sites. To insert the correct linker sequences in frame, pGX3774 template DNA was prepared. The EcoRI junction was removed and the linker coding for the -Ile-Ala-Lys-Ala-Phe-Lys-Asn- inserted by site-directed mutagenesis, producing plasmid pGX3774'. Template DNA was prepared from this construction and the XbaI site corrected and the linker coding for -Pro-Gly-Ser inserted by site directed mutagenesis producing plasmid pGX3775. The sequence was found to be correct as listed in FIG. 24 by DNA sequencing.

In order to express the single-chain polypeptide, the sequence as a ClaI to HindIII fragment was inserted into a vector pGX3703. This placed the sequence under the control of the $O_L/P_R$ hybrid lambda promoter (U.S. patent application Ser. No. 534,982, Sep. 23, 1983). The expression plasmid is pGX3776 (FIG. 25). The plasmid pGX3776 was transformed into a host containing a heat sensitive lambda phage repressor; when grown at 30° C. the synthesis of the TRY40 protein is repressed. Synthesis was induced by raising the temperature to 42° C., and incubating for 8–16 hours. The protein was produced at 7.2% of total cell protein, as estimated on polyacrylamide gel electropherograms stained with Coomassie blue.

EXAMPLE 2

Preparation of a Single Chain Binding Molecule

A. Computer Design

A one-linker example (referred to as TRY61) was designed by the following steps.

Refer to stereo FIG. 31A which shows the light and heavy domains of the $F_v$; the constant domains are discarded. A line joining the alpha carbons of the light chain is dashed. The amino terminus of the light chain is to the back and at about the center of the picture and is labeled "N". At the right edge of the picture, at about 2 o'clock is an arrow showing the path toward the constant domain of the light chain. Below the light chain is a line joining the alpha carbons of the heavy chain. The amino terminus of the heavy chain is toward the viewer at about 9 o'clock and is also labeled "N". At about 4:30, one sees an arrow showing the heavy chain path to its constant domain.

In addition to the alpha carbon traces, there are two segments in which all non-hydrogen atoms have been drawn. These segments are the last few residues in the light chain and the first ten in the heavy chain. Linkers were sought between all pairs of these residues, but only a few were found because these regions are widely separated.

FIG. 31B shows the linker in place. Note that the molecule now proceeds from the amino terminal of the light chain to the carboxy terminal strand of the heavy chain. Note also that the antigen-binding region is to the left, on the other side of the molecule from the linker.

B. Genetic Constructs

The sequence of TRY61 (a single-linker embodiment) is Met-[L-chain 1-104]-Val-Arg-Gly-Ser-Pro-Ala-Ile-Asn-Val-Ala-Val-His-Val-Phe-[H-chain 7-123]. The nucleotide sequence and its translation are shown in FIG. 26.

To construct TRY61, plasmid pGX3772' DNA was cleaved with ClaI and EcoRI and treated with calf alkaline phosphatase. This DNA was ligated with the ClaI to HindIII fragment from pGX3773 and two oligonucleotides which code for the linker sequence and have HindIII and EcoRI ends, so that the linker can only be ligated in the correct orientation. The resulting plasmid, pGX3777, was used to prepare template DNA. This DNA was used for site directed mutagenesis to remove the HindIII site inside the antibody sequences. The correct construction, pGX3777', was used to make template DNA for a site directed mutagenesis to remove the EcoRI site. The ClaI to HindIII fragment from the final construction, pGX3778, containing the TRY61 coding sequence was confirmed by DNA sequencing. The ClaI to HindIII was inserted into the pGX3703 expression vector. This plasmid is called pGX4904 (FIG. 27). This plasmid was transformed into an E. coli host. The strain containing this plasmid has been induced, and the single chain protein produced as >2% of total cell protein.

EXAMPLE 3

Preparation of a Single Chain Binding Molecule

A. Computer Design

A one-linker example (referred to as TRY59) was designed by the following steps.

Refer to stereo FIG. 32A which shows the light and heavy domains of the $F_V$; the constant domains are discarded. A line joining the alpha carbons of the light chain is above and dashed. The amino terminus of the light chain is to the back and at about 10 o'clock from the center of the picture and is labeled "N". At the right edge of the picture, at about 2 o'clock is an arrow showing the path toward the constant domain of the light chain. Below the light chain is a line joining the alpha carbons of the heavy chain. The amino terminus of the heavy chain is toward the viewer at about 8 o'clock and is also labeled "N". At about 4:30, one sees an arrow showing the heavy chain path to its constant domain.

In addition to the alpha carbon traces, there are two segments in which all non-hydrogen atoms have been drawn. These segments are the last few residues in the light chain and the first ten in the heavy chain. Linkers we sought between all pairs of these residues, but only a few were found because these regions are widely separated.

FIG. 32B shows the linker in place. Note that the molecule now proceeds from the amino terminal of the light chain to the carboxy terminal strand of the heavy chain. Note also that the antigen-binding region is to the left, on the other side of the molecule from the linker.

The choice of end points in TRY59 is very similar to TRY61. Linkers of this length are rare. The tension between wanting short linkers that fit very well and which could be found for the two-linker case (TRY40) and the desire to have only one linker, (which is more likely to fold correctly) is evident in the acceptance of TRY59. The linker runs from the point marked "A" in FIG. 32B to the point marked "J." After five residues, the linker becomes helical. At the point marked "x," however, the side-chain of an ILE residue collides with part of the light chain. Accordingly, that residue was converted to GLY in the actual construction.

B. Genetic Constructs

The sequence of TRY59 (the single linker construction) is Met-[L-chain 1-105]-Lys-Glu-Ser-Gly-Ser-Val-Ser-Ser-Glu-Gln-Leu-Ala-Gln-Phe-Arg-Ser-Leu-Asp-[H-chain 2-123]. The nucleotide sequence coding for this amino acid sequence and its translation is shown in FIG. 28. The BglI to HindIII fragment (read clockwise) from plasmid pGX3773 containing the $V_L$ sequence and the ClaI to BglI fragment (clockwise) from pGX3772 has been ligated with two oligonucleotides which form a fragment containing the linker sequence for TRY59 and have ClaI and HindIII ends. The ClaI and &&III junctions within this plasmid are corrected by two successive site directed mutageneses to yield the correct construction. The ClaI to HindIII fragment from this plasmid is inserted into the $O_L/P_R$ expression vector as in Examples 1 and 2. The resulting plasmid, pGX4908 (FIG. 29) is transformed into an E. coli host. This strain is induced to produce the protein coded by the sequence in FIG. 28 (TRY59).

EXAMPLE 4

Preparation of a Single Chain Binding Molecule

A. Computer Design

In this design an alternative method of choosing a linker to connect the light and heavy variable regions was used. A helical segment from human hemoglobin was chosen to span the major distance between the carboxy terminus of the variable light chain and the amino terminus of the variable heavy chain. This alpha helix from human hemoglobin was positioned at the rear of the $F_v$ model using the computer graphics system. Care was taken to position the helix with its ends near the respective amino and carboxyl termini of the heavy and light chains. Care was also taken to place hydrophobic side chains in toward the $F_v$ and hydrophilic side chains toward the solvent. The connections between the ends of the variable regions and the hemoglobin helix were selected by the previously described computer method (EXAMPLE 1-3).

B. Genetic Constructs

The sequence of TRY104b (a single linker construction) is Met-[L-chain 1-106]-Ala-Glu-Gly-Thr-[(Hemoglobin helix"Leu-Ser-Pro-Ala-Asp-Lys-Thr-Asn-Val-Lys-Ala-Ala-Trp-Gly-Lys-Val-]Met-Thr-[H-chain 3—123]. The nucleotide sequence coding for this amino acid sequence and its translation is shown in FIG. 33. The BglI to HindIII fragment (read clockwise) from plasmid pGX3773 containing the $V_L$ sequence and the CLAI to BglI fragment (clockwise) from pGX3772 has been ligated with two oligonucleotides which form a fragment containing the linker sequence for TRY104b and have ClaI and HindIII ends. The ClaI and HindIII Junctions within this plasmid are corrected by two successive site directed mutageneses to yield the correct construction. The ClaI to HindIII fragment from this plasmid is inserted into the OL/PR expression vector as in Examples 1–3. The resulting plasmid, pGX4910 (FIG. 34) is transformed into an *E. coli* host. This strain is induced to produce the protein coded by the sequence in FIG. 33 (TRY104b).

EXAMPLE 5

Purification of the Proteins

The single-chain antigen binding proteins from TRY40, TRY61, TRY59 and TRY104b are insoluble, and cells induced to produce these proteins show refractile bodies called inclusions upon microscopic examination. Induced cells were collected by centrifugation. The wet pellet was frozen on dry ice, then stored at −20° C. The frozen pellet was suspended in a buffer and washed in the same buffer, and subsequently the cells were suspended in the same buffer. The cells were broken by passage through a French pressure cell, and the inclusion bodies containing the single-chain antigen were purified by repeated centrifugation and washing. The pellet was solubilized in guanidine-HCl and reduced with 2-mercaptoethanol. The solubilized material was passed through a gel filtration column, i.e., Sephacryl TM S-300. Other methods such as ion exchange chromatography could be used.

EXAMPLE 6

Folding of the Proteins

Purified material was dialyzed against water, and the precipitate protein collected by centrifugation. The protein was solubilized in urea and reduced with 2-mercaptoethanol. This denatured and solubilized material was dialyzed against a buffer containing salt and reducing agents to establish the redox potential to form the intra domain (one each for the light and heavy chain variable region sequences) disulfide bridges (Saxena and Wetlanfer, *Biochem.* 9:5015–5023 (1970)). The folded protein was assayed for BGH binding activity.

EXAMPLE 7

Binding Assay

BGH was immobilized on nitrocellulose strips along with non-specific proteins such as bovine serum albumin or lysozymes. Further non-specific protein binding was blocked with an immunologically inert protein, for example gelatin. Folded Single Chain Antibody (SCA TM) antigen binding protein (herein referred to as "SCA TM protein") was tested for its ability to bind to BGH. The SCA TM protein was detected by a rabbit anti-L chain (of the monoclonal) anti-serum. The rabbit antibodies were reacted with goat anti-rabbit IgG coupled to peroxidase. The strips were reacted with chemicals which react with the peroxidase to give a color reaction if the peroxidase is present.

FIG. 35 shows the result of this spot assay for TRY61 (strip 1) and TRY40 (strip 2). Strip 3 was stained with amido black to show the presence of all three proteins. The other proteins, TRY59, TRY104b gave similar results in the spot assay. A competition assay with the SCA TM protein competing with the monoclonal can be used as well. The results of competing $F_{ab}$ of 3C2 monoclonal with 1 and 10 µg of TRY59 protein which had been affinity purified are shown in FIG. 36. The affinity estimated from the Ic50 of this experiment was approximately $10^6$. The data are summarized in Table 1.

TABLE 1

PROPERTIES OF THE PROTEINS PRODUCED BY THE SINGLE-CHAIN CONSTRUCTIONS

| Single Chain | Number of Linkers | Spot Test | Binding to BGH Column | Ka |
|---|---|---|---|---|
| TRY40 | 2 | + | − | ND |
| TRY59 | 1 | + | + | $10^6$ |
| TRY61 | 1 | + | − | ND |
| TRY104B | 1 | + | + | ND |
| 3C2 MONOCLONAL | NA | + | + | $10^6$–$10^8$ |

ND = Not Determined
NA = Not Applicable

This Example demonstrates that the single chain binding proteins of the present invention are as effective as monoclonal antibodies in binding specific molecules. Thus, the single chain binding molecules of the invention can be employed in the same manner as antibodies (either polyclonal or monoclonal) or antibody fragments to assay for the presence and/or concentration of a ligand molecule.

EXAMPLE 8

Binding Activity of Anti-Bovine Growth Hormone Single-Chain Antigen-Binding Proteins When the 3C2/TRY59 gene is expressed in *E. coli*, the single-chain protein accumulates in insoluble inclusion bodies. The 3C2/TRY59 protein from these inclusion bodies had an apparent molecular weight of 26,000 daltons as determined by SDS polyacrylamide gel electrophoresis. This compares favorably with the molecular weight of 26,652 daltons calculated from the amino acid sequence.

The 3C2/TRY59 expressing *E. coli* cells were lysed by resuspending the *E. coli* cell paste at a 10-fold weight to volume ratio in 50 mM Tris (pH 8.2), 5 mM ethylene diamine tetraacetate (EDTA), 0.04 mM PMSF, and 0.1% β-mercaptoethanol (BME) and disrupting by two passes through a French Pressure Cell at 1,600 psi. Fresh PMSF was added after the first pass. The cell debris was further disrupted by sonication. The cellular extract was incubated with lysozyme (100 µg/ml and DNase I (10 µg/ml) for one hour at room temperature. The crude inclusion body pellet was recovered by centrifugation at 750×g for one hour, washed twice with the starting buffer, and solubilized in 50 mM glycine, pH 10.8, 9M urea, 1 mM EDTA and 20 mM BME (Boss, M. A. et al., *Nucl. Acid Res.* 12:3791 (1984)).

The solubilized inclusion bodies were cleared by centrifugation at 12,000×g for 10 minutes and then diluted to a final protein concentration of 100 µg/ml in the solubilizing buffer. The diluted inclusion bodies-were dialyzed against three changes of 10 volumes of 50 mM glycine pH 10.8, 100 mM KCl, 5.0% glycerol, 0.05 mM EDTA, 1 mM reduced glutathionine, and 0.2 mM oxidized glutathione (Saxena, V. P. et al., *Biochem.* 9:5015 (1970)). The renatured protein was finally dialyzed against 10 volumes of phosphate buffered saline (PBS).

The solubilized, renatured, anti-BGH 3C2/59 protein was purified by affinity chromatography on BGH-Sepharose with elution using 3M sodium thiocyanate at neutral pH. The affinity-purified protein migrates as a single band of 26,000 daltons when analyzed by SDS polyacrylamide gel electrophoresis under both reduced and non-reduced conditions. The amount of protein which was successfully folded and therefore able to bind to a BGH-Sepharose column varied between 5-30% in different experiments. To demonstrate that the affinity-purified protein retained binding activity following thiocyanate elution, it was loaded onto a second BGH-Sepharose column. As is shown in FIG. 37, greater than 90% of the single-chain protein bound to BGH-Sepharose and was eluted with thiocyanate, indicating that the affinity-purified protein retained antigen-binding activity. In a parallel experiment, single-chain protein produced from a modified 3C2/59 gene in which the sequence of five of the six hypervariable regions had been changed did not bind to BGH-Sepharose, demonstrating that binding occurs at the antigen-binding site.

The 3C2/TRY59 protein was found to be able to cross-react with antiserum prepared against purified 3C2 light chain on Western blots, thus indicating that the single chain binding molecule had biologic binding activity.

The relative affinity of the purified 3C2/59 protein for BGH was determined by competition with $F_{ab}$ fragments isolated from the 3C2 monoclonal antibody. Increasing amounts of unlabeled $F_{ab}$ fragments were mixed with ($^{35}$S)-methionine labeled 3C2/59 protein and the mixture was incubated with BGH-Sepharose. After incubation, the amount of bound radiolabeled protein was determined. A competition curve is shown in FIG. 38. The concentration of $F_{ab}$ which inhibited binding of the radiolabeled protein by 50% was one-half the concentration of the radiolabeled protein, indicating that the $K_a$ of the 3C2/59 single-chain protein was within a factor of four of the $K_a$ of the $F_{ab}$. This result indicates that the binding activity of the single chain binding molecules of the present invention is equivalent to that of antibodies.

EXAMPLE 9

Preparation of a Single Chain Binding Molecule

A. Computer Design

A peptide which fits into a groove on the backside of the variable domain structure was prepared and employed as a linker of $V_H$ and $V_L$ chains. This linker is composed primarily of alternating glycine and serine residues, and contains glutamic acid and lysine residues inserted to enhance solubility. Amino acids at the carboxyl terminus of the $V_L$ sequence and at the amino terminus of the $V_H$ sequence were again chosen as starting and ending points. Using computer graphics to visualize the structure, linker amino acids were added one at a time until the $V_L$ chain was linked to the $V_H$ chain. The linkers in the anti-fluorescein 18-2-3-/TRY202' and 4-4-20/TRY202' single-chain proteins are examples of this second type. This linker was designed by the method described in co-pending U.S. patent application Ser. No. 092,147, which application is herein incorporated by reference in its entirety.

B. Genetic Constructions

Single-chain antigen-binding protein genes were constructed using the sequences of the variable domains of two different anti-fluorescein monoclonal antibodies: 18-2-3, an IgM (Ballard, D. W., et al., *Proc. Natl. Acad. Sci. USA* 80:5071 (1983)), and 4-4-20, an IgG2a (Kranz, D. M., et al., *Mol. Immunol.* 18:889 (1981)). The anti-fluorescein monoclonal antibodies were chosen for continued development of the single-chain antigen-binding protein technology because this antibody-antigen system has been well-characterized (Reviewed In: *Fluorescein Hapten: an Immunological Probe*, E. W. Voss, Jr. , ed. , CRC Press, Inc. , Boca Raton, (1984)). Several anti-fluorescein monoclonal antibodies with high affinity for fluorescein have been isolated and a quantitative assay for binding based on the quenching of fluorescein has been described (Herron, J. N., In: *Fluorescein Hapten: an Immunological Probe*, E. W. Voss, ed., CRC Press, Boca Raton, pp. 49-76 (1984)).

The $V_L$ and $V_H$ cDNA sequences were synthesized by priming on RNA isolated from hybridoma cells with oligonucleotides complementary to the first constant region of each chain. To verify that the isolated cDNA clones encoded the $V_L$ and $V_H$ chains, the amino acid sequences translated from the nucleotide sequences were compared to the N-terminal amino acid sequences of the parent antibodies. The sequences for 18-2-3/TRY202', 18-2-3/TRY59 and 4-4-20/202' are shown in FIGS. 39, 40, and 41 respectively.

The anti-fluorescein single-chain antigen-binding proteins were produced, solubilized, and renatured as described above for the anti-BGH 3C2/TRY59 protein. After renaturation, active 18-2-3/TRY59 protein was purified on a fluorescein Sepharose affinity column. To assay binding activity, fluorescence in the presence of a constant amount of 18-2-3/TRY59 protein and 18-2-3 monoclonal antibody was determined over ligand concentrations ranging from $10^{-12}$ to $10^{-7}$M. The fraction of fluorescein fluorescence quenched when fluorescein-binding proteins are added is a quantitative measure of the fluorescein bound by the protein. These measurements have been used to estimate the relative affinity constants for the 18-2-3/TRY59 protein and the 18-2-3 monoclonal antibody. All protein added was assumed to be active; therefore, the calculations give an underestimate of the true binding affinity. The 18-2-3/59 single-chain-protein bound fluorescein equally well as the 18-2-3 monoclonal antibody per mole of binding site indicating that the affinities are identical. The 18-2-3/202' protein was estimated to have an affinity of 0.6×that of the 18-2-3 monoclonal antibody.

The affinity constant ($K_a$) of the anti-fluorescein 4-4-20/TRY202' protein was determined after renaturation and purification of the protein by affinity chromatography on fluorescein Sepharose. The $K_a$ for the 4-4-20/TRY202' protein is $1.1 \times 10^9$ liters/mole compared to $8 \times 10^9$ liters/mole for the $F_{ab}$ derived from the 4-4-20 monoclonal antibody. These affinity constants were determined from detailed fluorescence quenching assays and Scatchard Analysis of the data.

Watt, R. M. et al. (*Immunochemistry* 14:533 (1977)) have noted that the absorbance spectrum of fluorescein was shifted from a maximum at 493 nm to a maximum around 505 nm when the fluorescein was bound by an anti-fluorescein antibody. To test whether this shift occurred with fluorescein bound to a single-chain antigen-binding protein, the absorption spectra of the 4-4-20/TRY202′ protein was measured as fluorescence emitted as a function of excitation wavelength. The results are presented in FIG. 42. Emission spectra were measured over excitation wavelengths of 470–515 nm. The curve on the left is always the emission of free fluorescein and the curve on the right, bound fluorescein. (A, 4-4-20 monoclonal antibody; B, 4-4-20 $F_{ab}$; C, 4-4-20/202′ protein). The 4-4-20/TRY202′ protein causes a similar shift in excitation maximum from 493 nm to 505 as the monoclonal anti-body and $F_{ab}$, demonstrating that fluorescein is bound by the 4-4-20/202′ protein in the same way as it is bound by the monoclonal antibody.

These results demonstrate that the methods of the present invention are capable of identifying the structure of single chain binding molecules which can be produced, and solubilized, and which are capable of exhibiting biological binding activity which is equivalent in specificity and affinity to that of monoclonal antibodies.

EXAMPLE 10

Purification of 4-4-20/202′ and its Activity 4-4-20/202′ protein renatured by the method described in Example 8 was purified by repeated chromatography on a Water's Protein PAK SP 5PW cation exchange HPLC column using salt and pH gradients for elution. Fluorescein binding fractions were pooled and a detailed analysis of fluorescein binding performed. The results are given in the Scatchard plot shown in FIG. 43. The binding affinity is $4 \times 10^8$ l/mole. This is slightly lower than previously found probably due to the presence of calcium ion in the sample. Eighty-eight percent of the SCA TM protein is active.

In place of the dialysis step, additional renaturations have been performed by solubilizing the inclusion bodies in guanidine-HCl in the presence of mercaptoethanol followed by a dilution of 100 to 10,000 fold into renaturation buffer. The solubilization buffer contains 6M guanidine-HCl, 50 mM Tris pH 8.0, 100 mM KCl, 10 mm $CaCl_2$, 5% glycerol, 1 mM glutathione (reduced), and 0.1 mM glutathione (oxidized). Additional larger scale purifications have been performed on a Poly LC Poly CAT A HPLC column with good success.

EXAMPLE 11

Blood Clearance and Biodistribution

Purified 4-4-20/202′ SCA TM protein was labeled with $^{125}I$ using a published method (EP 0 203 764 A2). Radiolabeled SCA TM protein was injected into BALB/C mice. Groups of four mice were sacrificed at 15 min., 30 min., 1 hr., 2 hr., and 4 hr. and the radioactivity in organs and blood determined to measure the blood clearance rate and the biodistribution. The blood clearance is shown in FIG. 44. The radiolabeled SCA TM protein cleared from the blood rapidly and distributed to all organs well.

EXAMPLE 12

Synthesis of SCA TM Protein in *Bacillus subtilis*

Plasmids were constructed for testing the expression and secretion of the 4-4-20/202′ SCA TM protein in *Bacillus subtilis*. Three promoters and signal sequences were used: amy, the promoter and signal for amylase; npr, the promoter and signal for the neutral protease; and apr, the promoter and signal for the alkaline protease. These promoters and signal sequences are each contained on an EcoRI to BamH1 restriction fragment. The three fragments are interchangeable in a Genex Bacillus expression vector so that each can be tested with new genes. For example, pGX5263, containing the amy promoter/signal sequence coupled to the 4-4-20/202′ gene is shown in FIG. 45. The apr and npr promoter/signal sequence constructions are identical except they contain the corresponding EcoRI to BamH1 restriction fragment for apr and npr. The host strain for expression from these plasmids is GX8008 (International Patent Application WO 87/05025) an aor or derivative of *Bacillus subtilis* IS53 (International Patent Application WO 86/01824)). A table of the strains and the plasmids they contain is shown below.

TABLE 2

BACILLUS SUBTILIS STRAINS AND PLASMID CONSTRUCTIONS

| Strain | Plasmid | Promoter/gene |
| --- | --- | --- |
| GX8835 | pGX5257 | Apr/4-4-20/202′ |
| GX8836 | pGX5258 | Npr/4-4-20/202′ |
| GX8841 | pGX5263 | Amy/4-4-20/202′ |

The signal sequences coupled to the genes are shown in FIG. 46. In FIG. 46, the term "SCA" refers to SCA TM protein. There are extra amino acids between the end of the signals and the beginning of the 4-4-20/202′, starting with the asterisk and ending just before the methionine of the 4-4-20/202′ gene. Therefore any processed product of these genes may be slightly larger than the SCA TM protein produced in *E. coli*.

All of the constructions produced SCA TM protein which was processed and appeared in the culture medium. A gel and Western blot analysis of the protein produced by strain GX8841 was performed. The lane containing the cell supernatant or culture medium showed a band, stainable by an SCA TM protein specific reaction, which was slightly larger than the SCA TM protein purified from *E. coli*. The lane containing the total cell protein showed the processed band and a band slightly larger which was unprocessed SCA TM protein. In addition there was a band of about 45,000 daltons which was nonspecifically stained by our SCA TM protein staining method. It should be noted that this band does not appear in the culture medium, thus supporting the argument that the SCA TM protein which appears in the culture medium is the result of secretion and not partial cell lysis.

SCA TM protein produced by strain GX8841 was recovered from the culture medium by concentration using tangential flow filtration, batch chromatography on DE-52, further concentration by batch on DE-53 cation exchange chromatography, and purification on the Water's Protein PAK SP 5PW HPLC column. A ten liter fermentation produces approximately 10 mg of active protein in the culture medium. A Scatchard analysis of fluorescein binding by this protein is shown in FIG. 47. This Scatchard analysis shows the binding affinity to be $1 \times 10^9$ l/mole with an activity of 50%. Production of active SCA TM protein in *Bacillus subtilis* provides an alternative production system for SCA TM proteins.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

We claim:

1. A single chain polypeptide having binding affinity for a given antigen, said polypeptide comprising:
   (a) a first polypeptide comprising the antigen binding portion of the light chain variable region of an antibody;
   (b) a second polypeptide comprising the antigen binding portion of the heavy chain variable region of an antibody; and
   (c) at least one peptide liner linking said first and second polypeptides (a) and (b) into a single chain polypeptide having binding affinity for said given antigen.

2. The polypeptide of claim 1 wherein said peptide liner (c) is not derived from an antibody.

3. The polypeptide of claim 1 which comprises one peptide liner linking said first and second polypeptides (a) and (b) into said single chain.

4. The polypeptide of claim 3 which comprises in sequence:
   (i) an N-terminal polypeptide from the antigen binding portion of the light chain variable region of an antibody;
   (ii) a peptide linker; and
   (iii) a C-terminal polypeptide from the antigen binding portion of the heavy chain variable region of an antibody.

5. The polypeptide of claim 3 which comprises, in sequence:
   (i) an N-terminal polypeptide from the antigen binding portion of the heavy chain variable region of an antibody;
   (ii) a peptide linker; and
   (iii) a C-terminal polypeptide from the antigen binding portion of the light chain variable region of an antibody.

6. The polypeptide of claim 1 which comprises in sequence
   (i) a N-terminal polypeptide from the antigen binding portion of a first light or heavy first chain of the variable region of an antibody;
   (ii) a first peptide liner;
   (iii) a polypeptide from the antigen binding portion of a second heavy or light chain, respectively, of the variable region of an antibody;
   (iv) a second peptide liner; and
   (v) a C-terminal polypeptide from the antigen binding portion of said first light or heavy first chain, respectively, of the variable region of an antibody.

7. The polypeptide of claim 6 which comprises, in sequence:
   (i) an N-terminal polypeptide from the antigen binding portion of a first light chain variable region of an antibody;
   (ii) a peptide liner;
   (iii) a polypeptide from the antigen binding portion of a second heavy chain variable region of an antibody;
   (iv) a peptide liner; and
   (v) a C-terminal polypeptide from the antigen binding portion of said first light chain variable region of an antibody.

8. The polypeptide of claim 4, 5 or 7 which comprises, prior to said N-terminal region (i), a methionine residue.

9. The polypeptide of claim 1 which is detectably labeled.

10. The polypeptide of claim 1 which is immobilized on an insoluble solid phase.

11. The polypeptide of claim 1 wherein said first polypeptide (a) comprises essentially all of the light chain variable region of said antibody in part (a), and said second polypeptide (b) comprises essentially all of the heavy chain variable region of said antibody in part (b).

12. A single chain polypeptide having binding affinity for a given antigen, said polypeptide comprising:
   (a) a first polypeptide comprising the antigen binding portion of the light chain variable region of an antibody;
   (b) a second polypeptide comprising the antigen binding portion of the heavy chain variable region of an antibody; and
   (c) a peptide linker said first and second polypeptides (a) and (b) into said single chain polypeptide; said single chain polypeptide produced by the method comprising:
   (i) providing a genetic sequence coding for said single chain polypeptide;
   (ii) transforming a host cell with said sequence;
   (iii) expressing said sequence in said host; and
   (iv) recovering said single chain polypeptide having binding affinity for said given antigen.

13. The single chain polypeptide of claim 12 wherein said method further comprises purifying said recovered single chain polypeptide having binding affinity for said given antigen.

14. The single chain polypeptide of claim 12 wherein said polypeptide (a) comprises essentially all of the light chain variable region of said antibody in part (a), and said polypeptide (b) comprises essentially all of the heavy chain variable region of said antibody in part (b).

15. The single chain polypeptide of claim 12 wherein said method comprises, prior to said step (i), operably linking a genetic sequence coding for said first polypeptide (a), to a genetic sequence coding for said second polypeptide (b), to a genetic sequence coding for said peptide liner (c);
   so as to provide said genetic sequence coding for said single chain polypeptide.

16. A method of producing a genetic sequence coding for a single chain polypeptide having binding affinity for a given antigen, which comprises operably linking:
   (A) a genetic sequence coding for a first polypeptide comprising the antigen binding portion of a light chain variable region of an antibody to
   (B) a genetic sequence coding for a polypeptide comprising the antigen binding portion of a heavy chain variable region of an antibody to
   (C) a genetic sequence coding for a peptide linker suitable for linking said polypeptides in (A) and (B) into a single chain polypeptide;
   so as to provide said genetic sequence coding for said single chain polypeptide.

17. The method of claim 16 wherein said polypeptide in (A) comprises essentially all of the light chain variable region; and said polypeptide in (B) comprises essentially all of the heavy chain variable region.

18. The genetic sequence produced by the method of claim 16.

19. In a conjugate of a polypeptide and an imaging agent, the improvement comprising using as said polypeptide the polypeptide of claim 1.

20. In a conjugate of a polypeptide and a toxin, the improvement comprising using as said polypeptide the polypeptide of claim 1.

* * * * *

UNITED STATES PATENT AND TRADEMARK OFFICE
CERTIFICATE OF CORRECTION

PATENT NO. : 5,260,203
DATED : November 9, 1993
INVENTOR(S) : Ladner et al.

It is certified that error appears in the above-indentified patent and that said Letters Patent is hereby corrected as shown below:

On title page, item [73] change "Enzon, Inc." to
--Enzon Labs Inc.--.

Signed and Sealed this

Twenty-seventh Day of September, 1994

Attest:

BRUCE LEHMAN

Attesting Officer           Commissioner of Patents and Trademarks